(12) United States Patent
Greenspan et al.

(10) Patent No.: US 10,937,534 B2
(45) Date of Patent: Mar. 2, 2021

(54) SYSTEM AND METHOD FOR SECURE MEDICATION DISPENSING, MONITORING, AND CONTROL

(71) Applicant: SBG Medical Technologies, Pine Brook, NJ (US)

(72) Inventors: Michael Greenspan, Towaco, NJ (US); David Greenspan, Pine Brook, NJ (US)

(73) Assignee: SBG MEDICAL TECHNOLOGIES, Pine Brook, NJ (US)

( * ) Notice: Subject to any disclaimer, the term of this patent is extended or adjusted under 35 U.S.C. 154(b) by 0 days.

(21) Appl. No.: 16/750,458

(22) Filed: Jan. 23, 2020

(65) Prior Publication Data
US 2020/0234811 A1 Jul. 23, 2020

Related U.S. Application Data

(63) Continuation-in-part of application No. 16/255,087, filed on Jan. 23, 2019.
(Continued)

(51) Int. Cl.
*G16H 20/13* (2018.01)
*A61J 7/04* (2006.01)
(Continued)

(52) U.S. Cl.
CPC ......... *G16H 20/13* (2018.01); *A61B 10/0051* (2013.01); *A61J 7/0069* (2013.01);
(Continued)

(58) Field of Classification Search
CPC ........ G16H 20/13; G16H 10/60; G16H 40/67; G16H 80/00; A61J 7/0418; A61J 7/0084;
(Continued)

(56) References Cited

U.S. PATENT DOCUMENTS 10,124,940 B2 * 11/2018 Blackburn ............... G06F 19/00
2006/0062734 A1 * 3/2006 Melker .................. G16H 80/00
424/10.1

(Continued)

*Primary Examiner* — Michael Collins
(74) *Attorney, Agent, or Firm* — McCarter & English LLP; Beverly W. Lubit

(57) ABSTRACT

A programmable medication dispenser is provided to securely dispense medication to a patient and mitigate the risk of diversion of the medication to an unauthorized user. The programmable medication dispenser may include a processor, a memory, a housing, a biometric verification module, an inner receptacle having a plurality of compartments for storing the medication, and a gate for dispensing the medication from one of the compartments. A patient may access the medication stored within the medication dispenser according to a prescribed dosing schedule based on instructions executed by the processor after verifying his or her identify via the biometric verification module. A system is also provided for securely dispensing, monitoring, controlling medication for a patient using the programmable medication dispenser and for mitigating the risk of diversion of the medication to an unauthorized user. The system could be implemented in a cloud-based environment wherein centralized, cloud-based monitoring and control of a network of medication dispensing systems is provided, and the system could function as a centralized portal for allowing healthcare providers to access patient healthcare data, as well as for allowing insurers and other entities to access such data, as needed.

26 Claims, 32 Drawing Sheets

Related U.S. Application Data

(60) Provisional application No. 62/796,301, filed on Jan. 24, 2019.

(51) Int. Cl.
*A61J 7/00* (2006.01)
*G16H 10/60* (2018.01)
*G16H 40/67* (2018.01)
*G16H 80/00* (2018.01)
*A61B 10/00* (2006.01)

(52) U.S. Cl.
CPC ............ *A61J 7/0084* (2013.01); *A61J 7/0418* (2015.05); *A61J 7/0445* (2015.05); *A61J 7/0481* (2013.01); *G16H 10/60* (2018.01); *G16H 40/67* (2018.01); *G16H 80/00* (2018.01)

(58) Field of Classification Search
CPC ...... A61J 7/0481; A61J 7/0445; A61J 7/0069; A61B 10/0051
USPC .................................................. 700/231–244
See application file for complete search history.

(56) References Cited

U.S. PATENT DOCUMENTS

| | | | | |
|---|---|---|---|---|
| 2015/0259110 A1* | 9/2015 | Blackburn | .......... | G07F 17/0092 222/1 |
| 2016/0029963 A1* | 2/2016 | Hyde | ........ | A61B 5/11 600/301 |
| 2017/0316408 A1* | 11/2017 | Bernesby | ............ | G06Q 20/3829 |
| 2019/0307647 A1* | 10/2019 | Greenspan | ............ | A61B 5/4833 |

\* cited by examiner

SYSTEM AND METHOD FOR SECURE MEDICATION DISPENSING, MONITORING, AND CONTROL

CROSS REFERENCE TO RELATED APPLICATION(S)

The present application is a continuation-in-part of U.S. application Ser. No. 16/255,087 (filed Jan. 23, 2019), and claims priority to U.S. Provisional Application Ser. No. 62/796,301 filed on Jan. 24, 2019. The entire disclosure of each of these is expressly incorporated by reference.

TECHNICAL FIELD

The present disclosure relates generally to the field of medication dispensing. More specifically, the present disclosure relates to a system for securely dispensing medication to a patient using a secure, programmable medication dispenser and mitigating the risk of diversion of medication to an unauthorized user, as well as a system for remote (cloud-based) monitoring and control of networked dispensing systems.

RELATED ART

In the medication dispensing field, typical systems and methods for dispensing medication fail to allow physicians and pharmacies to effectively limit and monitor the usage of prescription medication by a patient. Such systems and methods are problematic because of the addictive nature of some prescription medication such as opioid painkillers, CNS depressant, and stimulants and the potential for abuse of prescription medication. Thus, a secure system and method for dispensing medication to a patient is needed. Accordingly, the system of the present disclosure addresses these and other needs.

SUMMARY

A programmable medication dispensing system is provided which securely dispenses medication to a patient and mitigates the risk of diversion of the medication to an unauthorized user. The programmable medication dispensing system may include a processor, a memory, a housing, a biometric verification module, an inner receptacle having a plurality of compartments for storing the medication, and a gate for dispensing the medication from one of the compartments. A patient may access the medication stored within the medication dispenser according to a prescribed dosing schedule based on instructions executed by the processor after verifying his or her identify via the biometric verification module.

A system for securely dispensing medication to a patient using the programmable medication dispenser and for mitigating the risk of diversion of the medication to an unauthorized user is also provided. The system may include the programmable medication dispenser and a network-based control system wherein the programmable medication dispenser communicates and exchanges information with a cloud-based patient database, an operations center and medical providers via the network. The system could be implemented in a cloud-based environment wherein centralized, cloud-based monitoring and control of a network of medication dispensing systems is provided. Moreover, the system could function as a centralized portal for allowing healthcare providers to access patient healthcare data, as well as for allowing insurers and other entities to access such data, as needed. For example, the system could function as a continuously updated repository of patient behavioral information wherein the cloud-based patient database could be updated by messages automatically transmitted by the programmable medication dispenser to the patient database each time a patient attempts to access the medication stored within the medication dispenser both in compliance with his or her prescription and otherwise. The cloud-based patient database could be accessible to medical providers and operations center administrators to facilitate securely dispensing medication to the patient using the programmable medication dispenser and for mitigating the risk of diversion of the medication to an unauthorized user. The cloud-based patient database could also be accessible to third parties (e.g., researchers) with the purchase of a license wherein access to the cloud-based patient database and patient data are in compliance with Health Insurance Portability and Accountability Act (HIPAA) regulations.

BRIEF DESCRIPTION OF THE DRAWINGS

The foregoing features of the present disclosure will be apparent from the following Detailed Description of the Invention, taken in connection with the accompanying drawings in which.

DETAILED DESCRIPTION

The present disclosure relates to a system for securely dispensing medication to a patient using a secure, programmable medication dispenser and an associated cloud-based monitoring and control system, and for mitigating the risk of diversion of medication to an unauthorized user, as described in detail below in connection with FIGS. 1-32.

Figure 1:
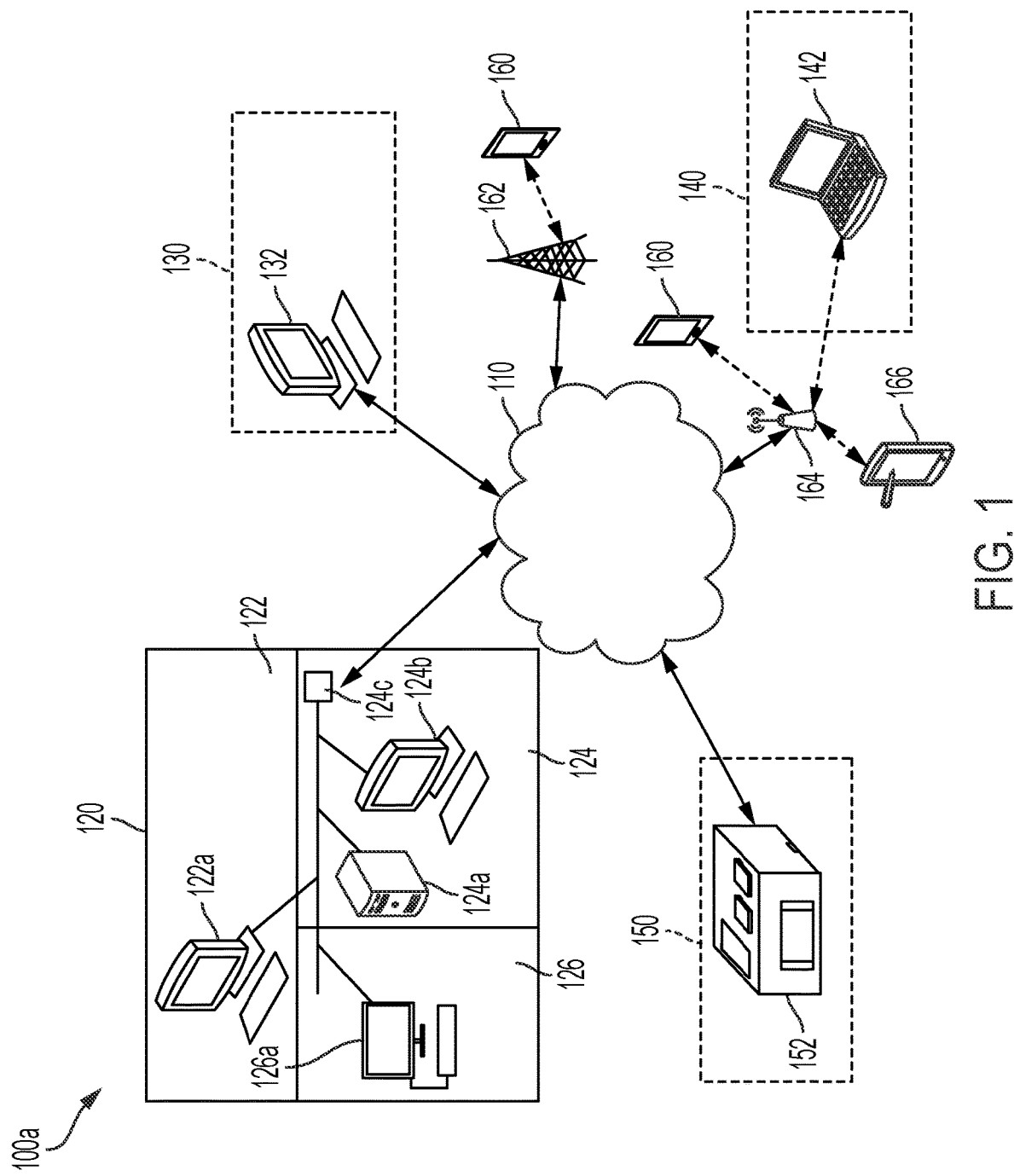
FIG. 1 is a diagram illustrating an overview of components capable of being utilized to implement the system of the present disclosure.

Turning to the drawings, FIG. 1 is a diagram illustrating an overview of components capable of being utilized to implement the system of the present disclosure. The system 100a could include a network 110; an operations center 120; a physician's office 130; a pharmacy 140; a patient residence or workplace 150; and a variety of wireless devices including, but not limited to, a mobile terminal 160 and a tablet 166. The network 110 facilitates communication and provides for secure data transport and exchange between the various components of the system 100a. For example, the network 110 may communicate Internet Protocol (IP) packets, frame relay frames, Asynchronous Transfer Mode (ATM) cells, or other information between network addresses. The network 110 could include one or more local area networks (LANs), metropolitan area networks (MANs), wide area networks (WANs), all or a portion of a global network such as the Internet, or any other communication system or systems at one or more locations. Additionally, the network 110 could be part of a cloud-based remote monitoring and control system which is networked with, communicates with, and controls operation of a global network of dispensing devices in accordance with the present disclosure. Information exchanges among the system 100a components may adhere to the International Organization for Standardization (ISO) HL-7 Standard.

The operations center 120 could include a call in center 122 having a computer 122a; a network control center 124 having a server 124a, a computer 124b and a network head end 124c; and a logistics and maintenance center 126 having a computer 126a. The operations center provides call-in help lines for patients, physicians (i.e., prescribers), and pharmacists; the network control center 124 provides access and control authorization to the network 110; and the logistics and maintenance center 126 provides pill dispenser 152 logistics and maintenance services.

The physician's office 130 could include a computer 132 for transmitting a medication prescription to a pharmacy 140 via the network 110 and a wireless access point 164 (e.g., an IEEE 802.11 wireless access point). Alternatively, a physician could transmit a medication prescription to the pharmacy computer 142 from a mobile terminal 160 via a wireless base station 162 and the network 110. The mobile terminal 160 could include, but is not limited to, a personal computer, a laptop computer, a smart telephone, a pager, a personal digital assistant (PDA) and/or a cloud-based computing platform. A physician could also transmit a medication prescription to the pharmacy computer 142 from the mobile terminal 160 or a tablet 166 via the wireless access point 164. It is noted that a physician could communicate directly with the network 110 or indirectly with the network 110 via any suitable device or network device.

The pharmacy 140 could include a computer 142 for receiving the transmitted medication prescription. A pharmacist issues the pill dispenser 152 with the prescribed medication to an authorized patient. Specifically, a pharmacist can load the pill dispenser 152 with the prescribed medication and program the pill dispenser 152 according to dosing information transmitted from a physician via the network 110. A pharmacist may utilize the computer 142 to review information including, but not limited to, medication inventory, pill dispenser inventory and patient health information. An inventory of pill dispensers 152 could be maintained within a pharmacy's storage facilities or an integrated health network's centralized distribution supply channel.

The pill dispenser 152 is portable and can accompany a patient when travelling. As such, a patient's residence or workplace 150 could be used to store the pill dispenser 152. For example, the pill dispenser 152 may be stored at a patient's residence or workplace if the patient is an outpatient. Alternatively, the pill dispenser 152 could be stored at in a patient's room in a host healthcare facility if the patient is an in-patient.

The system 100a could function as a continuously updated repository of patient behavioral information wherein a patient database could be updated by messages automatically transmitted by the pill dispenser 152 to the patient database each time a patient attempts to access the medication stored within the pill dispenser 152 both in compliance with his or her prescription and otherwise. The patient database could be stored on the network control center server 124a of the operations center 120 or could be resident in a secure cloud storage facility (e.g, cloud-based) such as Dropbox Business; Egnyte Business; Amazon S3; and Microsoft OneDrive for Business.

The patient database could be accessible to medical providers and operations center administrators to facilitate securely dispensing medication to the patient using the pill dispenser 152 and for mitigating the risk of diversion of the medication to an unauthorized user. The patient database could also be accessible to third parties (e.g., researchers) with the purchase of a license wherein access to the patient database and patient data therein would be in compliance with Health Insurance Portability and Accountability Act (HIPAA) regulations.

Figure 2:
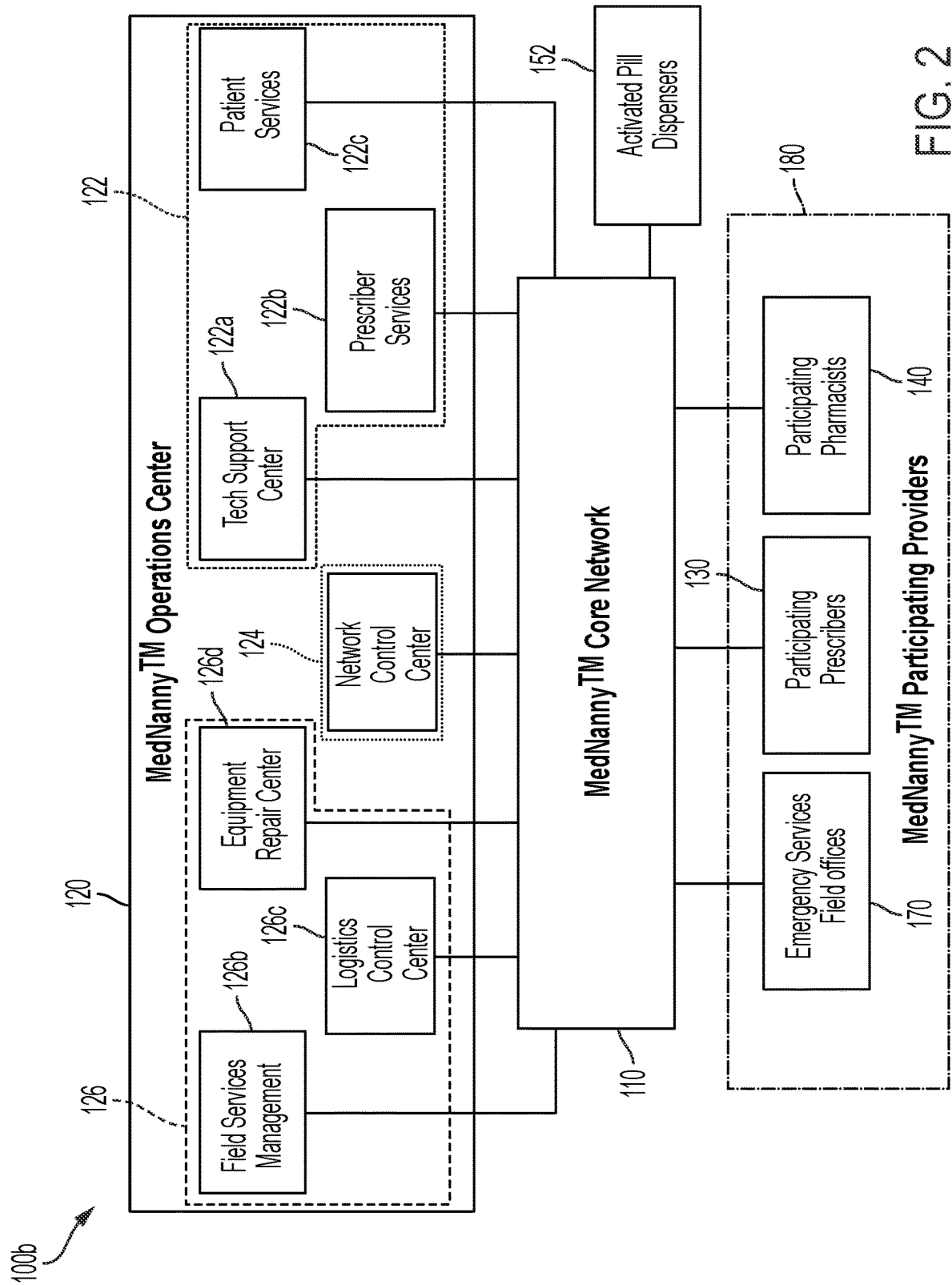
FIG. 2 is a diagram illustrating a network configuration of the components of FIG. 1 in greater detail.

FIG. 2 is a diagram illustrating a network configuration of the components of FIG. 1 in greater detail. The system 100b comprises hardware and software components to provide the secure containment, dispensing, monitoring, and control of medication as prescribed by a licensed physician or care giver. For example, the system 100b can provide for the secure containment and dispensing of opioid medication for a workable an efficient mitigation of the world-wide opioid abuse epidemic.

The system 100b could include the network 110; the operations center 120 including the call in center 122, the network control center 124 and the logistics and maintenance center 126; pill dispensers 152 and participating providers 180 including participating physicians 130, participating pharmacists 140 and emergency services field offices 170. The system can also include special purpose control software and databases (not shown) that can reside on the physician's office computer 132; the pharmacy computer 142; the operations center 120; administrator computers at integrated health care centers; and secure cloud storage. The software can be implemented and updated through secure cloud services. The network 110 connects the operations center 120 and elements therein, activated pill dispensers 152 and the participating providers 180 wherein the special purpose control software and databases running on the computing elements thereof maintain private and secure patient records.

The system 100b is dynamic and provides several advantages over conventional prescription systems and methods because of the interconnectivity between the operations center 120, the pill dispensers 152 and the participating providers 180 via the network 110. For example, the system 100a provides for an early warning system to detect patient medication abuse and/or medication diversion; a collection and reporting system for dosing compliance verification; a deterrent against medication theft and diversion; and a system that is compliant with the HIPPA patient privacy regulations. In addition, the pill dispenser 152 of the system 100b provides a safe and tamper-resistant device for dispensing valid prescriptions of potentially addictive medication and for collecting patient data for abuse risk identification and focused prescribing purposes.

The network 110 is an integrated voice and data network based on Internet technology. The network 110 facilitates communication and provides for secure data transport and exchange between the operations center 120, the pill dispensers 152 and the participating providers 180. For example, the network 110 may communicate Internet Protocol (IP) packets, frame relay frames, Asynchronous Transfer Mode (ATM) cells, or other information between network addresses. Information exchanges among the system 100b components may adhere to the International Organization for Standardization (ISO) HL-7 Standard. The network 110 could include one or more local area networks (LANs), metropolitan area networks (MANs), wide area networks (WANs), all or a portion of a global network such as the Internet, or any other communication system or systems at one or more locations. For example, integrated health systems that adopt the system 100a may incorporate the system 100b components into their respective corporate networks which could include LANs within care centers and WANs interconnecting these care centers. The pill dispensers 152 could be connected to the network 110 via Wi-fi when in range of Wi-fi networks or hotspots. Alternatively, the pill dispensers 152 could be connected to the network 110 via cable and/or a cellular network.

The operations center 120 includes the call in center 122, the network control center 124 and the logistics and maintenance center 126 and provides centralized management and support for participating providers 180 and their respective activities. The call in center 122 includes a tech support center 122a, prescriber services 122b and patient services 122c which respectively provide call in support for technical issues, patients and prescribers and pharmacists. The network control center 124 manages the network 110. For example, the network control center 124 provides access and control authorization to the network 110. The logistics and maintenance center 126 includes field services management 126b, a logistics control center 126c and an equipment repair center 126d. The field services management 126b manages the emergency services field offices 170 of the participating providers 180 and the logistics control center 126c supports pill dispenser 152 logistics, supply chain management and distribution. For example, the logistics control center 126c can provide for global positioning system (GPS) tracking of a reported stolen pill dispenser 152. The equipment repair center 126d provides pill dispenser 152 maintenance and repair.

The pill dispenser 152 is issued to a patient and holds prescription medication that is dispensed to the patient based on patient specific operating instructions (i.e., firmware) and data downloaded to a pill dispenser 152 controller by a participating pharmacist 140. Specifically, the pill dispenser 152 is programmed by the participating pharmacist 140 when loading the prescription medication into the pill dispenser 152. The pill dispenser 152 firmware controls the functionality of the pill dispenser 152. For example, the pill dispenser 152 firmware enables the pill dispenser 152 to store the patient identification number and dosing schedule; perform patient identification via biometric testing; perform saliva analysis and reporting; dispense medication according to a prescribed dosing schedule; track the amount of medication removed by a patient from the pill dispenser 152 and the remaining amount of medication within the pill dispenser 152; detect and report tampering; perform dispensing gate lockdown and restoration procedures; and implement GPS tracking and location reporting.

The system 100b could function as a continuously updated repository of patient behavioral information wherein a patient database could be updated by messages automatically transmitted by the pill dispenser 152 to the patient database each time a patient attempts to access the medication stored within the pill dispenser 152 both in compliance with his or her prescription and otherwise. For example, the patient database could store patient data including, but not limited to, a patient identification number; a patient pill dispenser 152 serial number; a patient prescribed dosing schedule; patient biometric identification testing information; patient saliva analysis information; dispensing medication events; pill dispenser 152 tampering events; and pill dispenser 152 lockdown and restoration events. The patient database could be stored on the network control center server 124a of the operations center 120 as shown in FIG. 1 or could be resident in a secure cloud storage facility (e.g., cloud-based) such as Dropbox Business; Egnyte Business; Amazon S3; and Microsoft OneDrive for Business.

The patient database could be accessible to medical providers and operations center administrators to facilitate securely dispensing medication to the patient using the pill dispenser 152 and for mitigating the risk of diversion of the medication to an unauthorized user. The patient database could also be accessible to third parties (e.g., researchers)

with the purchase of a license wherein access to the patient database and patient data therein would be in compliance with HIPAA regulations.

A patient may return the pill dispenser 152 to a participating pharmacist 140 when the pill dispenser 152 requires scheduled maintenance or is compromised by tampering, accidental damage or normal wear and tear. Special purpose diagnostic software residing on the pharmacy computer 142 provide for the participating pharmacist 140 to perform tests for physical integrity, mechanical function and software currency and functionality. Test results can be stored according to the pill dispenser 152 serial number and made available to the logistics control and maintenance center 126 of the operations center 120.

The participating providers 180 include participating prescribers 130, participating pharmacists 140 and emergency services field offices 170. As mentioned above, special purpose control software can reside on the computing elements of the participating prescribers 130 and participating pharmacists 140 and can be implemented and updated through secure cloud services. For example, software on the prescriber's computer 132 or an administrators computer at an integrated health care center can enable the participating prescriber 130 to generate and transmit prescriptions for medication; associate an issued pill dispenser 152 serial number with a patient in accordance with HIPAA requirements to protect patient confidentiality; store, display and manage patient data describing interactions with the pill dispenser 152; monitor, display and manage patient interaction with the pill dispenser 152 including tamper, theft and diversion alerts; and monitor patient compliance with dosing schedules.

Software on the pharmacy's computer 142 can enable a participating pharmacist 140 to receive patient prescriptions transmitted by participating prescribers 130 via the network 110; program the pill dispenser 152 processor with a patient's identification and customized dosing schedule; monitor pill dispenser 152 anti-abuse and anti-theft alert signals; perform pill dispenser 152 diagnostics; and unlock the pill dispenser 152 upon receipt of authorization from a participating prescriber 130.

As mentioned above, participating prescribers 130 may access and review a patient database including a variety of transaction records resident in a network control center server 124a of the operations center 120 as shown in FIG. 1 or resident in a secure cloud storage facility (e.g, cloud-based) such as Dropbox Business; Egnyte Business; Amazon S3; and Microsoft OneDrive for Business. For example, participating prescribers 130 may access records including, but not limited to, a pill dispenser 152 serial number issued to a patient; patient compliance with medication dosing schedules; patient attempts to tamper with the pill dispenser 152; reports of pill dispenser 152 theft; unlock commands to the pill dispenser 152 issued by patient services 122c; and indications of drug diversion to third parties (e.g., inconsistent drug levels in a patient's saliva samples). Participating pharmacists 140 may also access and review the patient database. In addition, participating pharmacists 140 may maintain records of the pill dispenser serial number issued to the patient and the prescriptions filled and refilled.

The system 100b provides useful individual patient and aggregate patient population statistics based on the data collected from the special purpose control software and stored on the databases running on the computing elements of the operations center 120 and elements therein, activated pill dispensers 152 and the participating providers 180.

For example, at the individual patient level, a participate prescriber 180 can use a patient's dosage compliance history and related behavioral data to obtain a comparison of a patient's prescribed dosage vs. actual usage; a tally of real-time; remaining dosage reserve held in the pill dispenser 152; alerts of pill dispenser 152 tampering; an indication that a patient is likely diverting prescription medication from the pill dispenser 152; and specifics regarding a patient's prescription medication usage patterns including increases or decreases in frequency of use, time intervals between uses, self-imposed cessation and related usage patterns.

Aggregate patient population statistics can be derived from a local or regional patient population. For example, organizations studying the abuse of potentially addictive medications can utilize the system 100b to collect and aggregate data on trends and patterns across the patient universe such as, but not limited to, general patient abuse/misuse; general diversion patterns; comparative prescribed dosing vs. actual usage; and unused drug returns. The trends can be can be categorized as a function of population age; gender; ethnicity; physical condition; prescription drug type; geographic region; specialty of prescriber; and the patients' insurance carrier.

Figure 3:
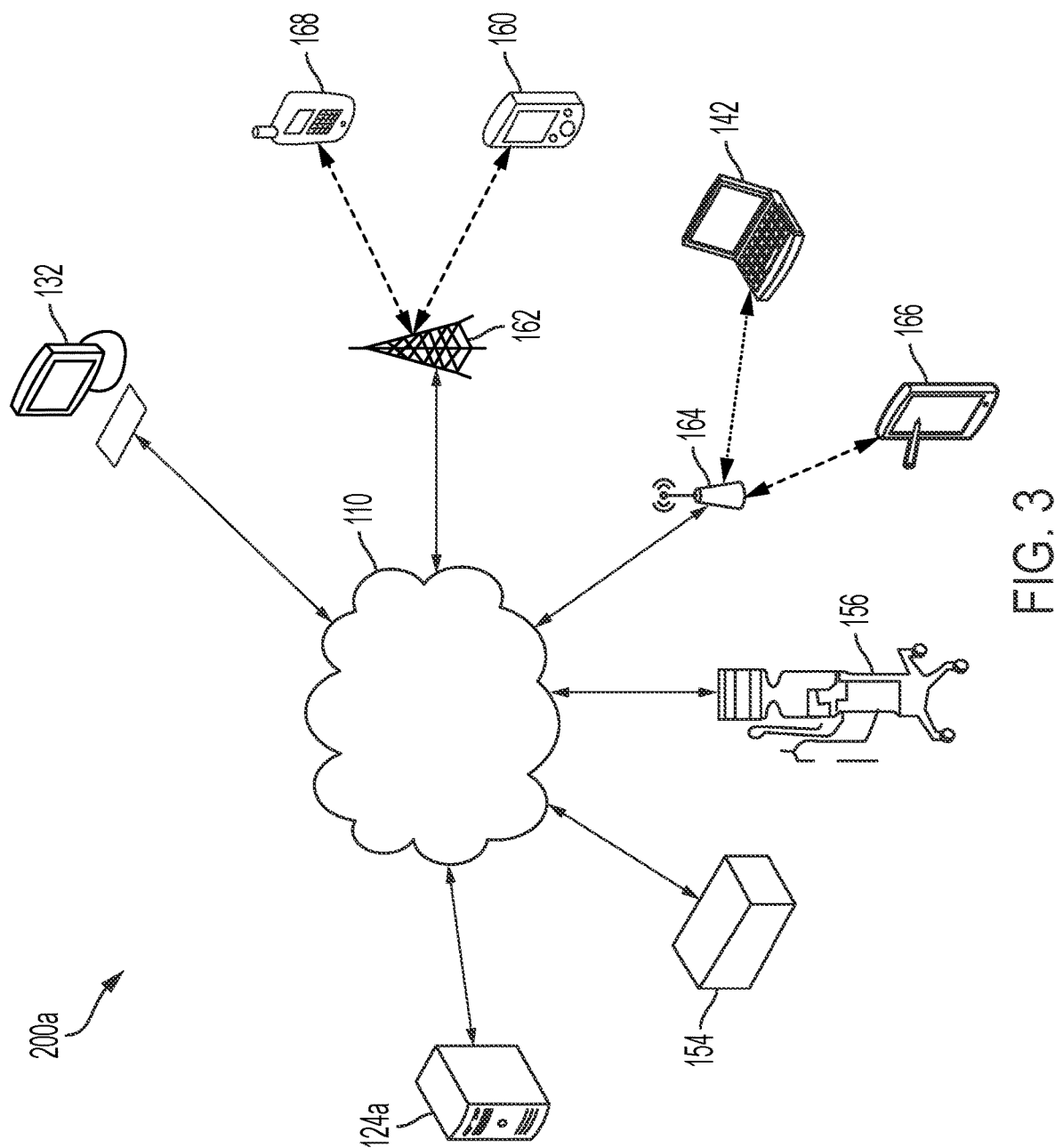
FIG. 3 is another diagram illustrating an overview of components capable of being utilized to implement the system of the present disclosure.

FIG. 3 is another diagram illustrating an overview of components capable of being utilized to implement the system of the present disclosure. The system 200a could include a network 110; at least one server 124a; a physician's computer 132; a pharmacy computer 142; a device 154; a ventilator 156; a mobile terminal 160; a wireless base station 162; a wireless access point 164; a tablet 166; and a cellular telephone 168. The mobile terminal 160 could include, but is not limited to, a personal computer, a laptop computer, a smart telephone, a pager, a personal digital assistant (PDA) and/or a cloud-based computing platform.

The network 110 facilitates communication and provides for secure data transport and exchange between the various components of the system 200a. For example, the network 110 may communicate Internet Protocol (IP) packets, frame relay frames, Asynchronous Transfer Mode (ATM) cells, or other information between network addresses. The network 110 could include one or more local area networks (LANs), metropolitan area networks (MANs), wide area networks (WANs), all or a portion of a global network such as the Internet, or any other communication system or systems at one or more locations. Information exchanges among the system 100a components may adhere to the International Organization for Standardization (ISO) HL-7 Standard. Specifically, the network 110 facilitates communication between the device 154 and/or ventilator 156, the at least one server 124a and the physician's computer 132; the pharmacy computer 142; the mobile terminal 160; the tablet 166; and the cellular telephone 168. Each server 124a includes any suitable computing or processing device that can provide computing services for one or more of the physician's computer 132; the pharmacy computer 142; the mobile terminal 160; the tablet 166; and the cellular telephone 168. Each server 124a could, for example, include one or more processing devices, one or more memories storing instructions and data, and one or more network interfaces facilitating communication over the network 110.

Each of the physician's computer 132; the pharmacy computer 142; the mobile terminal 160; the tablet 166; and the cellular telephone 168 represents any suitable computing or processing device that interacts with at least one server or other computing device(s) over the network 110.

In the system 200a, one or more of the pharmacy computer 142; the mobile terminal 160; the tablet 166; and the cellular telephone 168 may communicate indirectly with the network 110. For example, the mobile terminal 160 and the cellular telephone 168 may communicate via one or more base stations 162, such as cellular base stations or eNodeBs. Also, the pharmacy computer 142 and the tablet 166 may communicate via one or more wireless access points 164, such as IEEE 802.11 wireless access points. Note that these are for illustration only and that each of the pharmacy computer 142; the mobile terminal 160; the tablet 166; and the cellular telephone 168 could communicate directly with the network 110 or indirectly with the network 110 via any suitable intermediate device(s) or network(s).

The device 154 may be one example of a pill dispenser 152. The device 154 may communicate with the at least one server 124a and various devices including the physician's computer 132; the pharmacy computer 142; the mobile terminal 160; the tablet 166; and the cellular telephone 168 via the network 110. In various embodiments the device 154 may communicate through the wireless base station 162 or the wireless access point 164. In addition, the ventilator 156 may communicate with the at least one server 124a and various devices including the physician's computer 132; the pharmacy computer 142; the mobile terminal 160; the tablet 166; and the cellular telephone 168 via the network 110. In various embodiments the ventilator 156 may communicate through the wireless base station 162 or the wireless access point 164. The device 154 could also communicate with a cloud-based monitoring and control system, such that Internet-of-Things (IoT) connectivity and remote control is provided for the device 154 by the cloud-based monitoring and control system.

Although FIG. 3 illustrates one example of the system 200a, various changes may be made to FIG. 3. For example, the system 200a could include any number of each component in any suitable arrangement. In general, computing and communication systems come in a wide variety of configurations, and FIG. 1 does not limit the scope of the present disclosure to any particular configuration. While FIG. 1 illustrates one operational environment in which various components disclosed herein can be used, these components could be used in any other suitable system.

Figure 4:
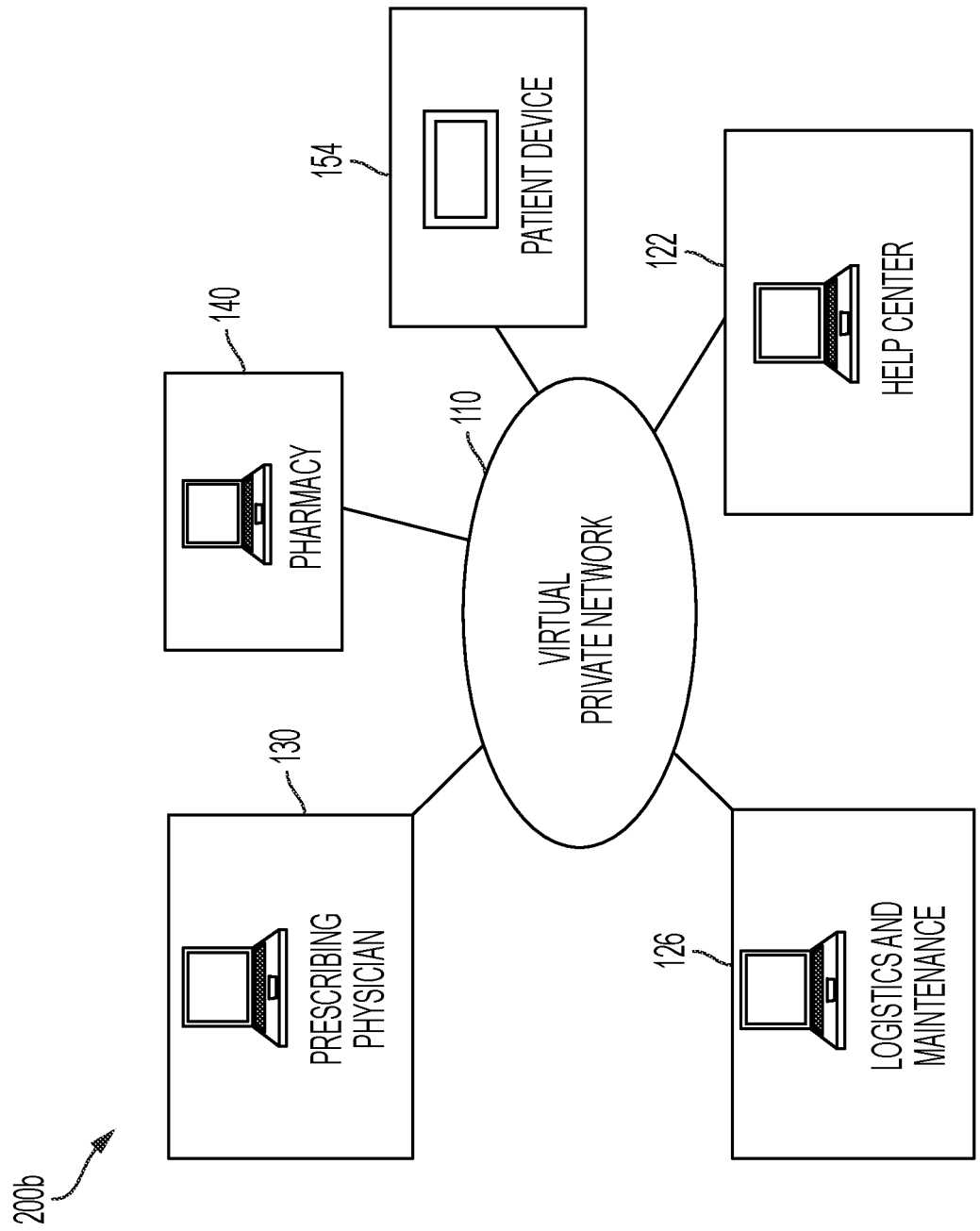
FIG. 4 is a diagram illustrating another network configuration of components capable of being utilized to implement the system of the present disclosure.

FIG. 4 is a diagram illustrating another network configuration of components capable of being utilized to implement the system of the present disclosure. The system 200b could include a virtual private network 110; a help center 122; a logistics and maintenance center 126; a prescribing physician's office 130; a pharmacy 140; and a patient device 154. The system 200b could includes the virtual private network 110 and one or more devices connected to the virtual private network 110. The one or more devices may include a device used by a prescribing physician 130 in prescribing the prescription medication; a device used by the pharmacy 140 dispensing the prescription medication; the patient device that dispenses the prescription medication; a device used by the help center 122; and a client device used by the logistics and maintenance center 126. The virtual private network allows the various devices to communicate with one another regarding the patient, the patient's prescription, and/or the state of the patient device, for example if the patient device is damaged. Of course, the network 110 need not be limited to a virtual private network, and could be part of a cloud-based system which provides network connectivity (e.g., Internet-of-things), monitoring, and control of the devices 154, from anywhere in the word.

In one embodiment, the virtual private network 110 may be used to provide a private communication network to facilitate the patient receiving their medication. The prescribing physician 130 may send a message, via their device, to the pharmacy 140 and a patient's device 154 that a patient has been prescribed a medication. This message may include information regarding the name of the medication, the dosage, duration of the prescription (e.g., one month), and the name or other identifying information of the patient to receive the medication. The device located at the pharmacy 140 may receive the message and initiate a procedure to fill the prescription. When the prescription is filled, the device at the pharmacy 140 may send a message to the patient device 154 that the prescription is ready for pickup. The patient device 154 receives this message and notifies the patient that their prescription is ready. When the patient receives this message, the patient physically brings their device 154 to the pharmacy 140. The pharmacist, or another authorized user in the pharmacy, loads the medication into the patient device 154 and loads instructions into the patient device 154 for dispensing the medication during the duration of the prescription. The patient then returns home with the patient device 154 and the medication is dispensed throughout the duration of the prescription.

The patient device 154 may also send a message to the pharmacy 140 and prescribing physician 130 over the virtual private network 110 that the patient device is nearing an EMPTY state. The device at the pharmacy 140 receives the message, and refers back to the instructions originally received from the prescribing physician 130. The instructions may state that the patient should visit the prescribing physician 130 before being prescribed more medication. If so, the pharmacy 140 does not prepare a new dosage of medication, and waits for a message from the prescribing physician 130 that the physician has prescribed medication.

Alternatively, the instructions may have stated the patient may receive a new dosage of medication without visiting the prescribing physician 130. These instructions may further include limitations that the patient device 154 must not have transmitted a DAMAGED signal during the duration of the previous prescription. If the instructions stated the patient may receive a new dosage of medication without visiting the prescribing physician 130, the pharmacy 140 prepares a new dosage of medication for the patient.

When the prescription is filled, the device at the pharmacy may send a message to the patient device 154 that the prescription is ready for pickup. The patient device 154 receives this message and notifies the patient that their prescription is ready. When the patient receives this message, the patient physically brings their patient device 154 to the pharmacy 140. The pharmacist, or another authorized user in the pharmacy 140, loads the medication into the patient device 154 and loads instructions into the patient device 154 for dispensing the medication during the duration of the prescription. The patient then returns home with the patient device 154 and the medication is dispensed throughout the duration of the prescription. As such, the prescribing physician 130 may responsibly and accurately prescribe the patient medication without under prescribing the patient for fear of diversion of the prescribed medication.

The patient device 154 may also transmit a HELP signal to the help center 122 device over the virtual private network 110. The patient may manually input this message, for example if the patient device 154 has malfunctioned or otherwise failed to dispense the medication as prescribed, or the patient device 154 may automatically send the message, for example if the patient device controller detects the patient device 154 has been compromised. The help center 122 may run a troubleshooting protocol to try and identify the problem, or may transmit a message directing the patient to bring the patient device 154 to the pharmacy 140 for inspection.

The patient device 154 may automatically lock down if the HELP signal was sent because of an attempt to tamper with the patient device 154. In such a case, the patient device 154 must be unlocked by an authorized pharmacy 140 after the pharmacy 140 has been authorized to unlock the device by the prescribing physician 130. This protocol prevents a patient from gaining access to a greater dosage of medication than they were prescribed. The patient device 154 may be unlocked remotely by the pharmacy 140 or the pharmacy 140 may require the patient device 154 to be physically brought to the pharmacy 140 for inspection before it is unlocked. The prescribing physician 130 may transmit a message over the virtual private network 110 to the pharmacy 140 to discontinue the dispensing function of the patient device 154. The prescribing physician 130 may transmit this message in response to receiving a notification of tampering with the patient device 154, theft of the patient device 154 or for any other reason.

The pharmacy 140 may require the patient device 154 to be brought in for physical inspection or for regular maintenance. The pharmacist, or other authorized pharmacy personnel, may physically inspect the patient device 154 for physical integrity and mechanical function or may run a software diagnostic through the virtual private network 110. The logistics and maintenance device performs a diagnostic check to determine if the software is functioning properly. The results of the diagnostic test are stored on the pharmacy's device with the patient device 154 and patient identification. For example, patient device 154 identification information may include the device's serial number.

The logistics and maintenance device is used to manage the virtual private network 110. The logistics and maintenance device maintains records of compliance with medication dosing schedules, patient identification records, patient device 154 records, records of the patient device 154 being tampered with, and patient device 154 diagnostic records.

Although FIG. 4 illustrates one example of the system 200b, various changes may be made to FIG. 4. For example, the system 200b could include any number of each component in any suitable arrangement, and FIG. 4 does not limit the scope of the present disclosure to any particular configuration. For example, the system 200b may include one or more prescribing physicians 130, one or more pharmacies 140, and one or more patient devices 154.

Figure 5:
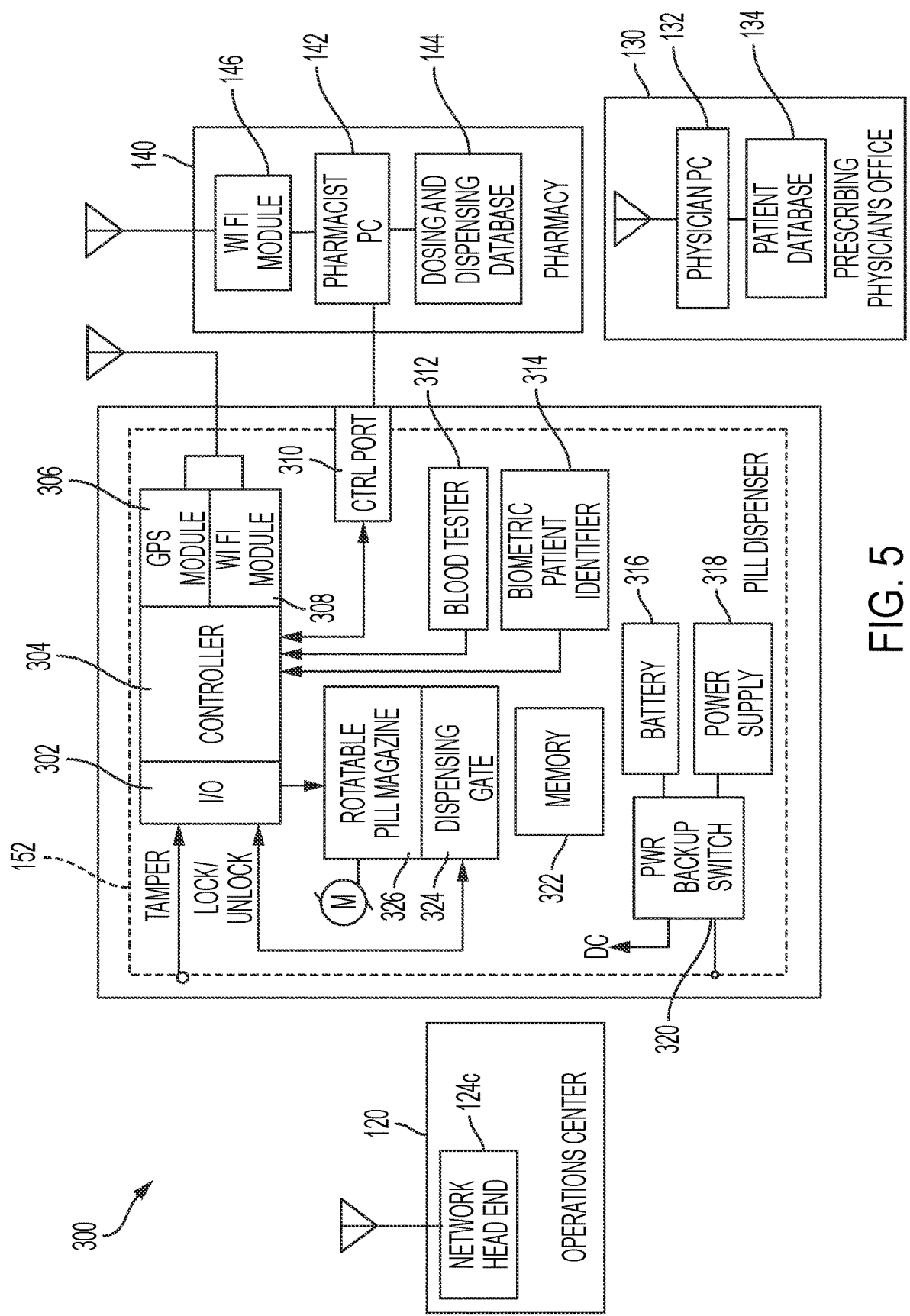
FIG. 5 is a diagram illustrating hardware and software components capable of being utilized to implement the system of the present disclosure.

FIG. 5 is a diagram illustrating hardware and software components capable of being utilized to implement the system of the present disclosure As shown in FIG. 5, the system 300 may include an operations center 120, pill dispenser 152, a participating prescriber 130 and a participating pharmacy 140.

The operations center includes the network head end 124c, at least one communications unit (e.g., transceiver), at least one processing device, and a memory. The processing device executes instructions that may be loaded into the memory. The processing device may include any suitable number(s) and type(s) of processors or other devices in any suitable arrangement. Example types of processing devices include microprocessors, microcontrollers, digital signal processors, field programmable gate arrays, application specific integrated circuits, and discreet circuitry.

The communications unit supports communications with other systems or devices, for example the pill dispenser 152, the pharmacy 140, and the prescribing physician's office 130. For example, the communications unit could include a network interface card or a wireless transceiver facilitating communications over the network 110. The communications unit may support communications through any suitable physical or wireless communication link(s).

The pill dispenser 152 includes an input/output (I/O) interface 302; a controller 304; GPS module 306; a communications module 308 having a WI-FI module; a control port 310; a blood tester 312; a biometric patient identifier 314; a battery 316; a power supply 318; a power backup switch 320; a memory 322; a dispensing gate 324; a rotatable pill magazine 326; a lock/unlock mechanism and a tampering detection mechanism.

The controller 304 may include a processor. The controller 304 executes instructions that may be loaded into the memory 322. The processor may include any suitable number(s) and type(s) of processors or other devices in any suitable arrangement including, but not limited to, microprocessors, microcontrollers, digital signal processors, field programmable gate arrays, application specific integrated circuits, and discreet circuitry.

The memory 322 represents any structure(s) capable of storing and facilitating retrieval of information (such as data, program code, and/or other suitable information on a temporary or permanent basis). For example, the memory 322 could be a random access memory (RAM), persistent storage or any other suitable volatile or non-volatile storage device(s). The persistent storage may contain one or more components or devices supporting longer-term storage of data including, but not limited to, a read only memory (ROM); a hard drive, Flash memory or an optical disc. The memory 322 may store instructions relating to the patient's dosing schedule (e.g., a time period within which to dispense medication to a patient) and operational processor command data. The memory 322 may store records of a patient's interaction with the pill dispenser 152. For example, the memory 322 may store, among other records, a log of the dates and times a patient accesses the pill dispenser 152; records of tampering with the pill dispenser 152; and records of diverting medication to an unauthorized patient.

The I/O interface 302 provides for the input and output of data. For example, the I/O interface 302 may provide a connection for the pill dispenser 152 to connect to a pharmacist computer 132 located in a pharmacy 130. Accordingly, the connection allows a pharmacist, or other authorized personnel, to upload instructions to the pill dispenser 152 including, but not limited, to a dosing schedule for the dispensing medication and/or baseline biometric data for a patient.

The communications module 308 includes a WI-FI module and supports communications with other systems or devices. The communications module 308 could include any suitable physical or wireless communication link(s) to support communications with other systems or devices. For example, the communications module 308 could include a network interface card or a wireless transceiver to facilitate communications with at least one of the operations center 120, the prescribing physician's office 130 or the pharmacy 140 over the network 110.

The controller 304 can utilize information received from the WI-FI module of the communications module 308 or the GPS module 306 to track a location of the pill dispenser 152. For example, the communications module 308 may transmit the location of the pill dispenser 152 to at least one of the operations center 120, the prescribing physician's office 130 or the pharmacy 140.

The rotatable pill magazine 326 contains medication to be dispensed to a patient at a predetermined time. The rotatable pill magazine 326 is rotatable about an axis and may be pre-loaded with medication by a pharmacist before the patient is issued the pill dispenser 152. The rotatable pill magazine 326 may have any configuration or shape so long as the size of the rotatable pill magazine 326 provides for the rotation of the rotatable pill magazine 326 about an axis within the housing of the pill dispenser 152.

The dispensing gate 324 is configured to operate in an OPEN state and a CLOSED state. In the OPEN state, the dispensing gate opens to allow a patient to access medication and in the CLOSED state the dispensing gate closes to prevent a patient from accessing medication. The dispensing gate 324 may raise, lower or operate on a hinge to change from the CLOSED state to the OPEN state or vice versa.

The control port 310 is configured to allow the physical connection of the pill dispenser 152 to an exterior device. For example, a pharmacist or authorized pharmacy personnel may connect the pill dispenser 152 to a device at the pharmacy 140 via a USB, USB-C, or any other suitable connection to run a diagnostic check on the pill dispenser 152, to upload dispensing instructions to the pill dispenser 152 or for any other reason.

The biometric patient identifier 314 identifies a patient attempting to access the pill dispenser 152 during a specified time period for dispensing medication. The patient interacts with the biometric patient identifier 314 by providing biometric data such as a fingerprint, typing a passcode, facial recognition, or a retina scan. The biometric patient identifier 314 compares the biometric data supplied by the patient with the patient's baseline biometric data information stored in the memory 322. If the biometric data supplied by the patient matches the baseline biometric data information stored in the memory 322, the biometric patient identifier 314 successfully identifies the patient and transmits a message to the controller 304 to grant the patient access to the pill dispenser 152. If the biometric data supplied by the patient does not match the baseline biometric data information stored in the memory 322, the biometric patient identifier 314 does not successfully identify the patient and does not transmit a message to the controller 304 to grant the patient access to the pill dispenser 152.

The blood tester 312 comprises a blood analyzer mounted on an exterior surface of the pill dispenser 152 and may be used in conjunction with the biometric patient identifier 314 to identify a patient. A patient may be required to provide a blood sample to be granted access to the pill dispenser 152. For example, the memory 322 may store instructions to require a patient to provide a blood sample at certain intervals throughout the duration of the patient's prescription to ensure the patient has been taking the medication corresponding to the dosing schedule prescribed by the physician. The blood tester 312 tests the patient's blood drug plasma level for traces of the medication and the controller 304 determines whether the patient may be granted access to the pill dispenser 152 based on the test results obtained from the blood tester 312. For example, the controller 304 will grant the patient access to the pill dispenser 152 if the blood drug plasma registers a sufficient reading based on a standard and will not grant the patient access to the pill dispenser 152 if the blood drug plasma level does not achieve a sufficient reading based on the standard.

The blood tester 312 may include a drug plasma level testing component designed to enable a physician and/or pharmacist to compare usage of the medication by testing the patient's blood concentration levels. The drug plasma level testing component compares the levels of medication present in the patient's plasma to acceptable predetermined parameters of medication levels expected in the patient's plasma. The drug plasma level testing component may confirm the patient has been taking the medication as prescribed by the dosage if the medication levels correspond to the acceptable predetermined parameters. The blood testing component may recognize that the patient has not been taking the medication as prescribed and may be diverting the medication to an unauthorized third party if the medication levels do not correspond to the acceptable predetermined parameters. The pill dispenser 152 may transmit a signal via the communications module 308 to at least one of the prescribing physician's office 130 or the pharmacy 140 of the results of the blood testing. The blood testing results provide for a prescribing physician or pharmacy 140 to monitor a patient's use of the medication in real time, and may serve as an early warning sign that a patient is diverting medication if the medication levels do not correspond to the acceptable predetermined parameters.

The lock/unlock mechanism may grant the patient access to the dispensing gate 324 to receive their medication. The patient is granted access to the pill dispenser 152 (e.g., a single chamber of the rotatable pill magazine 326) when the lock/unlock mechanism is set to UNLOCK and the dispensing gate 324 is switched to the OPEN state. The patient is not granted access to the pill dispenser 152 when the mechanism is set to LOCK and the dispensing gate 324 is set to the CLOSED state. The default state of the lock/unlock mechanism is the LOCK state such that the patient may be restricted from accessing the pill dispenser 152 outside of the specified time period and/or location in which they may receive their medication.

The tampering detection mechanism detects if the pill dispenser 152 is being tampered with. For example, a patient may attempt to tamper with the pill dispenser 152 to access the medication inside. Tampering may include, but is not limited to, hitting the pill dispenser 152, throwing the pill dispenser 152 or otherwise attempting to break apart the pill dispenser 152. The tampering detection mechanism may comprise a continuous conductive metal interior lining underlying the outer wall of the pill dispenser 152. An attempt to tamper with the pill dispenser 152, i.e. gain access to the medication within the pill dispenser 152, will damage the conductive metal interior lining. The damage alerts the controller 304 to lock the dispensing gate 324. The damage may also alert at least one of the prescribing physician's office 130 and pharmacy 140 of the tampering such that the pill dispenser 152 may require authorization from at least one of the prescribing physician's office 130 and pharmacy 140 to unlock the pill dispenser 152 so the patient can receive their medication.

In addition, the tampering detection mechanism may transmit a "non-tampering" signal to the controller 304 at predetermined time intervals in a default state. For example, the tampering detection mechanism may transmit a "non-tampering" signal to the controller 304 every sixty seconds and as such, the controller 304 recognizes that the pill dispenser 152 has not been tampered with. The conductive metal interior lining may suffer damage that prevents the tampering detection mechanism from transmitting the "non-tampering" signal to the controller 304 when the pill dispenser is being tampered with. Accordingly, the controller 304 recognizes that the pill dispenser 152 may have been tampered with when the controller 304 fails to receive the "non-tampering" signal at the next predetermined time interval and transmits a signal to the lock/unlock mechanism to set to the LOCK position. The controller 304 may also control the communication module 308 to transmit a signal to at least one of the prescribing physician's office 103 and the pharmacy 140 that the pill dispenser 152 has been tampered with.

The power supply 318 provides an electrical current to operate the components of the pill dispenser 152. A battery 316 may also be used as the power supply. In addition, the power supply 318 can include, but is not limited to, a piezoelectric device, a solar power device and a capacitor. The power supply 318 may use electrical current supplied from outside the pill dispenser 152 (e.g., an electrical socket). The pill dispenser 152 may also utilize a power backup switch 320 to maintain power such that the power backup switch 320 outputs direct current (DC) power to allow the pill dispenser 152 to maintain power if the power supply 318 is cut off.

The pill dispenser 152 may contain additional anti-theft measures. For example, the pill dispenser 152 may be constructed so that if the pill dispenser 152 is intentionally broken or destroyed in an attempt by a patient to gain access to the medication within the pill dispenser 152, the medication will also be destroyed by the destruction of the pill dispenser 152. The GPS module 306 may be used to track the location of the pill dispenser 152 in the event the pill dispenser 152 is stolen. In addition, the communication module 308 may transmit a signal notifying at least one of the prescribing physician's office 130 and the pharmacy 140 when the GPS module 306 moves outside of an area authorized by the prescribing physician. For example, the dispensing schedule instructions may include a specified area that the pill dispenser 152 may be permitted to remain in such that a patient may travel between the pharmacy 140 and their residence or work without locking the pill dispenser 152 but otherwise restricting the movement of the pill dispenser 152.

Data from the pill dispenser 152 may be used for patient behavioral analysis. For example, data including medication levels obtained by the blood tester 312, tampering data obtained by the tampering detection mechanism, and access data obtained by the biometric patient identifier 314 may be used alone or in combination by at least one of the prescribing physician's office 130 or the pharmacy 140 to analyze patient behavioral patterns. For example, medication levels obtained by the blood tester 312 may be used to determine whether a patient has been taking the medication as prescribed or whether the dosage level prescribed is proper for the patient. Tampering data may be used to determine whether a patient or an unauthorized third party has attempted to tamper with the pill dispenser 152. Access data obtained by the biometric patient identifier 314 may be used to determine whether the patient attempts to access the pill dispenser 152 at the predetermined time intervals to receive medication, whether the patient attempts to access the pill dispenser 152 outside of the predetermined time intervals, or whether a third party attempts to gain access to the pill dispenser 152.

In addition, the data could be stored in a patient database. The patient database could be continuously updated by messages automatically transmitted by the pill dispenser 152 to the patient database each time a patient attempts to access the medication stored within the pill dispenser 152 both in compliance with his or her prescription and otherwise. The patient database could be stored on the network control center server 124a of the operations center 120 or could be resident in a secure cloud storage facility (e.g, cloud-based) such as Dropbox Business; Egnyte Business; Amazon S3; and Microsoft OneDrive for Business.

The patient database could be accessible to medical providers (e.g., the prescribing physician's office 130 or the pharmacy 140) and operations center administrators to facilitate securely dispensing medication to the patient using the pill dispenser 152 and for mitigating the risk of diversion of the medication to an unauthorized user. The patient database could also be accessible to third parties (e.g., researchers) with the purchase of a license wherein access to the patient database and patient data therein would be in compliance with HIPAA regulations.

The pharmacy 140 includes a communication module 146 having a WI-FI module, a pharmacist computer 142 and a dosing and dispensing database 144. The communication module 146 transmits and receives signals to and from the other devices in the network 300. The dosing and dispensing database 144 includes information relating to a patient and the dosage and dispensing information relating to their medication. The pharmacist computer 142 may comprise computer software configured to maintain records of the pill dispenser 152 and corresponding patient identification, remotely unlock the pill dispenser 152 and track the location of the pill dispenser via the GPS module 306 of the pill dispenser 152. The computer software may also enable the input of custom dosing schedules to dispense the medication.

The prescribing physician's office 130 includes a communication module (not shown), a physician computer 132 and a patient database 134. The communication module transmits and receives signals to and from the other devices in the network 300. The patient database includes information on each of the physician's patients and may comprise records of what medication a patient was prescribed, when the medication was prescribed to the patient, and the dosage of the medication.

The physician computer 132 may be a personal computer (PC) used by the physician and may comprise computer software. The computer software may contain generate information including, but not limited to, records of interaction between the patient and the pill dispenser 152; records of patient compliance with medication dosing schedules; a serial number decoding system to correlate a pill dispenser 152 with a patient; a decoding system for pill dispenser 152 tampering alerts; records of indications of a patient diverting medication to third parties; an alert function to accept incoming pill dispenser 152 tampering alerts; a password protected alert notification system; and location logs of the GPS module 306.

Although FIG. 5 illustrates one example of a network 300, the network 300 could include any number of each component in any suitable arrangement, and as such FIG. 5 does not limit the scope of the present disclosure to any particular configuration.

Figure 6:
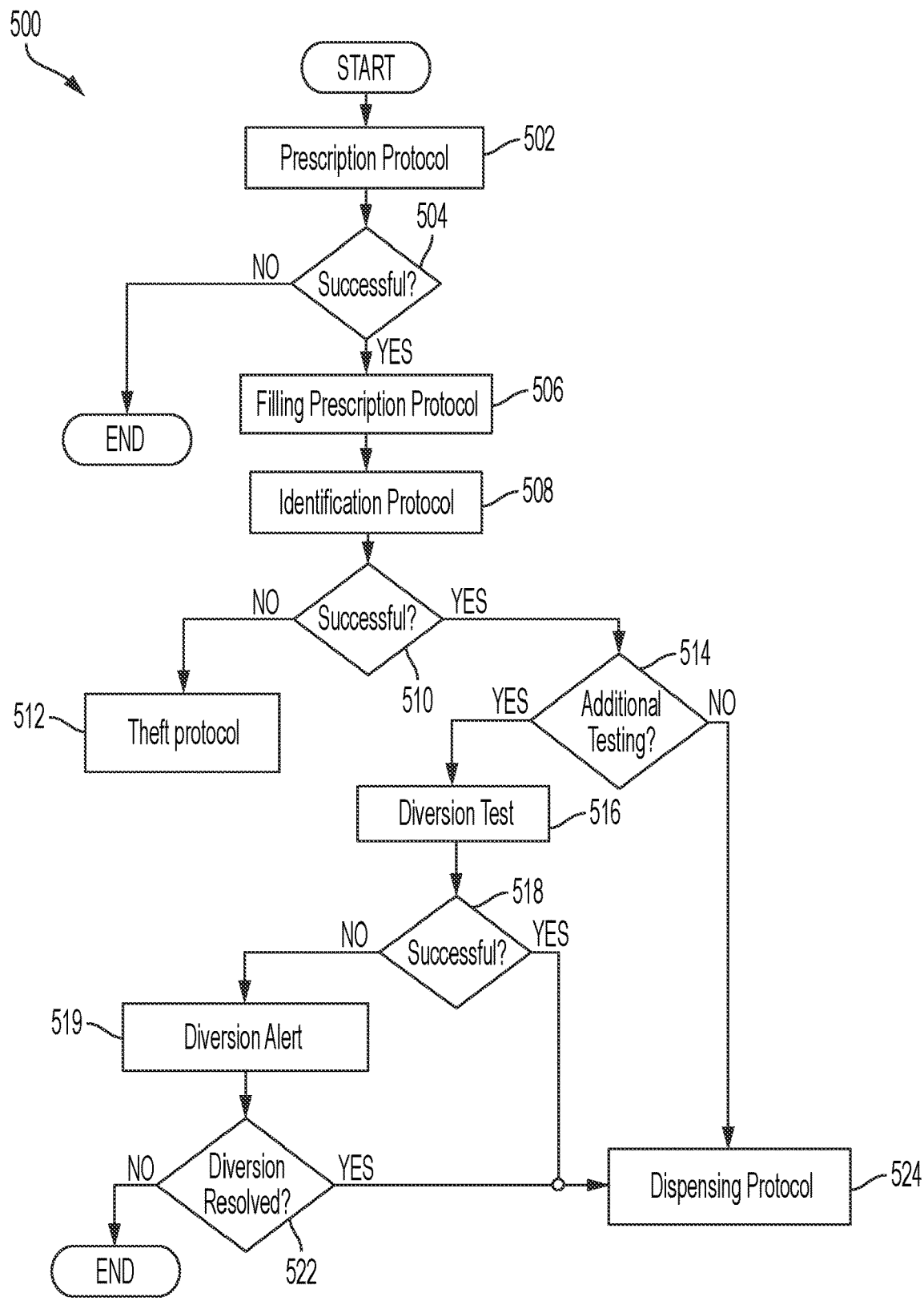
FIG. 6 is a flowchart illustrating processing steps carried out by the system of the present disclosure.

FIG. 6 is a flowchart illustrating processing steps carried out by the system of the present disclosure. The system 500 of the present disclosure provides for securely dispensing medication to a patient using a secure, programmable medication dispenser and mitigating the risk of diversion of medication to an unauthorized user.

Beginning in step 502, the system 500 enters a prescription protocol. During the prescription protocol a prescribing physician 130 prescribes a patient a medication and the patient submits the prescription to a pharmacy 140 for validation. For example, the patient identifies himself or herself to the pharmacy 140 and the pharmacy 140 attempts to retrieve the prescription from the pharmacy database resident in cloud storage. Then, in step 504, the system 500 determines whether the prescription protocol is successful (i.e., whether the pharmacy 140 can retrieve the electronic prescription). The process ends if the prescription protocol is not successful. Alternatively, the system 500 enters a filling prescription protocol 506 if the prescription protocol is successful. During the filling prescription protocol, the pharmacy 140 issues the patient a pill dispenser 152 filled with the prescribed medication.

In step 508, the patient attempts to access the pill dispenser 152 to take the prescribed medication by verifying his or her identity during the identification protocol. Then, in step 510, the system 500 determines whether the identification protocol is successful. If the identification protocol is unsuccessful, the system 500 enters the theft protocol in step 512 and the controller 304 alerts at least one of the operations center, the prescribing physician's office 130 and the pharmacy 140 of the theft and initiates a lockdown of the pill dispenser 152. Alternatively, the system 500 determines whether additional testing is necessary in step 514 if the identification protocol is successful.

The system 500 proceeds to step 524 and initiates the dispensing protocol if the system 500 determines additional testing is not necessary. During the dispensing protocol the patient is granted access to the pill dispenser 152 and the medication is dispensed from the pill dispenser 152 to the patient. Alternatively, the system 500 proceeds to step 516 and executes a diversion test if the system 500 determines additional testing is necessary. During the diversion test the system 500 determines whether the patient is diverting the prescribed medication to an unauthorized user.

In step 518, the system 500 determines whether the diversion test is successful. The system 500 proceeds to step 524 and initiates the dispensing protocol if the system 500 determines the diversion test is successful. During the dispensing protocol the patient is granted access to the pill dispenser 152 and the medication is dispensed from the pill dispenser 152 to the patient. Alternatively, the system proceeds to step 519 and transmits a diversion alert if the system 500 determines the diversion test is unsuccessful. Then, in step 522, the system 500 determines whether the diversion alert has been resolved. For example, if the system determines the patient intentionally attempted to divert medication from the pill dispenser 152 to an unauthorized user in step 522 then the process ends. However, if the system 500 determines that the patient unintentionally triggered the diversion alert and/or that the pill dispenser 152 malfunctioned, then the system 500 proceeds to step 524 and initiates the dispensing protocol. During the dispensing protocol the patient is granted access to the pill dispenser 152 and the medication is dispensed from the pill dispenser 152 to the patient.

Figure 7:
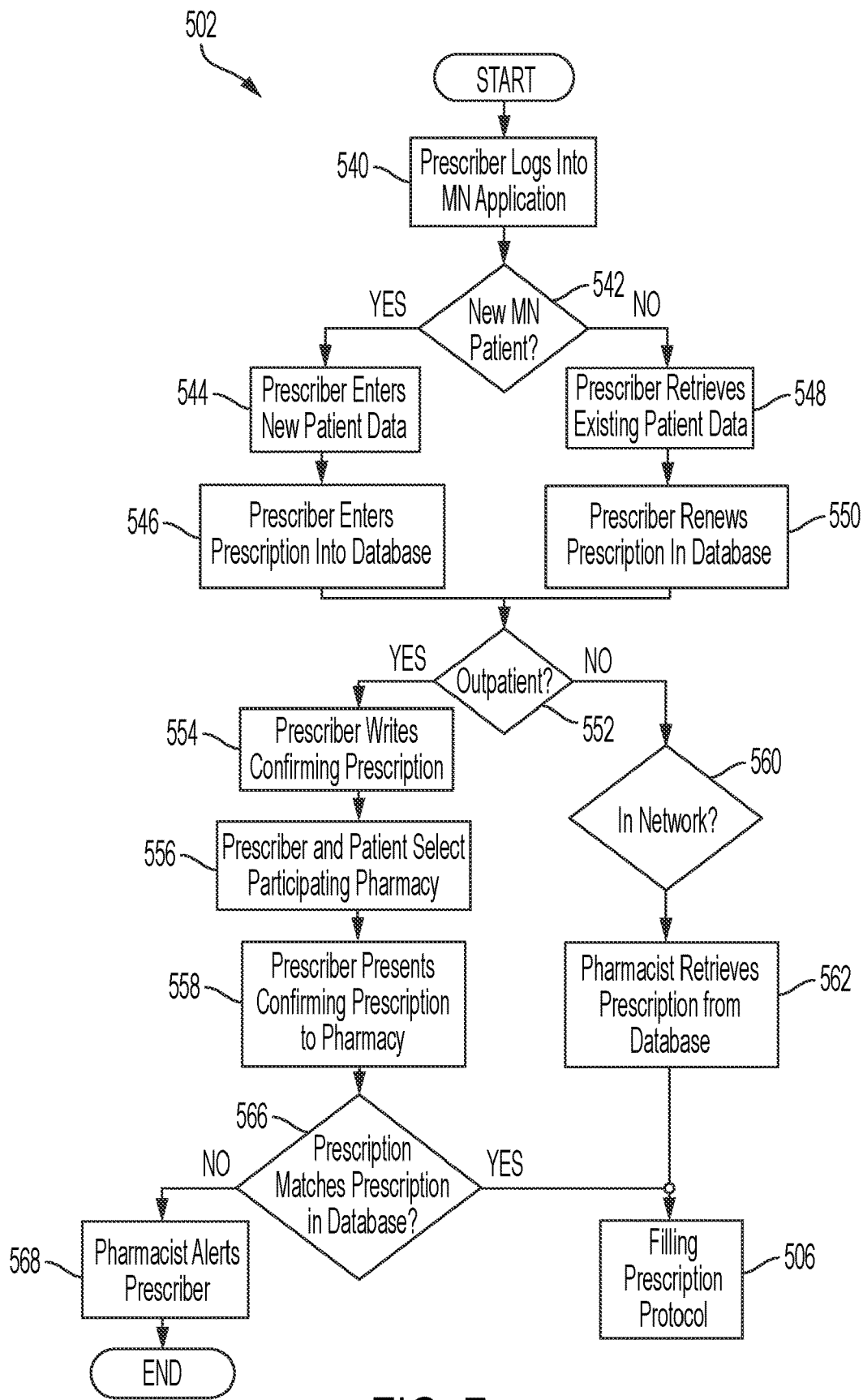
FIG. 7 is a flowchart illustrating step 502 of FIG. 6 in greater detail.

FIG. 7 is a flowchart illustrating step 502 of FIG. 6 in greater detail. Step 502 comprises the prescription protocol during which a prescribing physician 130 prescribes a patient a medication and the patient submits the prescription to a pharmacy 140 for validation. Beginning in step 540, the prescribing physician 130 logs into a subscription application. In step 542, the prescribing physician 130 determines whether the patient's identifying information and relevant data (e.g., medical history) are stored in a database of the subscription application. Then, in step 544, the prescribing physician 130 enters the patient's identifying information and relevant data into the subscription application database if the patient is new. Further, in step 546, the prescribing physician 130 enters the patient's prescription into the database of the subscription application. Alternatively, in step 548, the prescribing physician 130 retrieves the patients identifying information and relevant data if the patient is an existing patient. Further, in step 550, the prescribing physician 130 renews the patient's prescription in the database of the subscription application.

In step 552, the prescribing physician 130 determines whether the patient is an outpatient. In step 554, the prescribing physician 130 writes a confirming prescription if the prescribing physician 130 determines the patient is an outpatient. Further in step 556, the prescribing physician 130 and the patient select a pharmacy 140 to fill the prescription and in step 558 the patient presents the confirming prescription to the pharmacy 140. Then, in step 566, the pharmacy 140 determines whether the confirming prescription matches the prescription in the subscription application database. In step 568, the pharmacy 140 alerts the prescribing physician 130 if the pharmacy 140 determines that the confirming prescription and the prescription in the subscription application database do not match. Alternatively, in step 506, the pharmacy initiates the filling prescription protocol if the pharmacy 140 determines that the confirming prescription and the prescription in the subscription application database match. During the filling prescription protocol, the pharmacy 140 issues the patient a pill dispenser 152 filled with the prescribed medication. As such, the prescribing physician 130 may responsibly and accurately prescribe the patient medication without under prescribing the patient for fear of diversion of the prescribed medication.

In step 560, the prescribing physician 130 determines whether the patient is in network if the prescribing physician 130 determines in step 552 that the patient is not an outpatient. An in network patient (i.e., a patient that subscribes to a health maintenance network), prescriptions can be delivered through the network's supply chain, which can include mail order delivery. Then, in step 562, the pharmacist 562 retrieves the prescription from the subscription application database. In step 506, the pharmacy initiates the filling prescription protocol. During the filling prescription protocol, the pharmacy 140 issues the patient a pill dispenser 152 filled with the prescribed medication. As such, the prescribing physician 130 may responsibly and accurately prescribe the patient medication without under prescribing the patient for fear of diversion of the prescribed medication.

Figure 8:
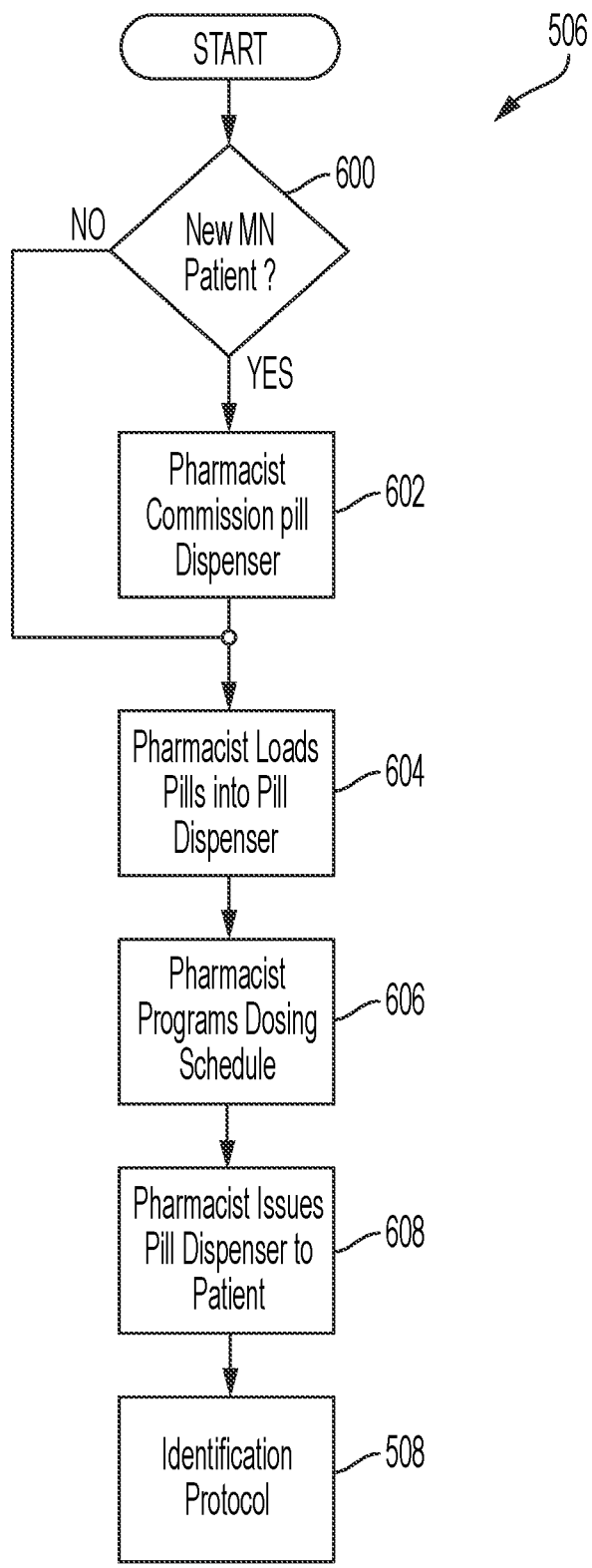
FIG. 8 is a flowchart illustrating step 506 of FIG. 6 in greater detail.

FIG. 8 is a flowchart illustrating step 506 of FIG. 6 in greater detail. Step 506 comprises the filling prescription protocol. During the filling prescription protocol, the pharmacy 140 issues the patient a pill dispenser 152 filled with the prescribed medication. Beginning in step 600, the pharmacy determines whether the patient's identifying information and relevant data (e.g., medical history) are stored in the database of the subscription application. Based on the determination, the pharmacy 140 determines whether to commission a new pill dispenser 152 and associate the new pill dispenser 152 with the patient or fill an existing pill dispenser 152 associated with the patient. For example, the pharmacy 140 commissions the new pill dispenser 152 in step 602, if the pharmacy 140 determines that the patient's identifying information and relevant data are not stored in the database of the subscription application. Alternatively, in step 604, the pharmacy 140 loads the medication into an existing pill dispenser 152 associated with the patient if the pharmacy 140 determines that the patient's identifying information and relevant data are stored in the database of the subscription application.

In step 606, the pharmacy 140 programs the pill dispenser 152 according to the prescribed dosing schedule. Then, in step 608, the pharmacy 140 issues the pill dispenser to the patient. Thereafter, in step 508, the process proceeds to the identification protocol.

Figure 9:
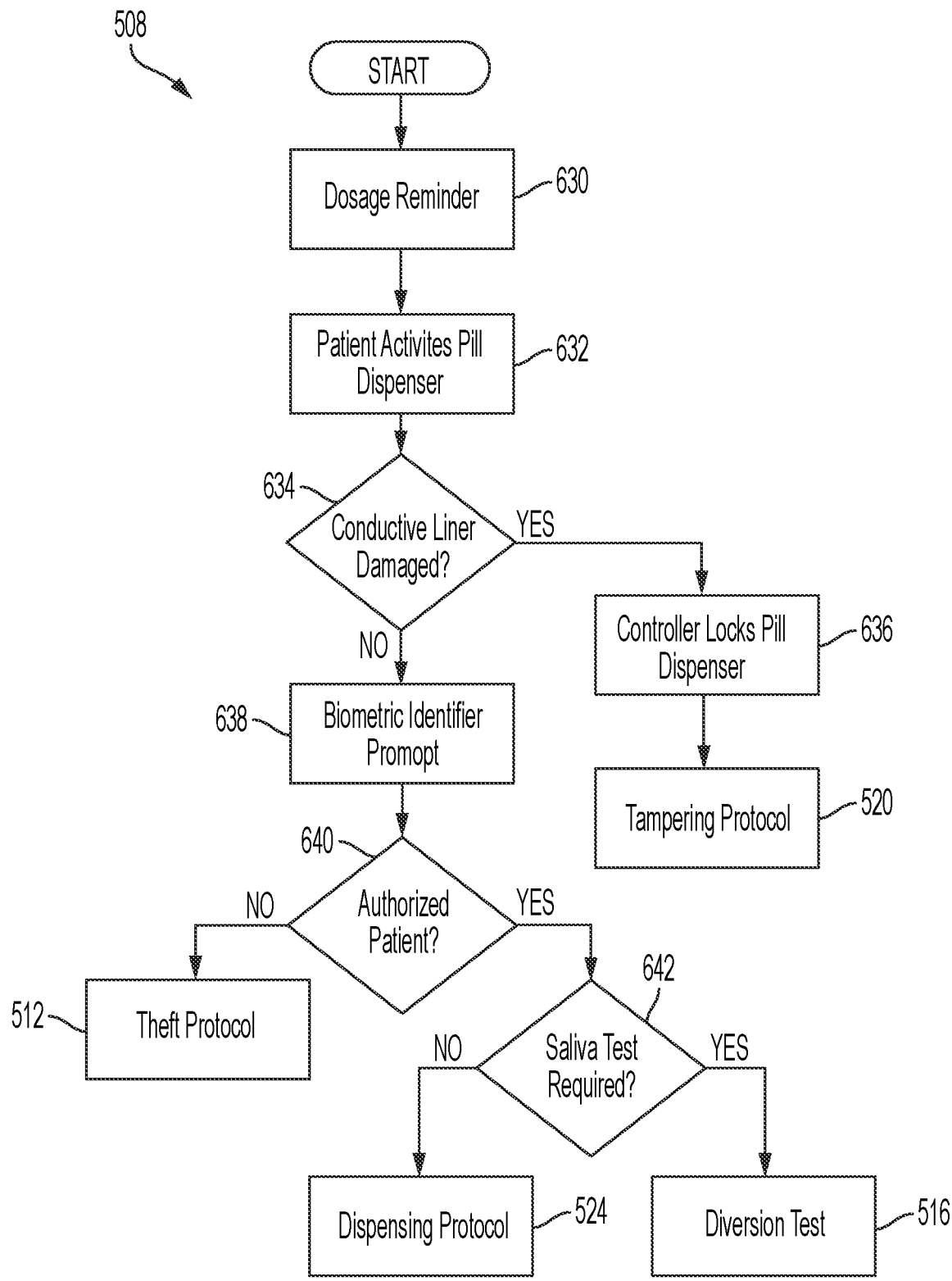
FIG. 9 is a flowchart illustrating step 508 of FIG. 6 in greater detail.

FIG. 9 is a flowchart illustrating step 508 of FIG. 6 in greater detail. Step 508 comprises the identification protocol. During the identification protocol, the patient attempts to access the pill dispenser 152 to take a scheduled dose of the prescribed medication by verifying his or her identity. Beginning in step 630, the pill dispenser 152 notifies the patient via a reminder or alert to take a dosage of the prescribed medication. The reminder or alert can include flashing light emitting diodes (LEDs) on an exterior surface of the pill dispenser 152 and/or sound. In step 632, the patient activates the pill dispenser 152 to attempt to access the medication within the pill dispenser 152. Then, in step 634, the pill dispenser 152 determines whether the conductive liner along the interior of the pill dispenser 152 is damaged.

The controller 304 locks the pill dispenser 152 in step 636 if the pill dispenser 152 determines the conductive liner along the interior of the pill dispenser 152 is damaged. Subsequently, the pill dispenser 152 enters the tampering protocol in step 520. Alternatively, the pill dispenser 152 prompts the patient to verify his or her identity via the biometric identifier in step 638 if the pill dispenser 152 determined the conductive liner is not damaged. The pharmacy 140 can conduct a baseline biometric test on the patient and store the results in the memory of the controller 304 of the pill dispenser 152 when the pill dispenser 152 is originally issued to the patient. The controller 304 of the pill dispenser 152 will only unlock the dispensing gate 324 when the biometric test data matches the stored data. Accordingly, in step 640, the pill dispenser 152 determines whether the patient is authorized to access the scheduled dose of the prescribed medication from the pill dispenser 152. In step 512, the pill dispenser enters the theft protocol if the patient is unauthorized to access the scheduled does of the prescribed medication. Alternatively, the process proceeds to step 642 to determine whether a saliva test is required if the pill dispenser 152 determines the patient is authorized to access the scheduled dose of the prescribed medication from the pill dispenser 152. Specifically, at predetermined intervals selected by the prescribing physician 130 and programmed into the pill dispenser 152, the patient may be required to deposit a saliva sample onto the saliva sampling module. The level of the prescribed medication in the patient's bloodstream may determined by the module's analysis of the saliva sample and is a reliable indicator of the patient's compliance with the prescribed dosing schedule. The saliva sampling module performs the analysis of the saliva sample according to an algorithm built into the controller 304 that accounts for physical characteristics of a patient including, but not limited to, age and gender.

In step 524, the process proceeds to the dispensing protocol if the pill dispenser 152 determines that a saliva test in not required. During the dispensing protocol the patient is granted access to the pill dispenser 152 and the medication is dispensed from the pill dispenser 152 to the patient. Alternatively, the process proceeds to step 516 and executes a diversion test if the pill dispenser 15 determines the saliva test is required. During the diversion test, the pill dispenser 152 determines whether the patient is diverting the prescribed medication to an unauthorized user.

Figure 10:
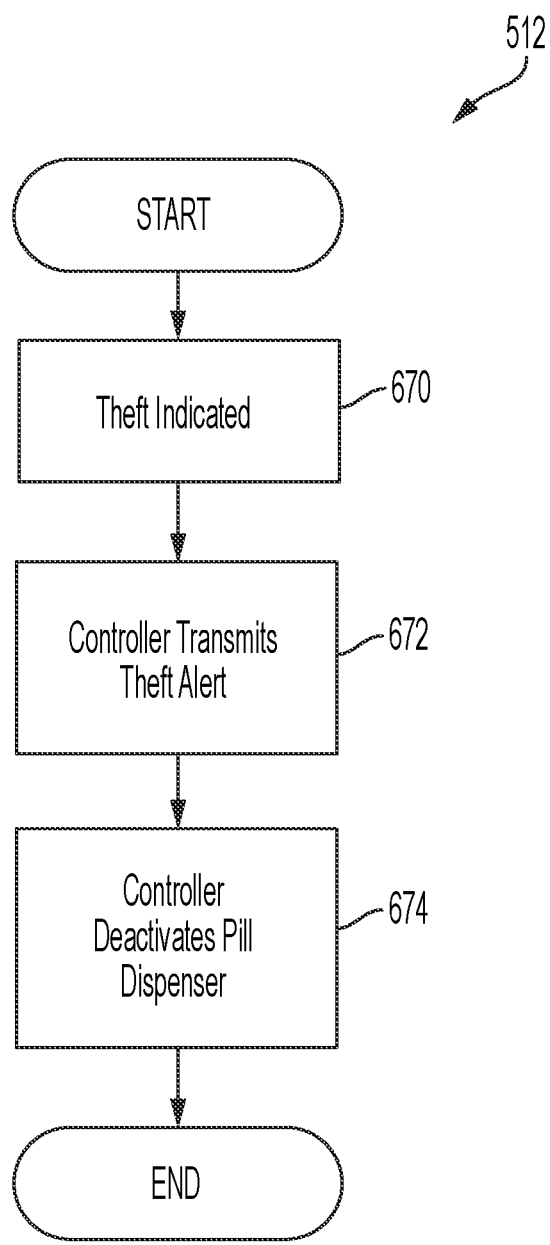
FIG. 10 is a flowchart illustrating step 512 of FIG. 6 in greater detail.

FIG. 10 is a flowchart illustrating step 512 of FIG. 6 in greater detail. Step 512 comprises the theft protocol. Beginning in step 670, the pill dispenser 152 detects a theft. As mentioned above, the pill dispenser 152 includes a GPS module 306 to facilitate a pill dispenser's retrieval (if lost) or deactivation (if stolen). Specifically, when a theft is indicated, the controller 304 transmits a theft alert in step 672 to patient services 122c. In turn, patient services 122c may remotely activate the GPS module 306 to determine whether the pill dispenser 152 has been stolen. In step 674, patient services 122c determines the pill dispenser 152 has been stolen and remotely deactivates the pill dispenser 152 via the controller 304. Patient services 122c may also initiate a retrieval protocol to retrieve the pill dispenser 152 if patient services 122c determines the pill dispenser 152 is lost.

Figure 11:
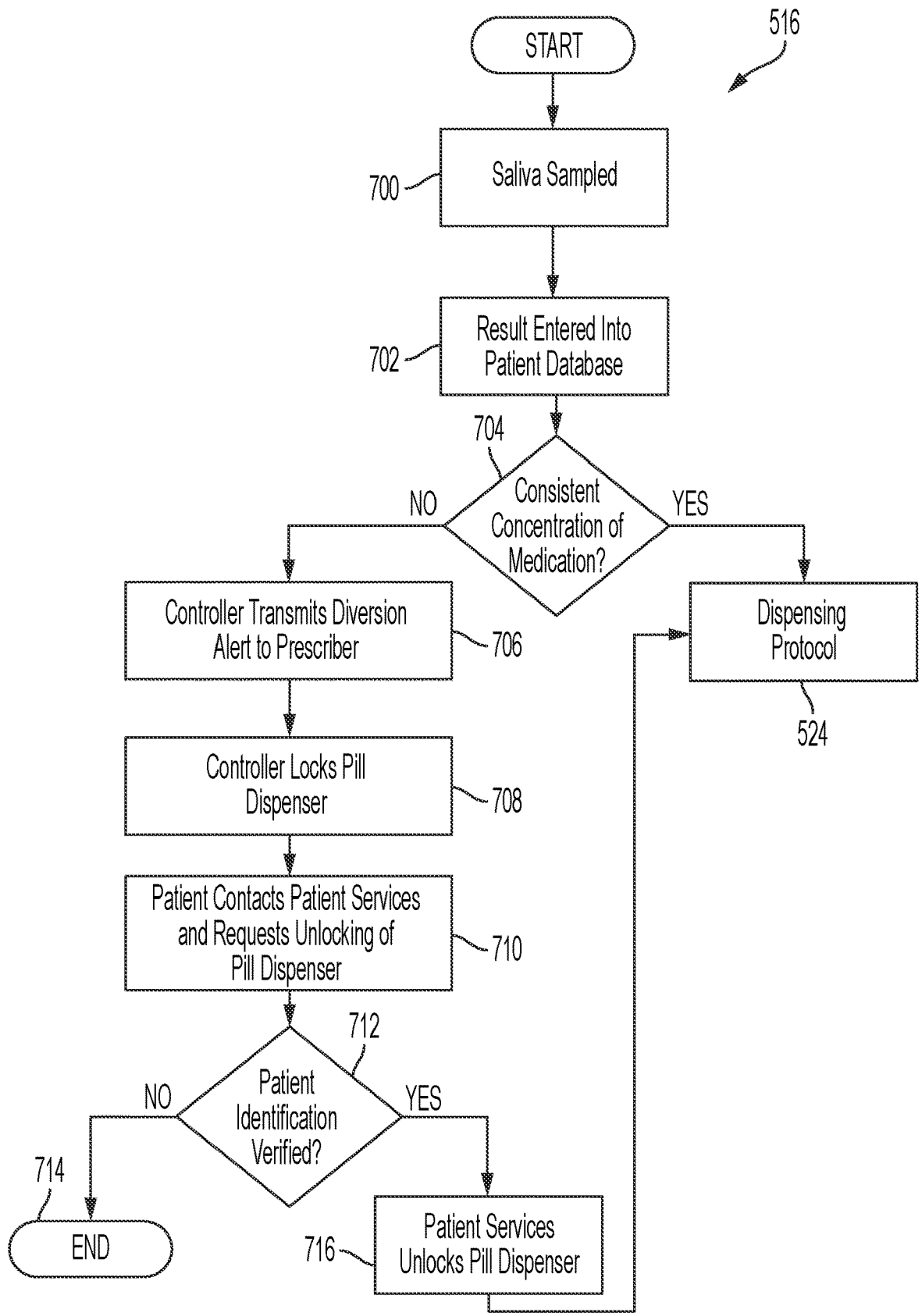
FIG. 11 is a flowchart illustrating step 516 of FIG. 6 in greater detail.

FIG. 11 is a flowchart illustrating step 516 of FIG. 6 in greater detail. Step 516 comprises the diversion test. During the diversion test the system 500 determines whether the patient is diverting the prescribed medication to an unauthorized user. Generally, in the event a patient has been removing medication from the pill dispenser 152 according to the prescribed dosing schedule but the saliva sampling module determines that the level of the prescribed medication in the patient's bloodstream is inconsistent with the prescribed dosing schedule, the controller 304 will disable the dispensing gate 324 and transmits a diversion alert to the prescribing physician 130.

Beginning in step 700, the saliva sampling module samples a patient's saliva. The level of the prescribed medication in the patient's bloodstream may be determined by the module's analysis of the saliva sample (e.g., NarcoCheck®) compared with a standardized control and is a reliable indicator of the patient's compliance with the prescribed dosing schedule. The saliva sampling module performs the analysis of the saliva sample according to an algorithm built into the controller 304 that accounts for physical characteristics of a patient including, but not limited to, age and gender. Subsequently, in step 702, the saliva sample module result is entered into a patient database.

Then, in step 704, the system 500 determines whether the result is consistent with the patient's prescribed dosing schedule. The process proceeds to the dispensing protocol in step 524 if the result is consistent with the patient's prescribed dosing schedule. During the dispensing protocol the patient is granted access to the pill dispenser 152 and the medication is dispensed from the pill dispenser 152 to the patient. Alternatively, in step 706 the controller 304 transmits a diversion alert to the prescribing physician 130 if the result is inconsistent with the patient's prescribed dosing schedule. Then, in step 708 the controller 304 locks the dispensing gate 324 of the pill dispenser 152. In step 710 the patient contacts patient services 122c and requests that the pill dispenser 152 be unlocked. Then, in step 712, patient services 122c gathers patient identifying information and verifies the identification of the patient. The process ends in step 714 if patient services 122c cannot verify the identity of the patient in step 712. Alternatively, patient services 122c unlocks the pill dispenser 152 in step 716 and enters the transaction into the patient database if patient services 122c verifies the identity of the patient in step 712. The process then proceeds to the dispensing protocol in step 524.

Figure 12:
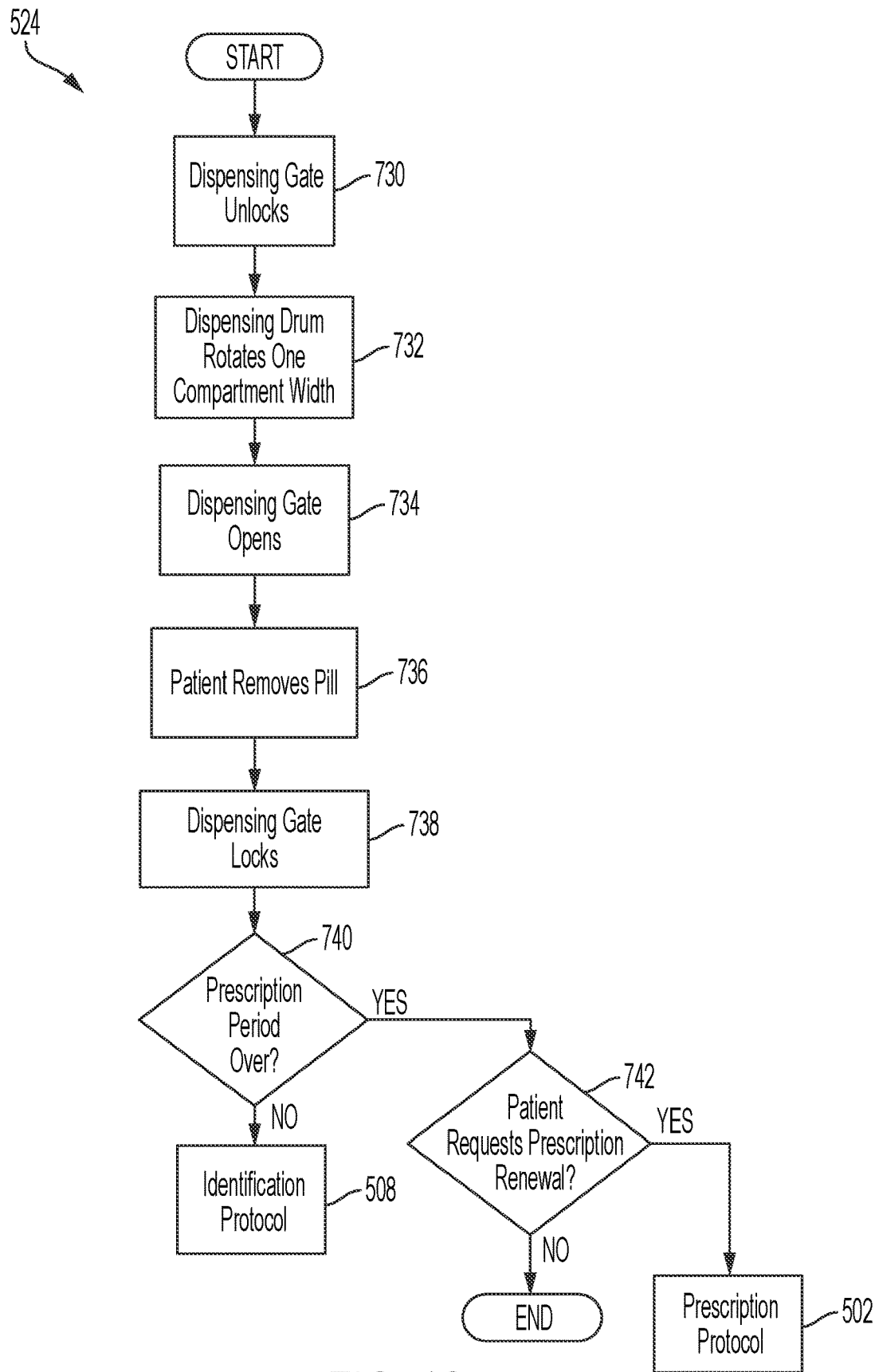
FIG. 12 is a flowchart illustrating step 524 of FIG. 6 in greater detail.

FIG. 12 is a flowchart illustrating step 524 of FIG. 6 in greater detail. Step 524 comprises the dispensing protocol. During the dispensing protocol the patient is granted access to the pill dispenser 152 and the medication is dispensed from the dispensing gate 324 of the pill dispenser 152 to the patient. Beginning in step 730, the controller 304 unlocks the dispensing gate 324. Next, in step 732, the rotatable pill magazine 326 rotates one compartment width. The rotatable pill magazine 326 may have any configuration or shape so long as the size of the rotatable pill magazine 326 provides for the rotation of the rotatable pill magazine 326 about an axis within the housing of the pill dispenser 152. In step 734, the dispensing gate 324 opens and in step 736 the patient may remove the prescribed medication from the pill dispenser 152. Subsequently, in step 738, the controller 304 locks the dispensing gate 324.

In step 740, the controller 304 determines whether the prescription period is over (i.e., whether the rotatable pill magazine 326 of the pill dispenser 152 contains any more medication). In step 742, a patient may request a prescription renewal if the controller 304 determines the prescription period is over. The prescription protocol is initiated in step 502 if the patient requests a prescription renewal. During the prescription protocol, a prescribing physician 130 prescribes the patient a medication and the patient submits the prescription to a pharmacy 140 for validation. Otherwise the process ends if the patient does not request a prescription renewal.

Alternatively, the controller 304 determines whether the patient may receive another dose of medication according to the prescribed dosing schedule if the controller 304 determines the prescription period is not over. The process proceeds to the identification protocol in step 508 if the controller 304 determines the patient may receive another dose of medication according to the prescribed dosing schedule. During the identification protocol the patient attempts to access the pill dispenser 152 to take the prescribed medication by verifying his or her identity. Otherwise, the process ends if the controller 304 determines the patient may not receive another dose of medication according to the prescribed dosing schedule.

Figure 13:
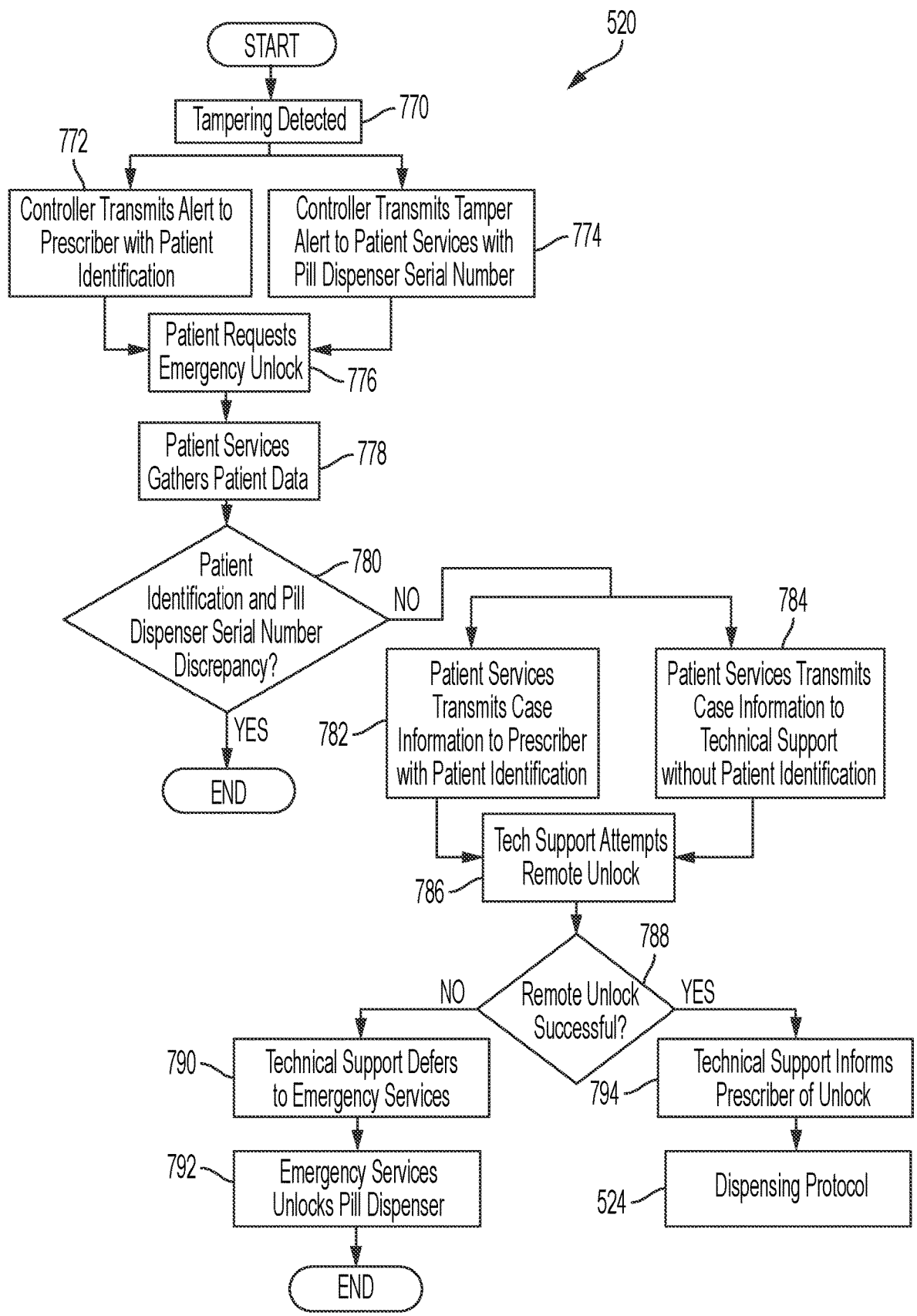
FIG. 13 is a flowchart illustrating step 520 of FIG. 9 in greater detail.

FIG. 13 is a flowchart illustrating step 520 of FIG. 6 in greater detail. Step 520 comprises the tampering protocol. During the tampering protocol, the system 500 determines whether the patient has tampered with the pill dispenser 152 by improperly attempting to access the prescribed medication within the pill dispenser 152.

Generally, the pill dispenser 152 will enter a lockdown state when the pill dispenser 152 detects tampering. In the lockdown state, the pill dispenser 152 will transmit concurrent alerts to each of the prescribing physician 130 and patient services 122c. The alert transmitted to the prescribing physician 130 includes the patient identification information, the pill dispenser 152 serial number and the cause of the alert whereas the alert transmitted to patient services 122c may only include the pill dispenser 152 serial number. To unlock the pill dispenser 152, the patient is required to contact patient services 122c and a record of the interaction between the patient and patient services 122c is generated, recorded in the patient database and forwarded to the prescribing physician 130.

Beginning in step 770, the pill dispenser 152 detects tampering and enters a lockdown state. Subsequently, in step 772, the pill dispenser 152 transmits an alert including patient identification information, the pill dispenser 152 serial number and the cause of the alert to the prescribing physician 152. In addition, in step 774, the pill dispenser 152 transmits an alert including the pill dispenser 152 serial number to patient services 122c. Then, in step 776, the patient contacts patient services 122c and requests that the pill dispenser 152 be unlocked. In step 778, patient services 122c requests and gathers identifying information from the patient to verify the patient's identity. For example, patient services 122c may request the patient's name and social security number and permission to match the same to the pill dispenser 152 serial number. A record of the interaction between the patient and patient services 122c is generated, recorded in the patient database and forwarded to the prescribing physician 130.

In step 780, patient services 122c determines whether a discrepancy exists between the identifying information provided by the patient and the pill dispenser 152 serial number. The process ends if the patient services 122c determines a discrepancy exists. In the event a discrepancy exists, patient services may execute a series of steps to retrieve the pill dispenser 152. Alternatively, in step 782, patient services 122c transmits the case information and patient identifying information to the prescribing physician 130 if patient services 122c determines a discrepancy does not exist between the identifying information provided by the patient and the pill dispenser 152 serial number. In addition, in step 784, patient services 122c transmits the case information without the patient identifying information to the technical support center 122a if patient services 122c determines a discrepancy does not exist between the identifying information provided by the patient and the pill dispenser 152 serial number. Subsequently, the technical support center 122a attempts to remotely unlock the pill dispenser 152 in step 786.

In step 788, it is determined whether the attempt to remotely unlock the pill dispenser 152 is successful. Next, in step 790, the technical support center 122a defers to the emergency field services offices 170 to unlock the pill dispenser 152 if the attempt to remotely unlock the pill dispenser 152 is unsuccessful. In step 792, the emergency field services offices 170 unlocks the pill dispenser 152 and the process ends.

Alternatively, the technical support center 122a notifies the prescribing physician 130 in step 794 if the attempt to remotely unlock the pill dispenser 152 is successful and then the process proceeds to the dispensing protocol in step 524. During the dispensing protocol the patient is granted access to the pill dispenser 152 and the medication may be dispensed from the dispensing gate 324 of the pill dispenser 152 to the patient.

Figure 14:
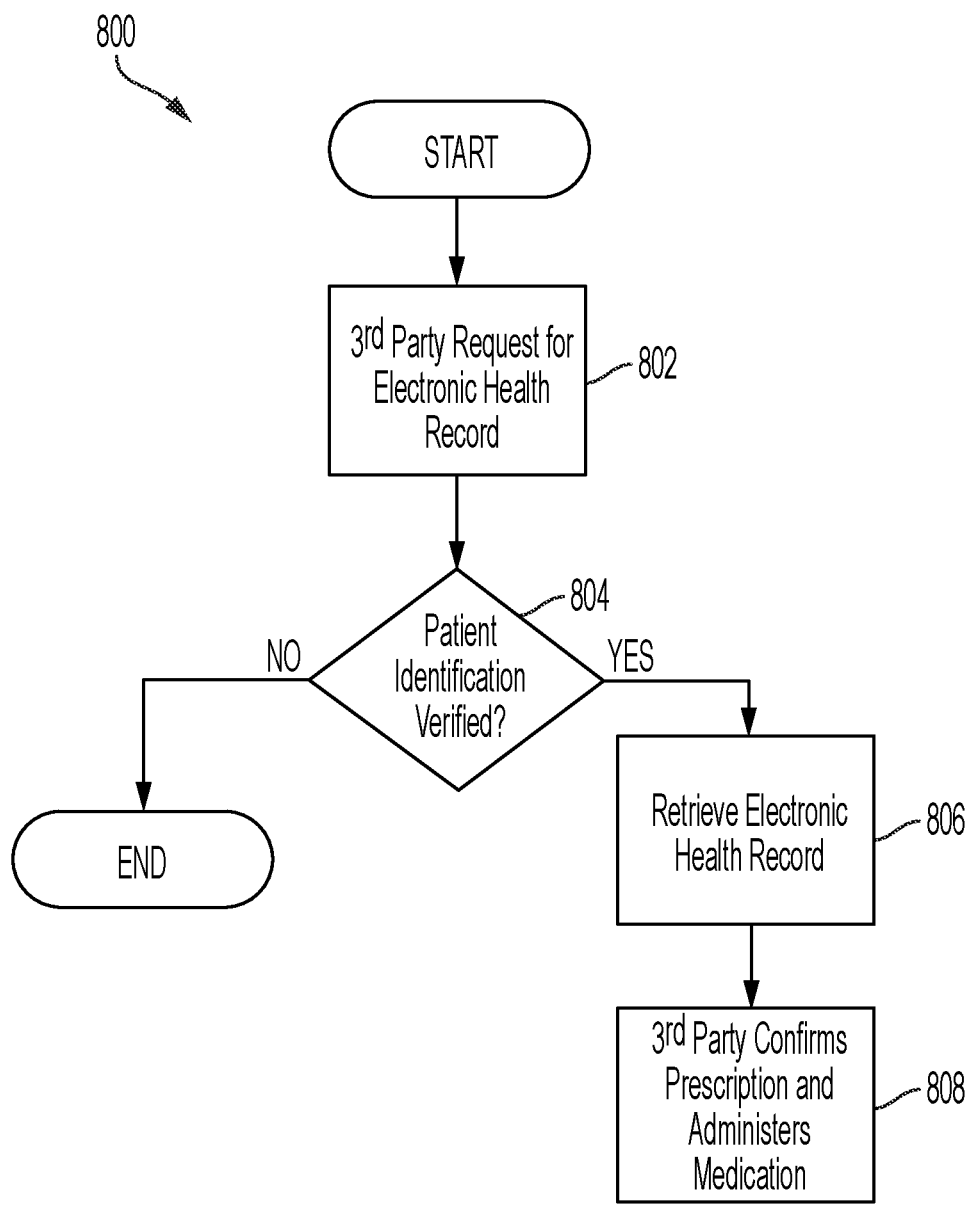
FIG. 14 is a flowchart illustrating processing steps carried out by a third party requesting an electronic health record.

FIG. 14 is a flowchart illustrating processing steps carried out by a third party (e.g., a hospital) requesting an electronic health record. Beginning in step 802, a third party issues a request for a patient's electronic health record to the help center 122. For example, the third party may issue a request to patient services 122c. In step 804, patient services may request and gather identifying information from the patient to verify the patient's identity. For example, patient services 122c may request the patient's name and social security number and permission to match the same to the pill dispenser 152 serial number. A record of the interaction between the third party and patient services 122c and the patient and patient services 122c is generated, recorded in the patient database and forwarded to the prescribing physician 130.

The process ends if patient services 122c is unable to verify the patient's identity. For example, the process ends if patient services 122c determines a discrepancy exists between the identifying information provided by the patient and the pill dispenser 152 serial number. Alternatively, the third party may retrieve the patient's electronic health record in step 806 if patient services 122c can verify the patient's identity. Subsequently, in step 808, the third party confirms the patient's prescription upon review of the patient's electronic health record and administers the prescribed medication. The third party could administer a single dose of the prescribed medication or could execute a filling prescription protocol.

Figure 15:
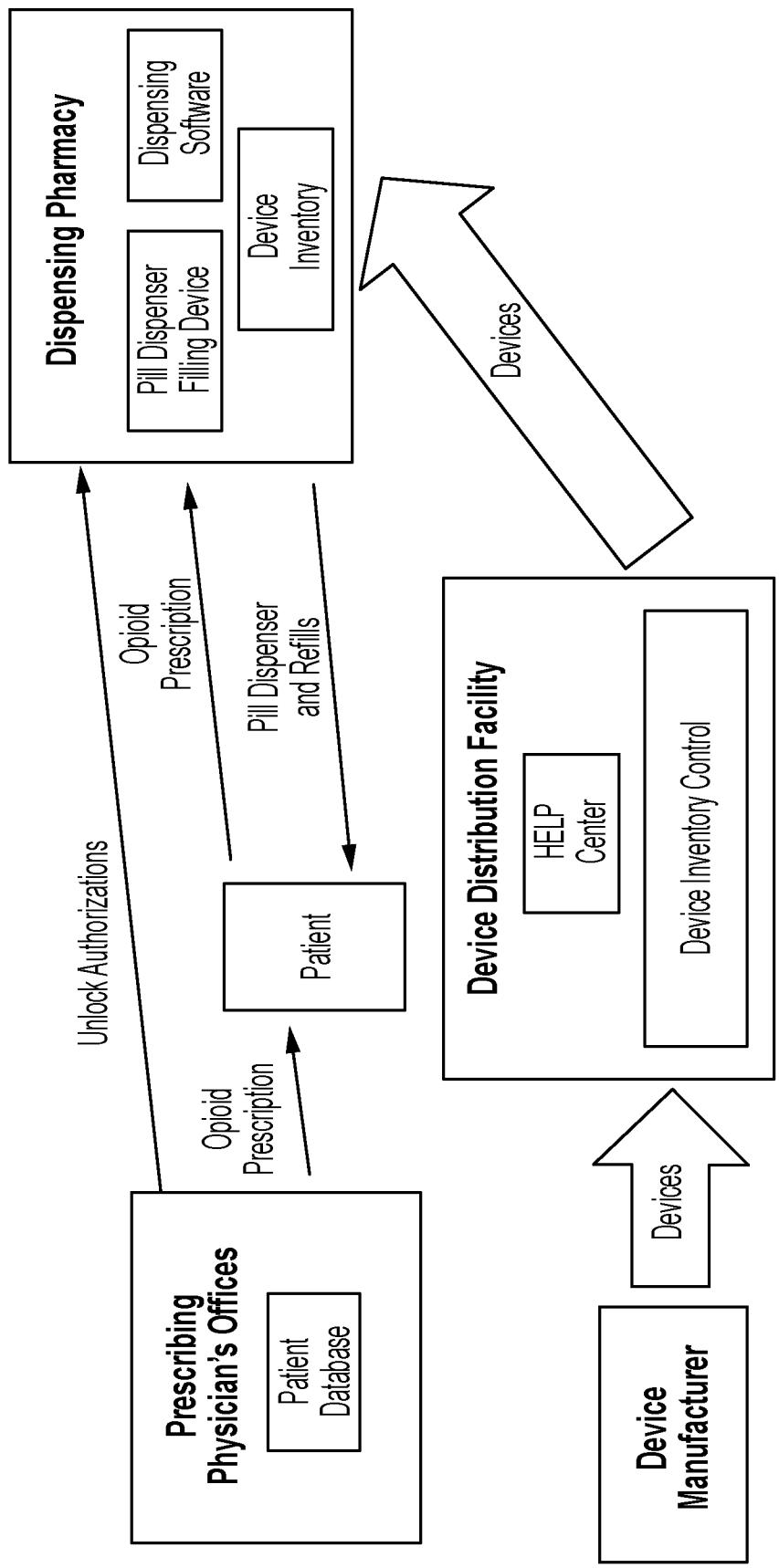
FIG. 15 is a diagram illustrating an example process flow of the system of the present disclosure.

FIG. 15 is a diagram illustrating an example process flow of the system of the present disclosure. The process may include prescribing physician's office, a patient, a dispensing pharmacy, a device manufacturer, and a device distribution facility. The device manufacturer manufactures the pill dispenser 152 and upon manufacture, the pill dispenser 152 is transported to the device distribution facility.

In the device distribution facility, the pill dispenser 152 is sorted and logged in inventory. The pill dispenser remains in the device distribution facility until it is dispensed to a dispensing pharmacy. The device distribution facility may further include a help center that offers support to the distribution network. The help center may also provide pill dispenser 152 support. For example, the help center may support the pill dispenser 152 by at least one of device functionality; device operation; location services; ordering a device; returning a device, and installing or updating software and/or firmware for a device. The help center may distribute software and/or firmware for the pill dispenser 152 or components of a private network.

The pill dispenser 152 is placed in inventory at the pharmacy upon receipt at the pharmacy. Authorized pharmacy personnel may install the software and/or firmware required for operability and functionality of the pill dispenser 152 (e.g., to connect to a network) if the manufacturer did not install the software and/or firmware on the pill dispenser 152 before shipment to the pharmacy. Once the software and/or firmware is installed on the pill dispenser 152, the pill dispenser 152 may be returned to inventory in preparation for being distributed to a patient.

The prescribing physician's office may comprise a patient database. The patient database includes information of patients that visit a physician at the physician's office. The information may include, but is not limited to, a patient's name, contact information, medical history, prescription history, and dosing schedule. The physician's prescription may include a prescription for the pill dispenser 152 if the patient is prescribed a medication that may be addictive, for example an opioid, or the patient is known to have a history of addiction. The patient may submit the prescription to the dispensing pharmacy to be filled or the prescribing physician's office may transmit the prescription directly to the dispensing pharmacy.

The pharmacist or other authorized pharmacy personnel removes the pill dispenser 152 from the device inventory when the dispensing pharmacy receives the prescription. The pharmacist or other authorized pharmacy personnel may use a pill dispensing filling device to load the pill dispenser 152 with the prescribed medication. The pill dispensing filling device may load a predetermined amount of medication into drums of the pill dispenser 152 and then loads the drums into a drum magazine of the pill dispenser 152. The pill dispensing filling device may also fill each chamber of each drum individually.

In addition, the pharmacist or other authorized pharmacy personnel further loads dispensing instructions according to the prescribed dosing schedule onto the memory of the pill dispenser 152. The dispensing instructions may include, but is not limited to, information describing what time(s) of the day to authorize dispensing of the medication, the quantity of medication to dispense at a time or other information. The pill dispenser 152 is issued to the patient after the pill dispenser 152 is loaded with the medication and dispensing instructions. At the time the pill dispenser 152 is issued to the patient, the pill dispenser 152 information (e.g., the serial number) is logged into a database.

Several U.S. states currently restrict the prescription of opioids. For example, at the time of the present disclosure, New Jersey restricts that a "physician . . . may prescribe a Schedule II controlled dangerous substance for the use of a patient in any quantity which does not exceed a 30-day supply." NJ Rev. Stat. § 45:9-22.19 (2016), incorporated herein by reference. Therefore, the present disclosure restricts the amount of medication to be prescribed in accordance with these laws. In the event that a superseding law is passed regarding the prescription of particular medications, one of ordinary skill in the art would be able to modify the present disclosure in accordance with specific state or national laws.

At the end of a prescription cycle (e.g., thirty days), the patient returns the pill dispenser 152 to the dispensing pharmacy for a refill. The pharmacy may require a new prescription or a renewal of the prescription from the prescribing physician's office before refilling the pill dispenser 152 with medication. Upon receipt of the new prescription from the prescribing physician's office, the dispensing pharmacy repeats the steps of loading the pill dispenser 152 with medication and loading instructions onto the memory of the pill dispenser 152.

The pill dispenser 152 may automatically enter a lockdown state in response to the detection of tampering, an attempt to divert the prescribed medication to an unauthorized user or theft of the pill dispenser 152. The prescribing physician's office may transmit instructions directly to the dispensing pharmacy authorizing the dispensing pharmacy to unlock the pill dispenser 152. The prescribing physician's office may also transmit instructions authorizing the dispensing pharmacy to unlock the pill dispenser 152 in response to a first message from the dispensing pharmacy that an inspection has been completed and the pill dispenser 152 is in satisfactory condition.

It is noted that various changes may be made to FIG. 15. One of ordinary skill in the art would understand that the system flow could include any number of each component in any suitable arrangement, and as such FIG. 15 does not limit the scope of the present disclosure to any particular configuration.

Figure 16:
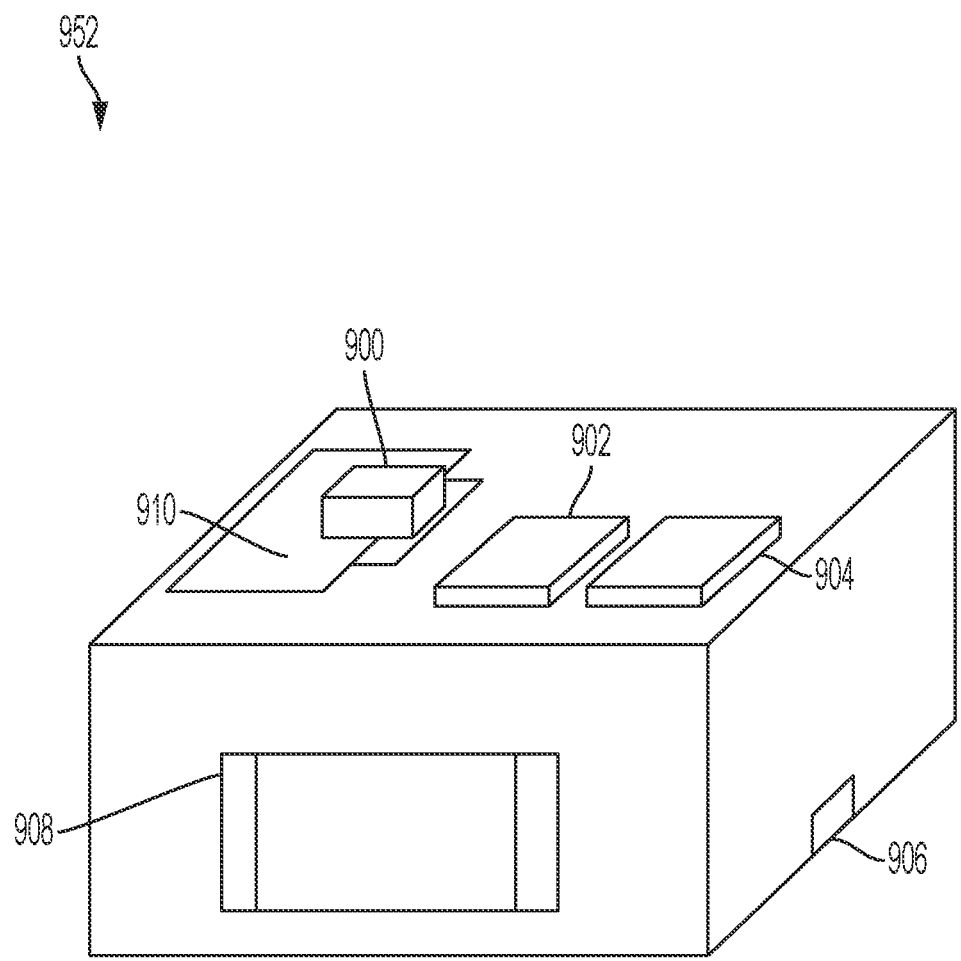
FIG. 16 is a diagram illustrating an exterior view of a device for dispensing medication according to an embodiment of the present disclosure.
Figure 17:
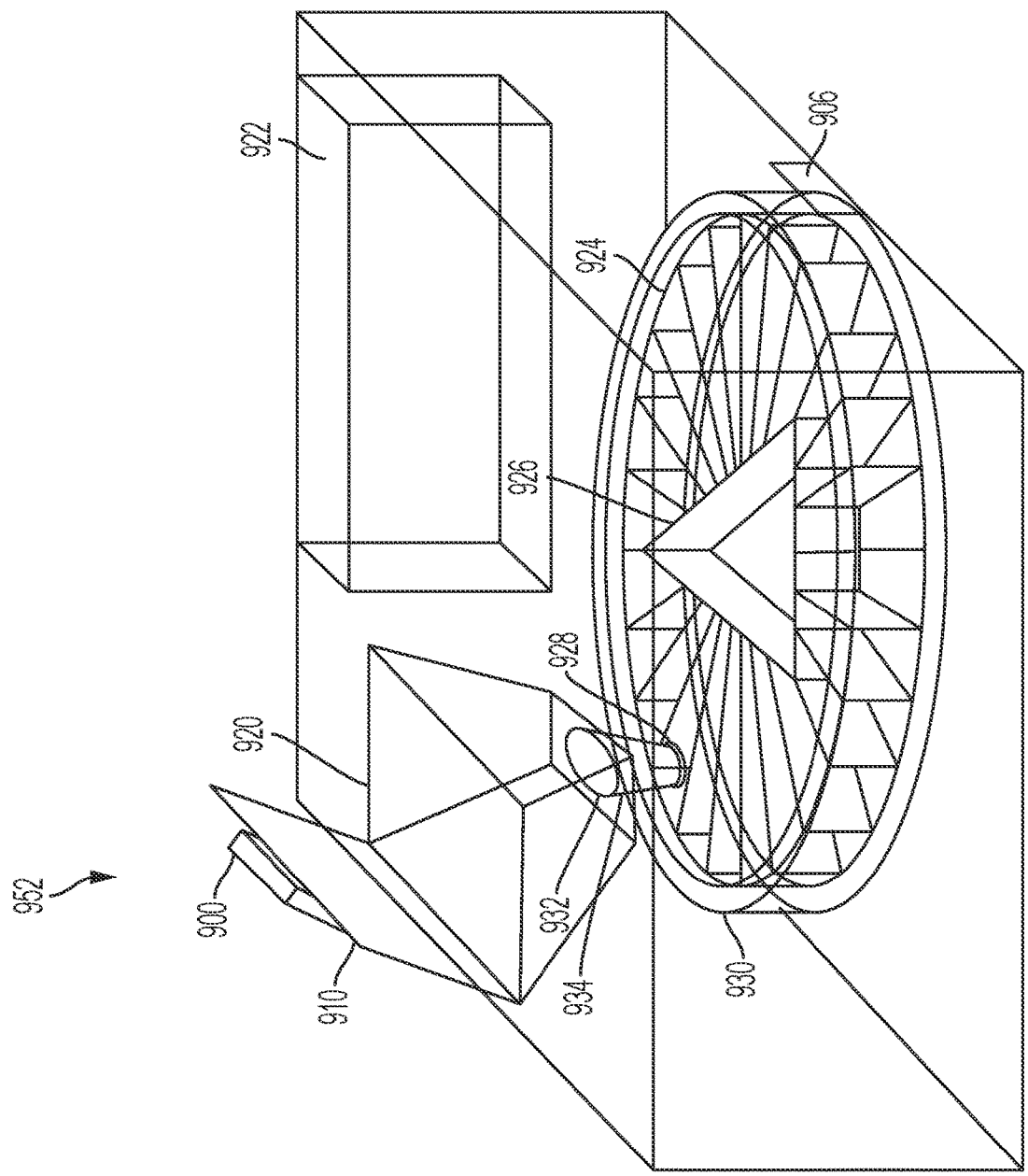
FIG. 17 is a diagram illustrating an interior view of the device of FIG. 16.
Figure 18:
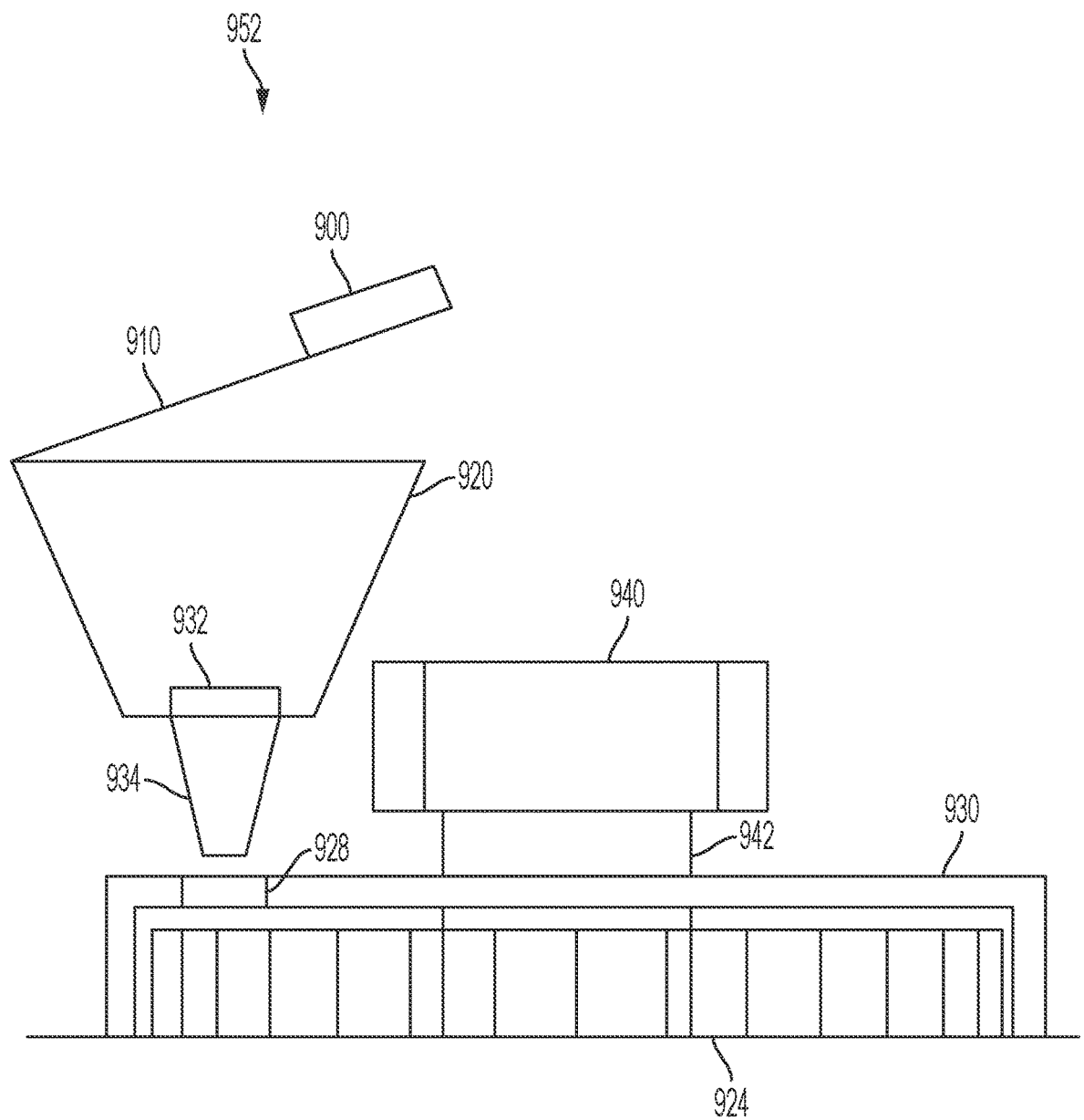
FIG. 18 is a diagram illustrating a sectional view of the device of FIG. 16.

FIG. 16 is a diagram illustrating an exterior view of a device for dispensing medication according to an embodiment of the present disclosure; FIG. 17 is a diagram illustrating an interior view of the device of FIG. 16; and FIG. 18 is a diagram illustrating a sectional view of the device of FIG. 16. Referring to FIGS. 16-18, the pill dispenser 952 may include a thumbprint identifier 902; a saliva sampling module 904; a dispensing gate 906; a touchscreen interface 908; a controller 922; a pill hopper 920; a pill hopper lid 910; a pill hopper lid lock 900; a pill hopper gate 932; a funnel 934; a dispensing drum 924 having a triangular opening 926 and individual compartments 950; a drum housing 930 having a drum loading hole 928; a stepper motor 940 and a drive shaft 942.

The pill dispenser 952 may house a dispensing drum 924 containing 21 individual compartments 950 so that a dispensing drum 924 can dispense up to three pills per day for seven days. A pharmacist may fill the dispensing drum 924 by opening the pill hopper lid 910 and transferring the prescribed quantity of medication from bulk containers in the pharmacy to the pill hopper 920.

Specifically, the controller 922 controls the stepper motor 940 to rotate the dispensing drum 924 by an individual compartment 950 width while controlling the pill hopper gate 932 to open wide enough to release an individual pill from the pill hopper 920 and into the funnel 934. The stepper motor 940 is coupled to the dispensing drum 924 via the drive shaft 942. The drive shaft is situated in the triangular opening 926 of the dispensing drum 924. The released pill falls through the funnel 934 and into the dispensing drum 924 via a drum loading hole 928 of the drum housing 930. The process can be repeated each time the prescription is renewed.

Subsequently, the pharmacist may lock the pill hopper lid lock 900 and connect a pharmacy computer to the pill dispenser 952 programming port to load the patient's identification code and dosing schedule in the controller 922 before the pill dispenser 952 is issued to the patient. The dosing schedule will be confirmed or updated on each occasion that the pill dispenser 952 is returned to the pharmacy to be refilled.

The controller 922 may alert the patient at each prescribed dosing interval. The alert can comprise flashing LEDs and/or an audible alarm. After receiving the alert, the patient will be prompted to respond by using the biometric identifier 902 to verify his or her identify. The biometric identifier could include, but is not limited to, a thumbprint identifier and a retina scan. In addition, the saliva sampling module 904 may enable a prescribing physician to verify a patient's compliance with the prescribed dosing schedule as deemed necessary.

The controller 922 controls the stepper motor 940 to rotate the dispensing drum 924 to position the next loaded compartment 950 immediately behind the dispensing gate 906 upon patient verification via the biometric identifier 902 and/or the saliva sampling module 904. The stepper motor 940 is coupled to the dispensing drum 924 via the drive shaft 942. The drive shaft 942 is situated in the triangular opening 926 of the dispensing drum 924. The controller 922 will unlock the dispensing gate 906 and alert the patient through the touchscreen interface 908 to remove the medication from the compartment 950. The alert can comprise flashing LEDs and/or an audible alarm. After the medication is removed, the controller 922 re-locks the dispensing gate 906.

Each medication dispensing event may generate a record that is transmitted to a patient database resident in secure cloud storage. Specifically, the patient database could function as a continuously updated repository of patient behavioral information wherein the patient database could be updated by messages automatically transmitted by the pill dispenser 152 to the patient database each time a patient attempts to access the medication stored within the pill dispenser 152 both in compliance with his or her prescription and otherwise. For example, the patient database could store patient data including, but not limited to, a patient identification number; a patient pill dispenser 152 serial number; a patient prescribed dosing schedule; patient biometric identification testing information; patient saliva analysis information; dispensing medication events; pill dispenser 152 tampering events; and pill dispenser 152 lockdown and restoration events. The patient database could be stored on the network control center server 124a of the operations center 120 or could be resident in a secure cloud storage facility (e.g, cloud-based) such as Dropbox Business; Egnyte Business; Amazon S3; and Microsoft OneDrive for Business.

The patient database could be accessible to medical providers and operations center administrators to facilitate securely dispensing medication to the patient using the pill dispenser 152 and for mitigating the risk of diversion of the medication to an unauthorized user. The patient database could also be accessible to third parties (e.g., researchers) with the purchase of a license wherein access to the patient database and patient data therein would be in compliance with HIPAA regulations.

For example, a prescribing physician can review the patient's most recent saliva test results in the patient database to verify that the patient is complying with his or her prescribed dosing schedule when a patient submits a prescription renewal request. The prescribing physician can transmit the requested prescription renewal to a pharmacy the patient identifies upon confirming the patient's compliance with his or her prescribed dosing schedule. As such, a patient may obtain prescribed medication when travelling.

The pill dispenser 952 is self contained and can be AC powered in normal use. In addition, the pill dispenser 952 may contain a rechargeable battery for portable operation. The pill dispenser housing can be plastic with an underlying continuous conductive metal foil inner lining. The pill dispenser 952 is designed so that any attempt by a patient or an unauthorized user to forcibly gain access to the prescribed medication contained within the pill dispenser 952 will damage the foil lining and cause the controller 922 to lock the dispensing gate 906. The controller 922 will transmit a tamper alert signal upon detecting tampering of the pill dispenser 952.

In addition, the pill dispenser 952 is designed so that destruction of the pill dispenser 952 also destroys the prescribed medication contained within the pill dispenser 952. For example, the dispensing drum 924 is housed within a hardened drum housing 930 mounted on the floor of the pill dispenser 952. As such, smashing or destroying the pill dispenser 952 will cause the prescribed medication contained within the pill dispenser 952 to also be destroyed. The pill hopper 920 and the pill hopper lid 910 may also be hardened and are secured by a tamper proof pill hopper lid lock 900.

Figure 19:
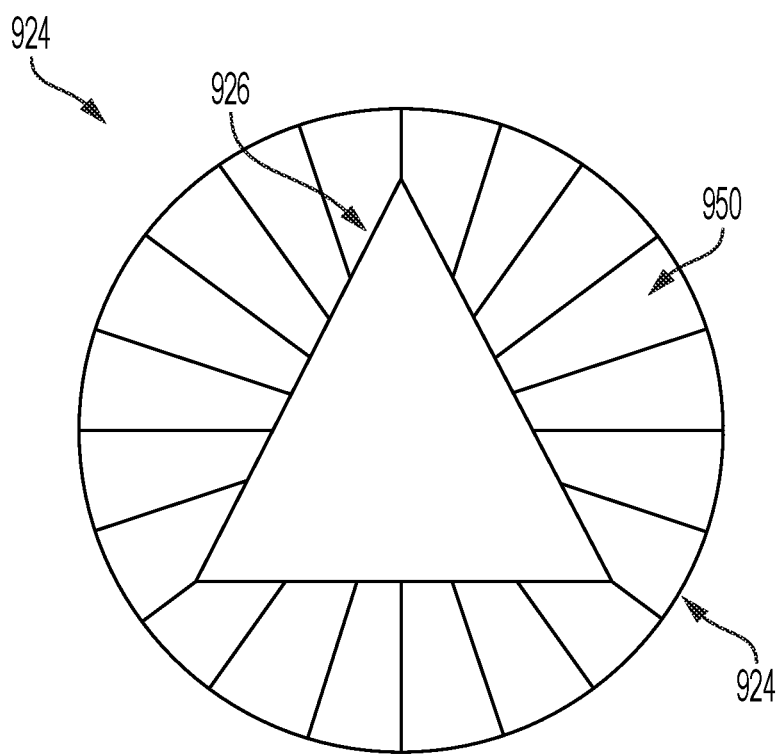
FIG. 19 is a diagram illustrating a top view of a component of the device of FIG. 16.

FIG. 19 is a diagram illustrating a top view of a component of the device of FIG. 16. FIG. 19 illustrates a top view of the dispensing drum 924 of the pill dispenser 952. As mentioned above, the dispensing drum 924 contains 21 individual compartments 950 so that the dispensing drum 924 can dispense up to three pills per day for seven days. In addition, the dispensing drum 924 includes a triangular opening 926. The stepper motor 940 is coupled to the dispensing drum 924 via the drive shaft 942 and the drive shaft is situated in the triangular opening 926 of the dispensing drum 924.

Figure 20:
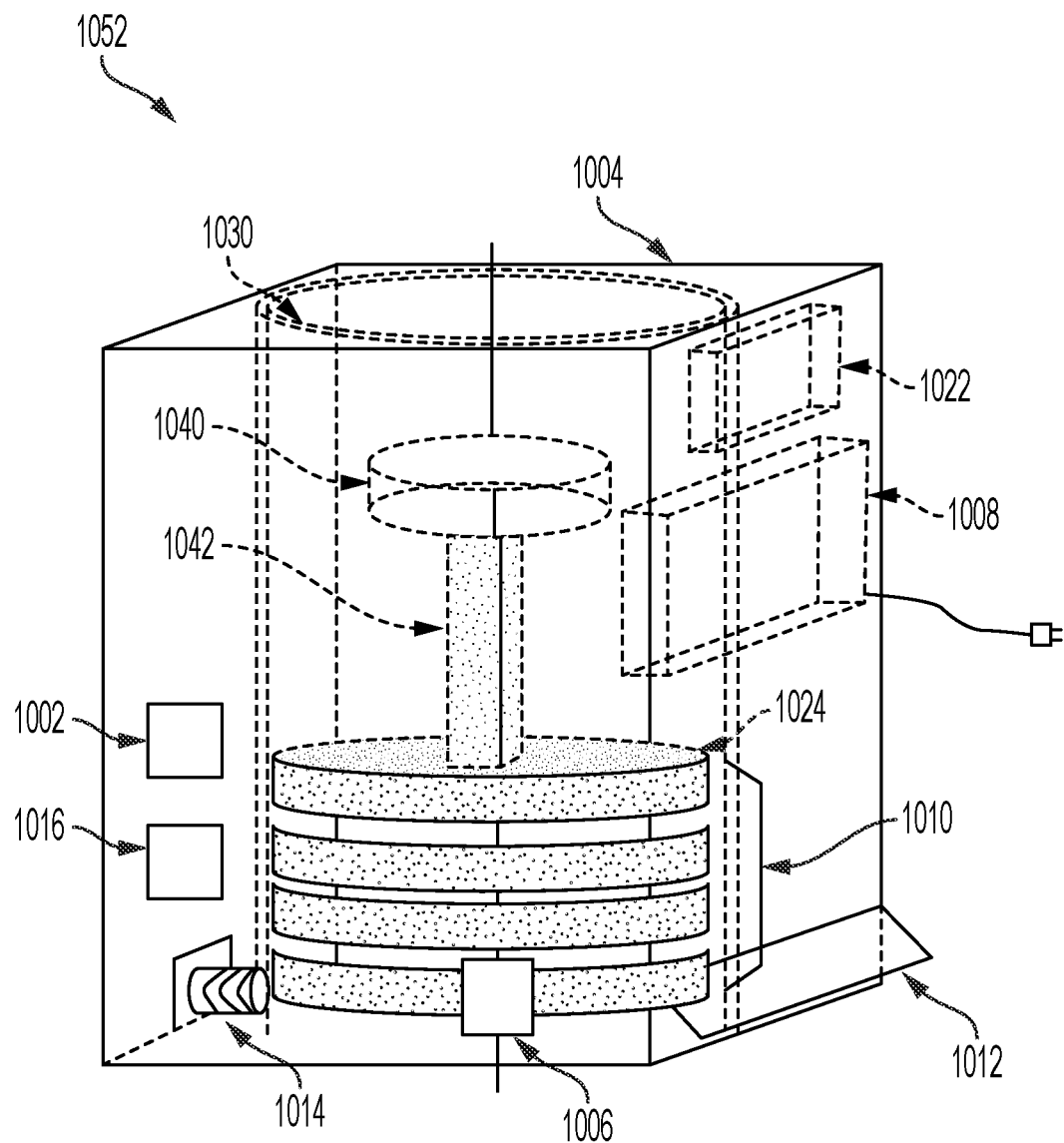
FIG. 20 is a diagram illustrating a device for dispensing medication according to an embodiment of the present disclosure.

FIG. 20 is a diagram illustrating a device for dispensing medication according to an embodiment of the present disclosure. The pill dispenser 1052 includes an assembly housing 1004; a biometric identifier 1002; a pill dispensing gate 1006; a power module 1008; a dispensing drum magazine 1010; a drum ejection flap 1012; a drum ejection spring 1014; a blood test analyzer 1016; a controller 1022; a pill dispensing drum 1024; a drum assembly enclosure 1030; a stepper motor 1040; and a drive shaft 1042.

The assembly housing 1004 serves as the outer shell of the pill dispenser 1052. The assembly housing 1004 may be comprised of plastic, but any suitable material known to one of skill in the art may be used. The biometric identifier 1002, the blood test analyzer 1016, the pill dispensing gate 1006, the drum ejection flap 1012, and the drum release (not shown) are located on the exterior of the assembly housing 1004.

The interior of the assembly housing 1004 comprises a drum assembly enclosure 1030, the controller 1022, the power module 1008, and the drum ejection spring 1014. The power module 1008 may include at least one battery.

The drum assembly enclosure 1030 comprises a number of pill dispensing drums 1024, a drive shaft 1042, a stepper motor 1040, and a dispensing drum magazine 1010. The pill dispensing drums 1024 are housed in the dispensing drum magazine 1010. The pill dispensing drums 1024 may be circular, stacked on top of each other, and mounted on the drive shaft 1042, which is connected to the stepper motor 1040. The pill dispensing drum 1024 at the bottom of the stack of pill dispensing drums aligns with the pill dispensing gate 1006 to dispense medication. The pill dispenser 1052 may comprise either four or five dispensing drums 1024 to fulfill a prescription. Each individual dispensing drum 1024 may contain up to twenty-one individual dosage compartments 1028 such that each dispensing drum 1024 may contain medication to be dispensed three times a day for one week. A memory (not shown) may contain the patient's customized dosing schedule. The controller 1022 may access the prescribed dosing schedule to control the pill dispensing. The dispensing drum magazine 1010 is rotated by the stepper motor 1040 to position the next loaded pill compartment 1028 behind the dispensing gate 1006 after a patient removes a dosage of medication. This process continues according to the patient's prescribed dosing schedule until each dispensing drum 1024 is emptied of medication.

A dispensing drum 1024 may be removed from the pill dispenser 1052 when the dispensing drum 1024 has been emptied of medication, for example at the end of a week's worth of doses. The patient may press the drum release, which may be loaded by the drum ejection spring 1014, to eject a dispensing drum 1024 through the drum ejection flap 1012. The remaining dispensing drums 1024 drop down and the lowest dispensing drum 1024 occupies the position adjacent to the pill dispensing gate 1006 when a dispensing drum 1024 is released. As such, the lowest dispensing drum 1024 is also aligned between the drum ejection spring 1014 and the drum ejection flap 1012. As the pill dispenser 1052 dispenses medication throughout the next week, the dispensing drum 1024 rotates until the patient empties the dispensing drum 1024 of medication. Subsequently, the dispensing drum 1024 is ejected and the remaining dispensing drums 1024 drop down to continue dispensing the next week's medication to the patient.

The pill dispenser 1052 may be configured to alert the patient at a prescribed dosing interval that a dosage of medication is ready for dispensing. For example, a light on the pill dispenser 1052 may blink or the device may make a sound. The patient verifies their identity using the blood tester 1016 and the biometric identifier 1002 when the patient receives the dosage alert. The patient may also verify their previous dosage compliance if required by the dosage instructions provided by the prescribing physician. Once the patient's identity has been verified, the pill dispenser 1052 dispenses the medication. Each dispensing event may trigger a corresponding record transmitted to a database. The database may reside on the prescribing physician's computer. The database may also be accessible via the prescribing physician's computer even if the database does not reside on the physician's computer.

Figure 21:
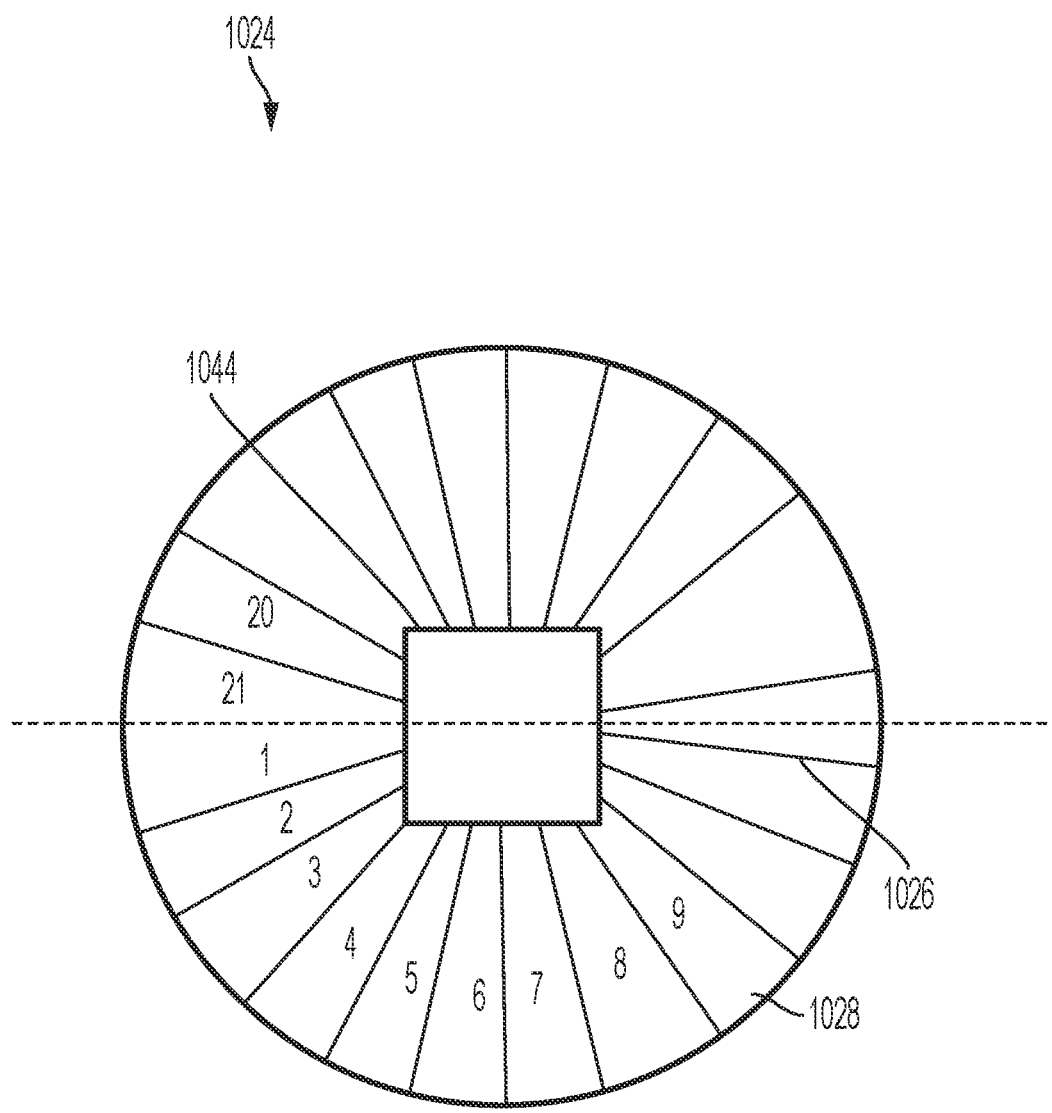
FIG. 21 is a diagram illustrating a top view of a component of the device of FIG. 20.
Figure 22:
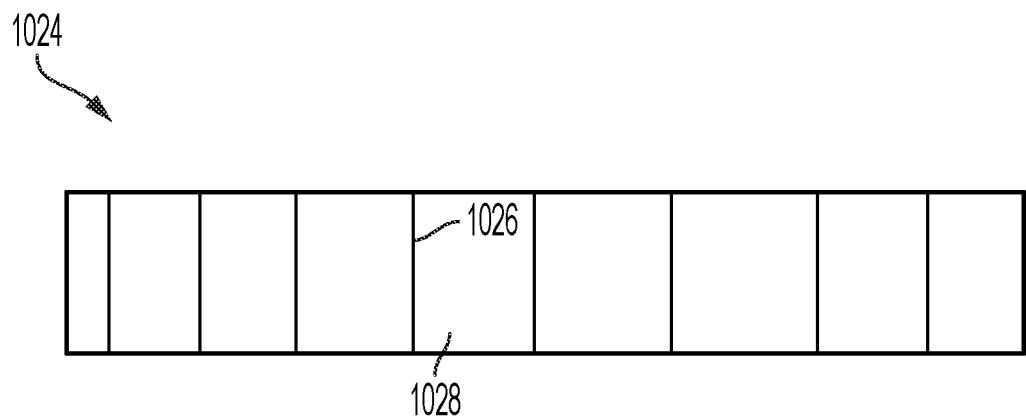
FIG. 22 is a diagram illustrating a side view of the component of FIG. 21.

FIG. 21 is a diagram illustrating a top view of a component of the device of FIG. 20. Specifically, FIG. 21 illustrates a top view of the dispensing drum 1024 of the pill dispenser 1052. The dispensing drum 1024 as shown contains a square drive shaft opening 1044 to receive the drive shaft 1042, twenty-one pill compartments 1028, and twenty-two partitions 1026 dividing the pill compartments 1028. It is noted that the drive shaft opening 1044 may be of any configuration or shape provided that the drive shaft opening 1044 can receive the drive shaft 1042. The twenty-one pill compartments 1028 correspond to twenty-one doses of medication over one week, for example three doses each day for seven days. Although shown here as twenty-one pill compartments 1028, different amounts of pill compartments 1028 may be utilized. For example, a dispensing drum 1024 may contain seven, fourteen, or any number of pill compartments 1028.

Figure 23:
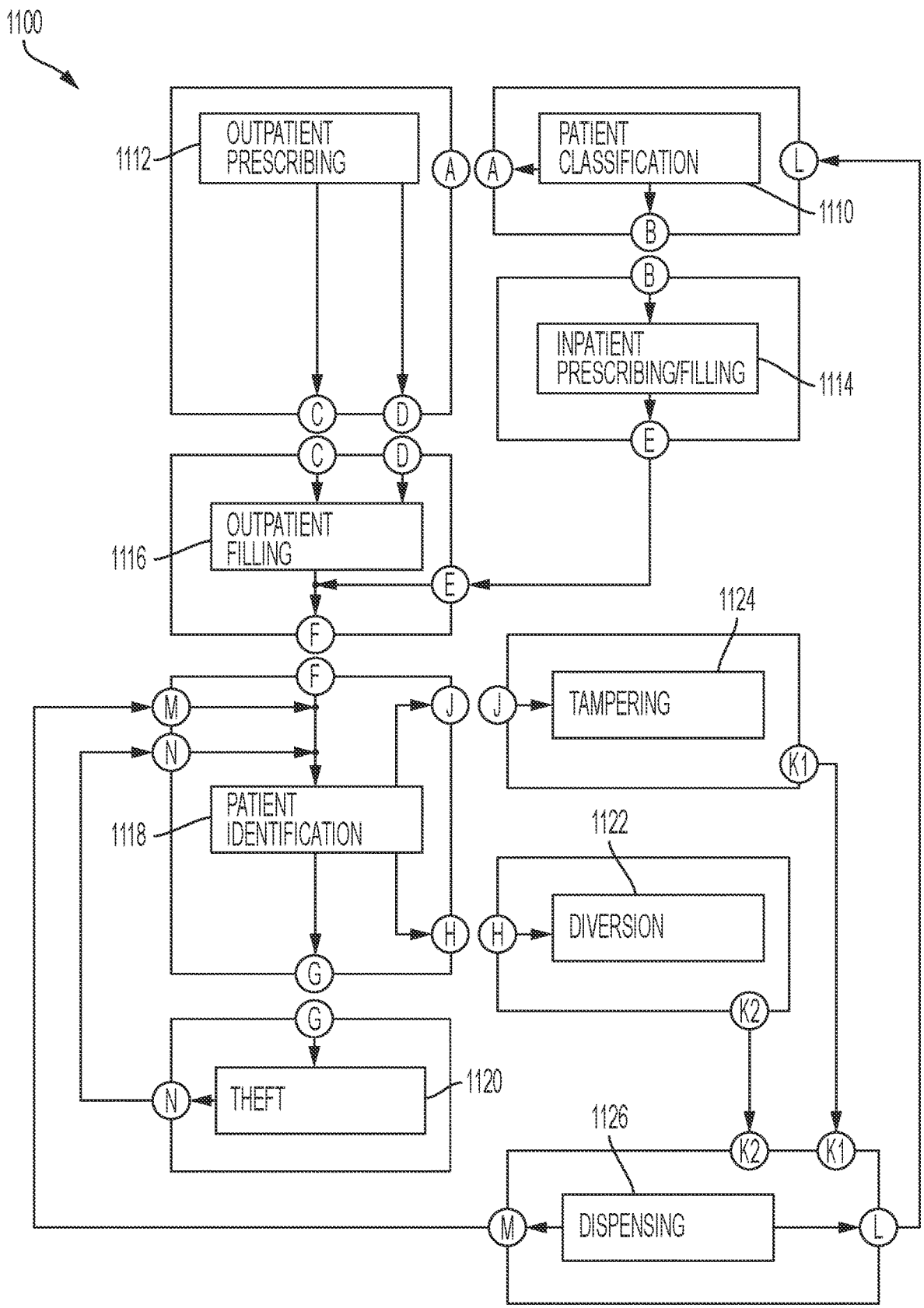
FIG. 23 is a flowchart illustrating an overview of processing steps carried out by another embodiment of the system of the present disclosure.

FIGS. 23-32 are flowcharts illustrating processing steps carried out by another embodiment of the system of the present disclosure. Specifically, FIG. 23 is a flowchart 1100 illustrating an overview of processing steps 1112-1126 carried out by another embodiment of the system of the present disclosure and FIGS. 24-32 are flowcharts illustrating enumerated steps 1112-1126 of FIG. 23 in greater detail. As shown in FIG. 23, the flowchart 1100 includes patient classification step 1110, outpatient prescribing step 1112, inpatient prescribing/filling step 1114, outpatient filling step 1116, patient identification step 1118, theft step 1120, diversion step 1122, tampering step 1124 and dispensing step 1126. It is noted that letters A-N of FIG. 23 denote transitions between steps 1112-1126 of FIG. 23. It is also noted that transitions between one or more of steps 1112-1116 may occur based on a variety of conditions contained therein.

Figure 24:
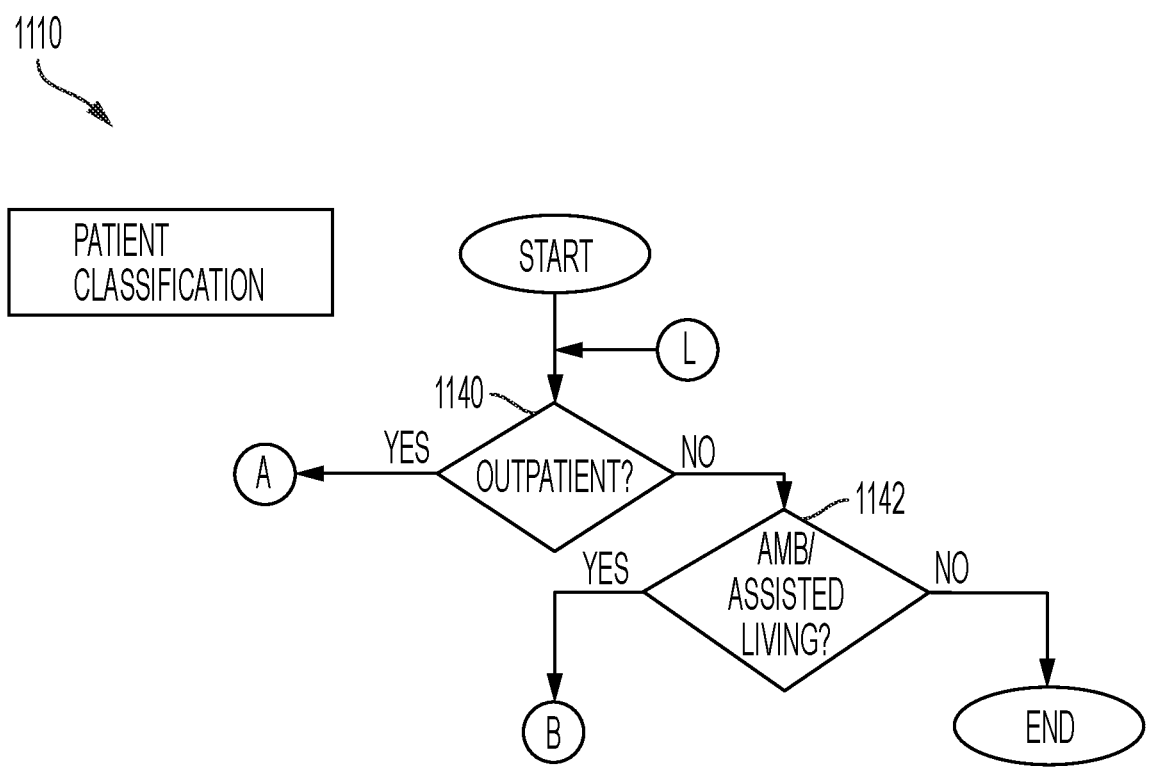
FIG. 24 is a flowchart illustrating step 1110 of FIG. 23 in greater detail.
Figure 32:
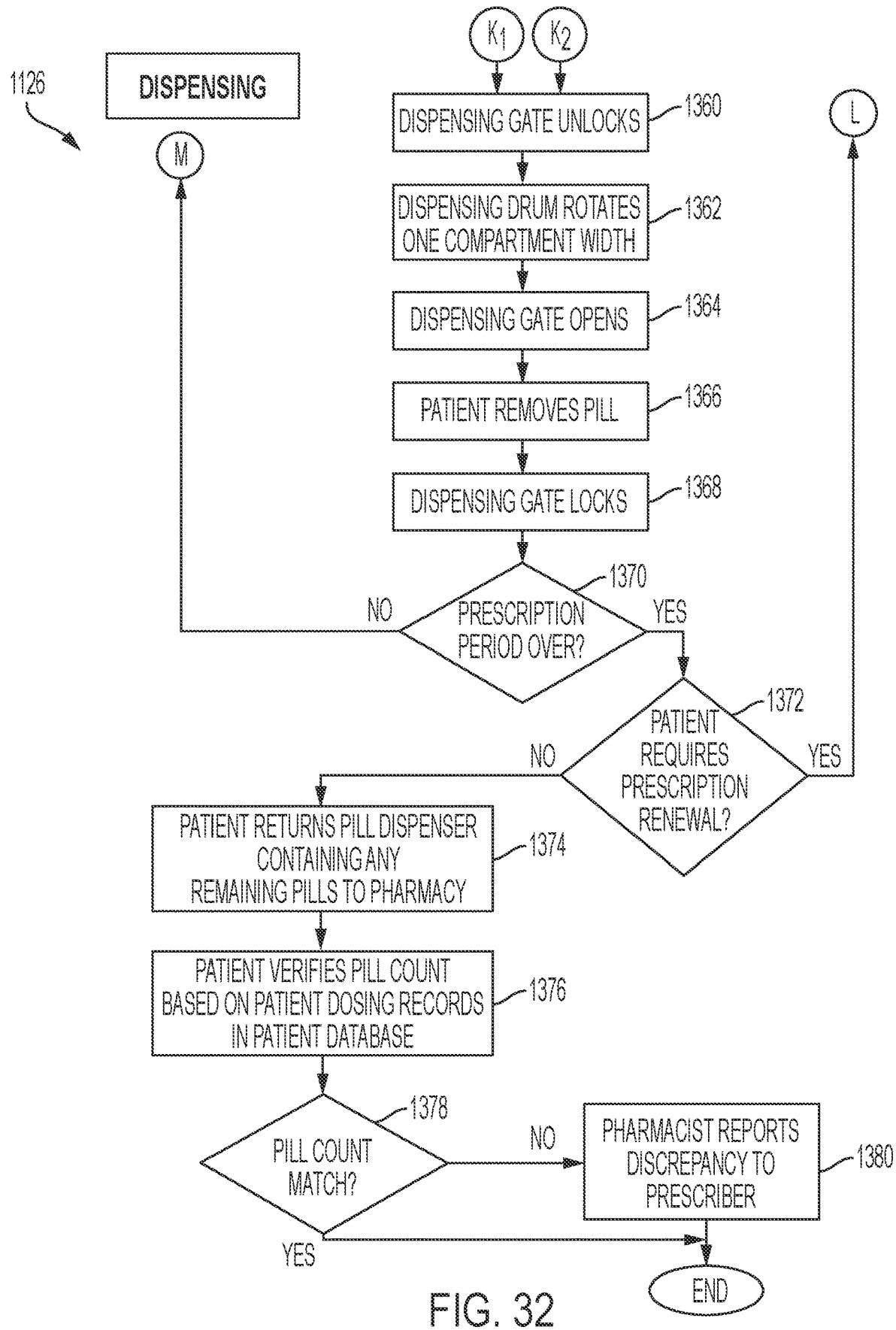
FIG. 32 is a flowchart illustrating step 1126 of FIG. 23 in greater detail.

FIG. 24 is a flowchart illustrating patient classification step 1110 of FIG. 23 in greater detail. In step 1140, the prescribing physician 130 determines whether the patient is an outpatient. The process proceeds to outpatient prescribing step 1112 ("A" as shown in FIGS. 23 and 24) if the prescribing physician 130 determines the patient is an outpatient. Alternatively, the process proceeds to step 1142 if the prescribing physician 130 determines the patient is not an outpatient. In step 1142, the prescribing physician 130 determines whether the patient resides in an ambulatory care or assisted living center. The process proceeds to inpatient prescribing/filling step 1114 ("B" as shown in FIGS. 23 and 24) if the prescribing physician 130 determines the patient resides in an ambulatory care or assisted living center. Alternatively, the process ends if the prescribing physician 130 determines the patient does not reside in an ambulatory care or assisted living center. It is noted that the process returns to patient classification step 1110 if a patient requests a prescription renewal (step 1372 of FIG. 32) during dispensing step 1126 ("L" as shown in FIGS. 23, 24 and 32).

Figure 25:
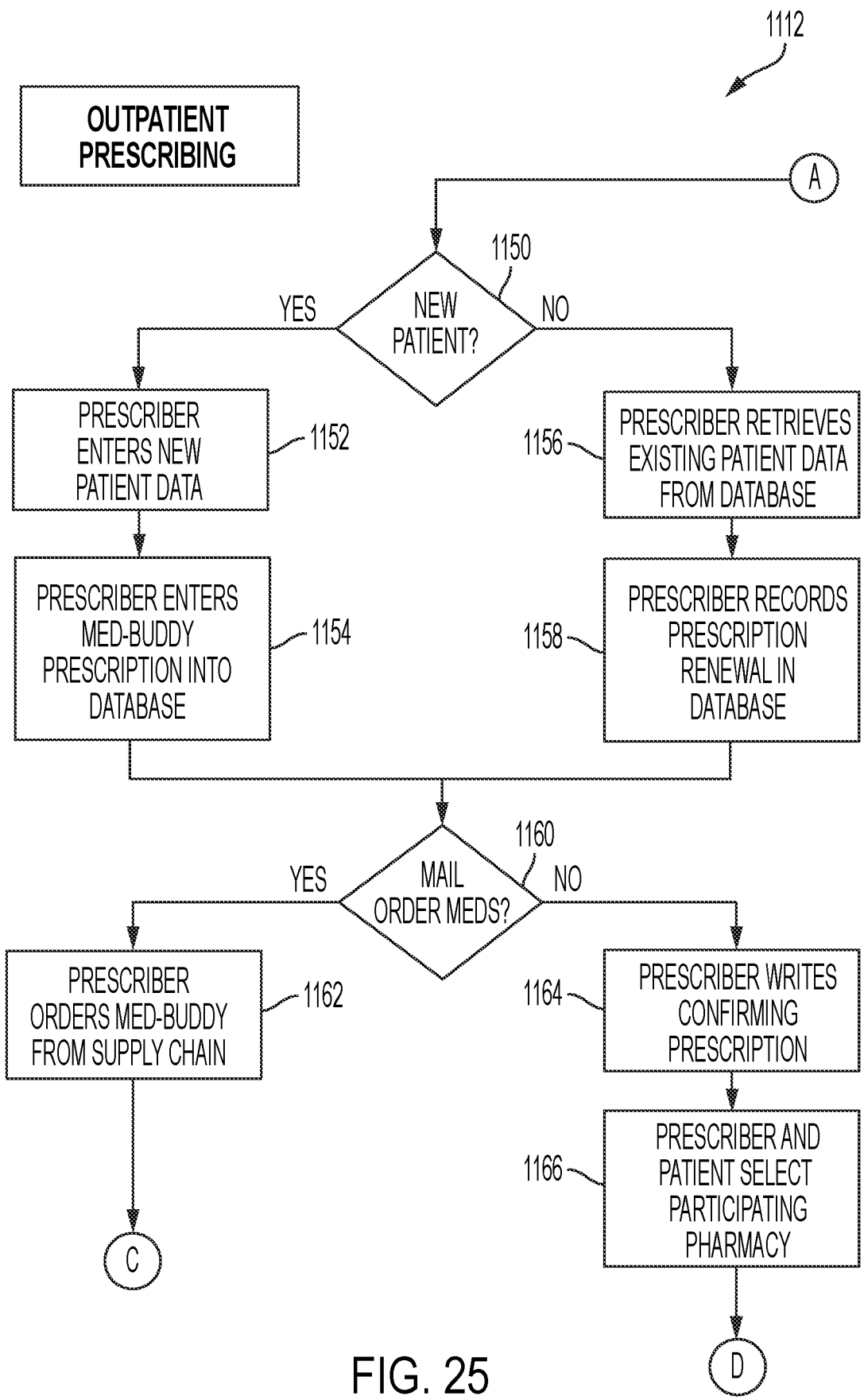
FIG. 25 is a flowchart illustrating step 1112 of FIG. 23 in greater detail.

FIG. 25 is a flowchart illustrating outpatient prescribing step 1112 of FIG. 23 in greater detail. During outpatient prescribing step 1112, a prescribing physician 130 prescribes a patient a medication. As noted above, the process proceeds to outpatient prescribing step 1112 when the prescribing physician 130 determines the patient is an outpatient.

Beginning in step 1150, the prescribing physician 130 determines whether the patient is a new patient. For example, the prescribing physician 130 determines whether the patient's identifying information and relevant data (e.g., medical history) are stored in a database of the subscription application. Then, in step 1152, the prescribing physician 130 enters the patient's identifying information and relevant data into the subscription application database if the patient is new. Further, in step 1154, the prescribing physician 130 enters the patient's prescription into the database of the subscription application. Alternatively, in step 1156, the prescribing physician 130 retrieves the patient's identifying information and relevant data from the database of the subscription application if the patient is an existing patient.

Further, in step 1158, the prescribing physician 130 records the patient's prescription renewal in the database of the subscription application.

Next, in step 1160, the patient determines whether to order his/her prescription through a mail-order pharmacy. In step 1162, the prescribing physician 130 orders the patient's prescription (e.g., the pill dispenser 152) from a pharmaceutical supplier if the patient determines to order his/her prescription through a mail-order pharmacy. Subsequently, the process proceeds to outpatient filling step 1116 ("C" as shown in FIGS. 23 and 25). Alternatively, in step 1164, the prescribing physician 130 writes a confirming prescription if the patient determines to order his/her prescription through a conventional brick and mortar pharmacy. Further, in step 1166, the prescribing physician 130 and the patient select a pharmacy 140 to fill the prescription. Subsequently, the process proceeds to outpatient filling step 1116 ("D" as shown in FIGS. 23 and 25).

Figure 26:
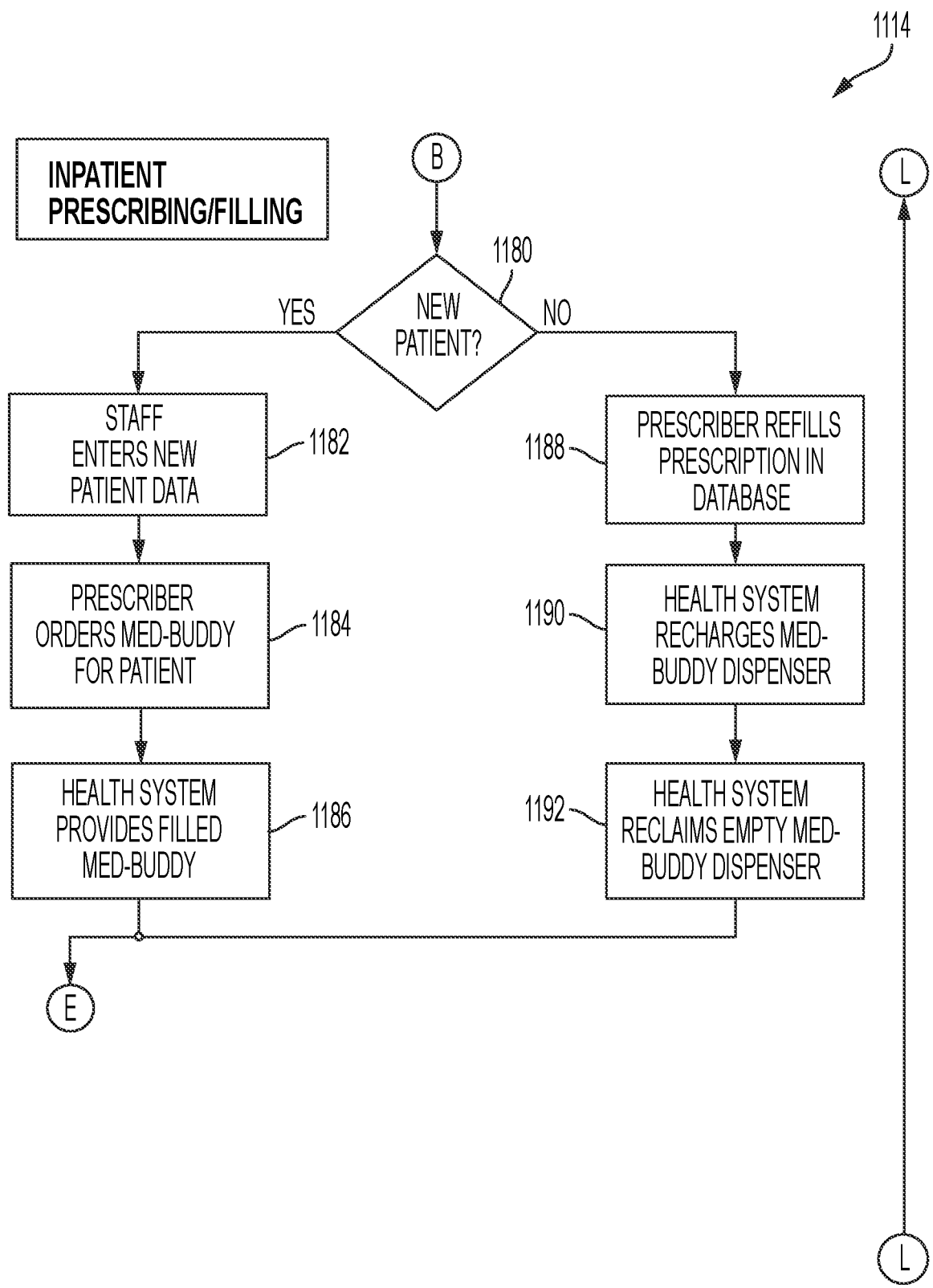
FIG. 26 is a flowchart illustrating step 1114 of FIG. 23 in greater detail.

FIG. 26 is a flowchart illustrating inpatient prescribing/filling step 1114 of FIG. 23 in greater detail. As noted above, the process proceeds to inpatient prescribing/filling step 1114 if the prescribing physician 130 determines the patient resides in an ambulatory care or assisted living center. Beginning in step 1180, the prescribing physician 130 determines whether the patient is a new patient. For example, the prescribing physician 130 determines whether the patient's identifying information and relevant data (e.g., medical history) are stored in a database of the subscription application. Then, in step 1182, the prescribing physician 130 or a staff member of the ambulatory care or assisted living center enters the patient's identifying information and relevant data into the subscription application database if the patient is new. Further, in step 1184, the prescribing physician 130 commissions the pill dispenser 152 for the patient. In step 1186, a health system provider (e.g., the ambulatory care or assisted living center) provides the pill dispenser 152 containing the patient's prescription to the patient. Subsequently, the process proceeds to the end of outpatient filling step 1116 ("E" as shown in FIGS. 23 and 26) and directly to patient identification step 1118 ("F" as shown in FIG. 23).

Alternatively, in step 1188, the prescribing physician 130 retrieves the patient's identifying information and relevant data from the database of the subscription application and refills the patient's prescription if the patient is an existing patient. Next, in step 1190, the health system provider (e.g., the ambulatory care or assisted living center) provides a pill dispenser 152 filled with the patient's prescription to the patient. Lastly, in step 1192, the health system provider reclaims the patient's empty pill dispenser 152. Subsequently, the process proceeds to the end of outpatient filling step 1116 ("E" as shown in FIGS. 23 and 26) and directly to patient identification step 1118 ("F" as shown in FIG. 23).

Figure 27:
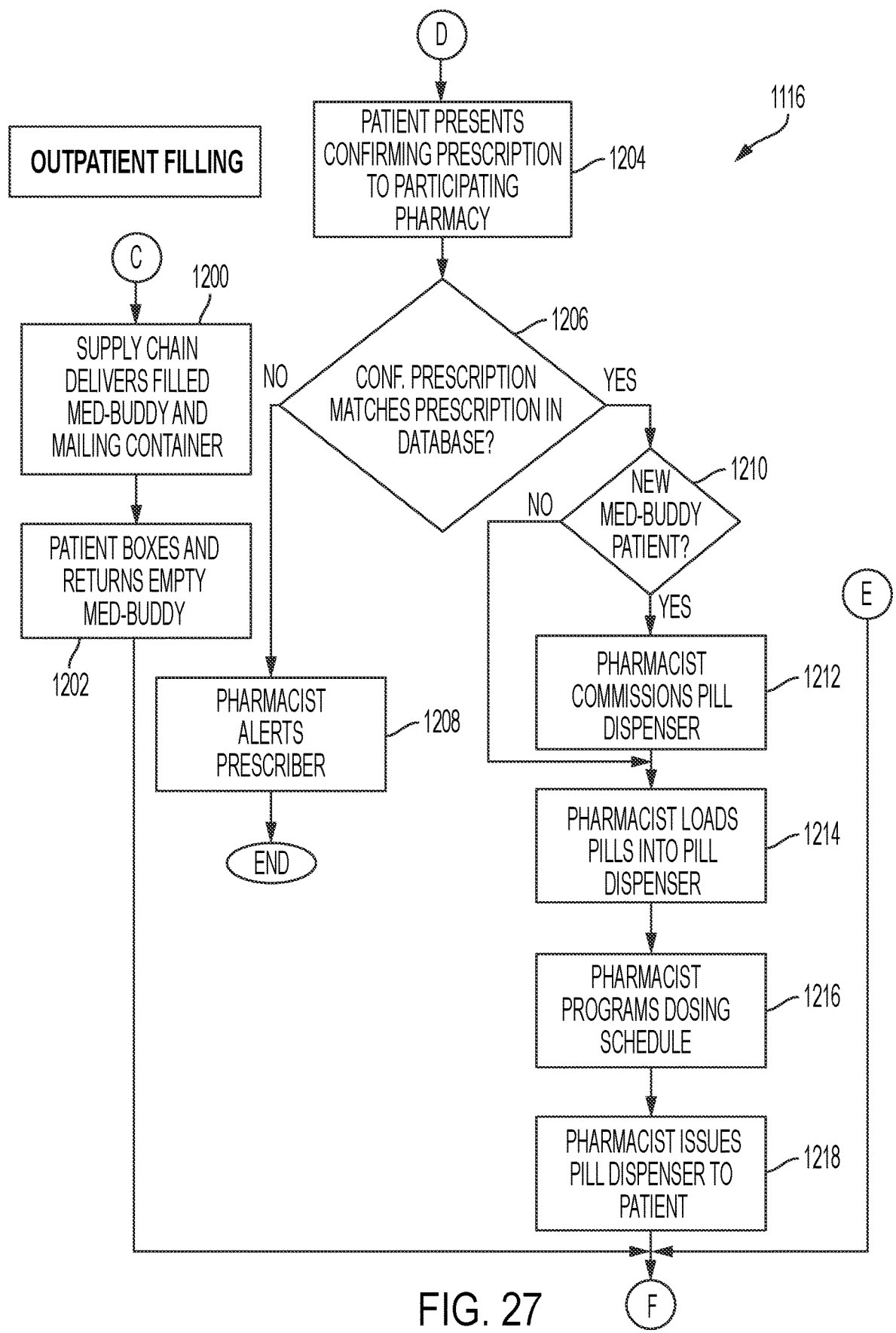
FIG. 27 is a flowchart illustrating step 1116 of FIG. 23 in greater detail.

FIG. 27 is a flowchart illustrating outpatient filling step 1116 of FIG. 23 in greater detail. As noted above, the process proceeds to outpatient filling step 1116 when the prescribing physician 130 orders the patient's prescription (e.g., the pill dispenser 152) from a pharmaceutical supplier. Beginning in step 1200, the pharmaceutical supplier ships and delivers the pill dispenser 152 filled with the patient's prescription and a mailing container to the patient. Then, in step 1202, the patient packages and returns the empty pill dispenser 152 in the received mailing container. Subsequently, the process proceeds to patient identification step 1118 ("F" as shown in FIGS. 23 and 27).

Additionally and as noted above, the process also proceeds to outpatient filling step 1116 when the prescribing physician 130 and the patient select a pharmacy 140 to fill the prescription.

Beginning in step 1204, the patient presents the confirming prescription to the pharmacy 140. Then, in step 1206, the pharmacy 140 determines whether the confirming prescription matches the prescription in the subscription application database. In step 1208, the pharmacy 140 alerts the prescribing physician 130 if the pharmacy 140 determines that the confirming prescription and the prescription in the subscription application database do not match. Subsequently, the process ends.

Alternatively, in step 1210, the pharmacy 140 determines whether the patient's identifying information and relevant data (e.g., medical history) are stored in the database of the subscription application if the confirming prescription and the prescription in the subscription application database match. Based on the determination, the pharmacy 140 determines whether to commission a new pill dispenser 152 and associate the new pill dispenser 152 with the patient or fill an existing pill dispenser 152 associated with the patient. For example, the pharmacy 140 commissions the new pill dispenser 152 in step 1212, if the pharmacy 140 determines that the patient's identifying information and relevant data are not stored in the database of the subscription application. Otherwise, the process proceeds directly to step 1214 if the pharmacy 140 determines that the patient's identifying information and relevant data are stored in the database of the subscription application. In step 1214, the pharmacy 140 loads the medication into an existing pill dispenser 152 associated with the patient. In step 1216, the pharmacy 140 programs the pill dispenser 152 according to a prescribed dosing schedule. Then, in step 1218, the pharmacy 140 issues the pill dispenser to the patient. Thereafter, the process proceeds to the patient identification step 1118 ("F" as shown in FIGS. 23 and 27). It is noted that the process may proceed from inpatient prescribing/filling step 1114 to the end of outpatient filling step 1116 ("E" as shown in FIGS. 23 and 26) and directly to patient identification step 1118 ("F" as shown in FIG. 23).

Figure 28:
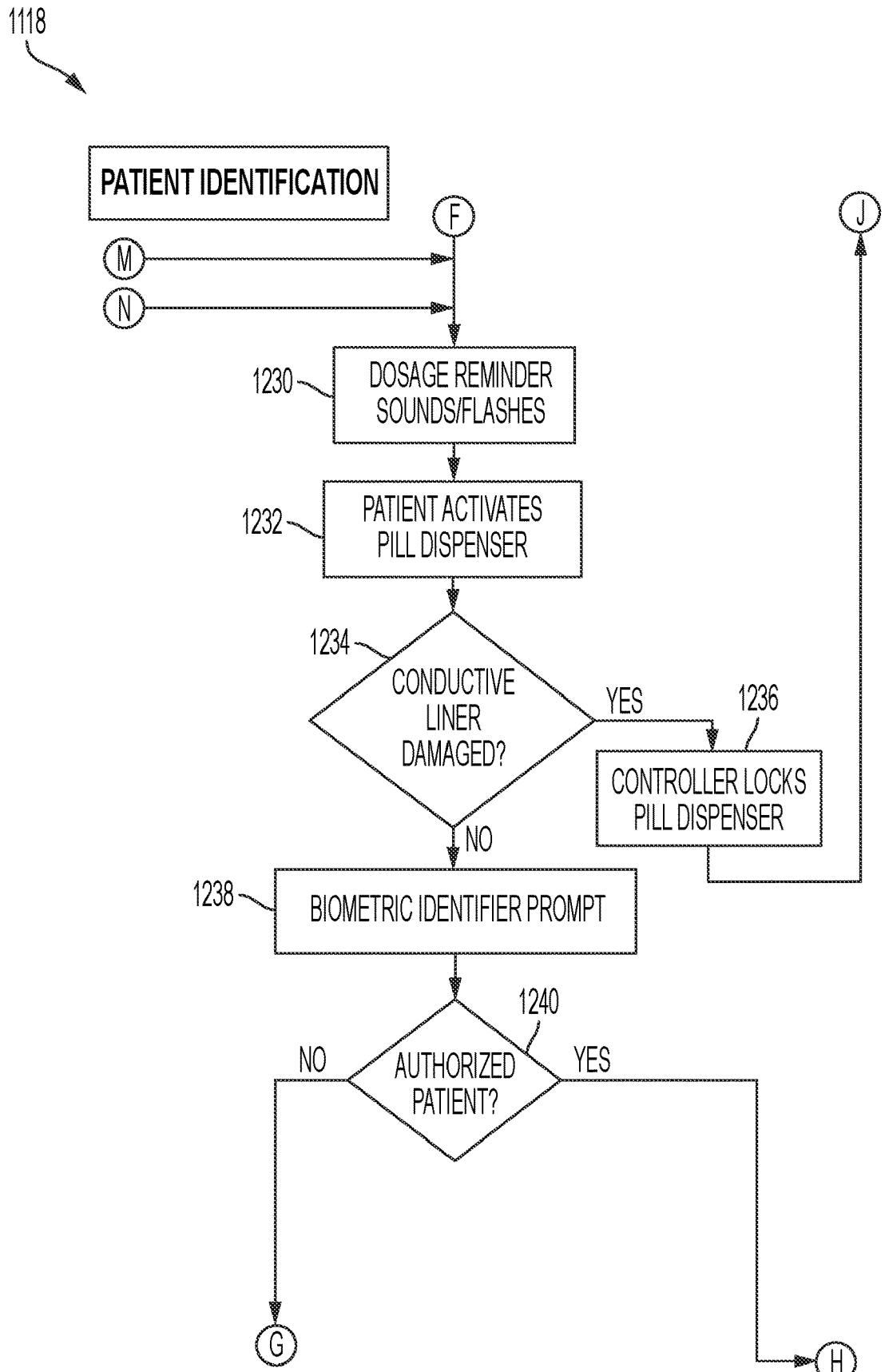
FIG. 28 is a flowchart illustrating step 1118 of FIG. 23 in greater detail.

FIG. 28 is a flowchart illustrating patient identification step 1118 of FIG. 23 in greater detail. During patient identification step 1118, the patient attempts to access prescribed medication within the pill dispenser 152 to take a scheduled dose of the prescribed medication by verifying his or her identity. As noted above, the process proceeds to patient identification step 1118 when the patient packages and returns the empty pill dispenser 152 in the mailing container (step 1202 of FIG. 27), the pharmacy 140 issues the pill dispenser 152 to the patient (step 1218 of FIG. 27), the health system provider (e.g., the ambulatory care or assisted living center) provides the pill dispenser 152 filled with the patient's prescription to the patient (step 1186 of FIG. 26), or the health system provider reclaims the patient's empty pill dispenser 152 (step 1192 of FIG. 26). As will be discussed in detail below, the process may return to patient identification step 1118 when patient services 122*c* loads an amount of prescription medication into the pill dispenser 152 to fill the prescription, programs the pill dispenser 152 according to the prescribed dosing schedule, and ships the pill dispenser 152 to the patient (step 1270 of FIG. 29) or if the controller 304 determines the prescription period is not over (step 1370 of FIG. 32).

Beginning in step 1230, the pill dispenser 152 notifies the patient via a reminder or alert to take a dosage of the prescribed medication. The reminder or alert can include flashing light emitting diodes (LEDs) on an exterior surface of the pill dispenser 152 and/or sound. In step 1232, the patient activates the pill dispenser 152 to attempt to access the prescribed medication contained within the pill dispenser 152. Then, in step 1234, the pill dispenser 152 determines whether the conductive liner along the interior of the pill dispenser 152 is damaged. The controller 304 locks the pill dispenser 152 in step 1236 if the pill dispenser 152 determines the conductive liner along the interior of the pill dispenser 152 is damaged. Subsequently, the process proceeds to tampering step 1124 ("J" as shown in FIGS. 23 and 28).

Alternatively, the pill dispenser 152 prompts the patient to verify his or her identity via the biometric identifier in step 1238 if the pill dispenser 152 determines the conductive liner is not damaged. The pharmacy 140 can conduct a baseline biometric test on the patient and store the results in the memory of the controller 304 of the pill dispenser 152 when the pill dispenser 152 is originally issued to the patient. The controller 304 of the pill dispenser 152 will only unlock the dispensing gate 324 when the biometric test data matches the stored data. Accordingly, in step 1240, the pill dispenser 152 determines whether the patient is authorized to access the scheduled dose of the prescribed medication from the pill dispenser 152. The pill dispenser 152 proceeds to theft step 1120 ("G" as shown in FIGS. 23 and 28) if the patient is unauthorized to access the scheduled dose of the prescribed medication. Alternatively, the process proceeds to diversion step 1122 ("H" as shown in FIGS. 23 and 28) to determine whether a saliva test is required if the pill dispenser 152 determines the patient is authorized to access the scheduled dose of the prescribed medication contained within the pill dispenser 152. Theft step 1120 and diversion step 1122 will be discussed in more detail below.

Figure 29:
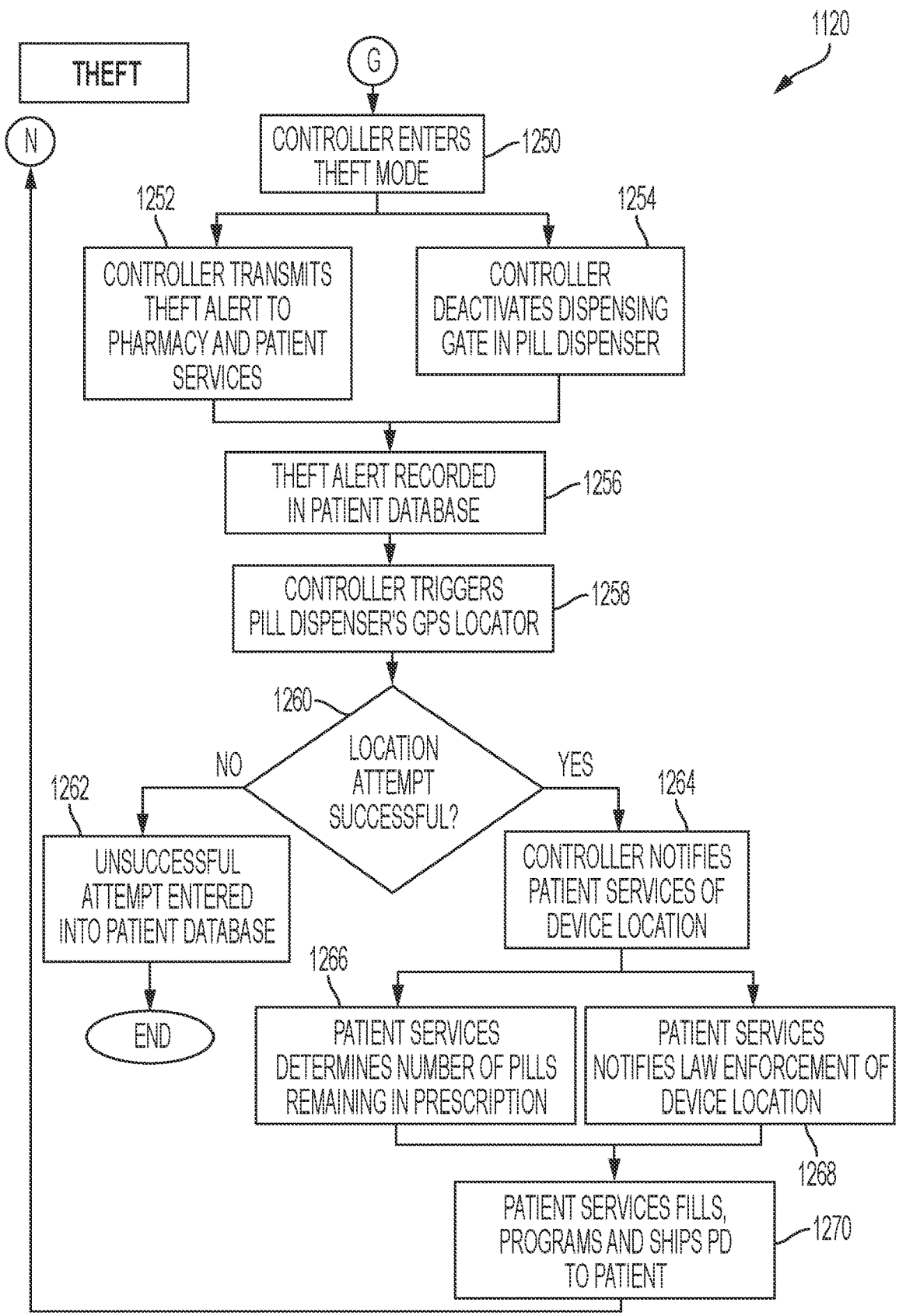
FIG. 29 is a flowchart illustrating step 1120 of FIG. 23 in greater detail.

FIG. 29 is a flowchart illustrating theft step 1120 of FIG. 23 in greater detail. As noted above, the process proceeds to theft step 1120 if the pill dispenser 152 determines the patient is unauthorized to access the scheduled dose of the prescribed medication contained within the pill dispenser 152 (step 1240 of FIG. 28). Beginning in step 1250, the pill dispenser 152 detects a theft and enters theft mode. As mentioned above, the pill dispenser 152 includes a GPS module 306 to facilitate a pill dispenser's retrieval (if lost) or deactivation (if stolen). Specifically, when a theft is indicated, the controller 304 concurrently transmits a theft alert to the pharmacy 140 and patient services 122c in step 1252 and deactivates the pill dispenser 152 in step 1254.

In step 1256, the theft alert is recorded in the database of the subscription application. Then, in step 1258, the controller 304 activates the GPS module 306 to determine a location of the pill dispenser 152. Subsequently, in step 1260, the controller 304 attempts to determine a location of the pill dispenser 152 via the GPS module 306. In step 1262, the controller 304 records an unsuccessful location attempt in the database of the subscription application if the controller 304 does not determine the location of the pill dispenser 152 and the process ends.

Alternatively, in step 1264, the controller 304 notifies patient services 122c of the location of the pill dispenser 152 if the controller 304 determines the location of the pill dispenser 152. As such, patient services 122c can retrieve the pill dispenser 152. Next, patient services 122c concurrently determines an amount of prescription medication remaining within the pill dispenser 152 in step 1266 and notifies law enforcement of the determined location of the pill dispenser 152 in step 1268. Then, in step 1270, patient services 122c loads an amount of prescription medication into the pill dispenser 152 to fill the prescription, programs the pill dispenser 152 according to the prescribed dosing schedule, and ships the pill dispenser 152 to the patient. The process then returns to patient identification step 1118 ("N" as shown in FIGS. 23 and 29).

Figure 30:
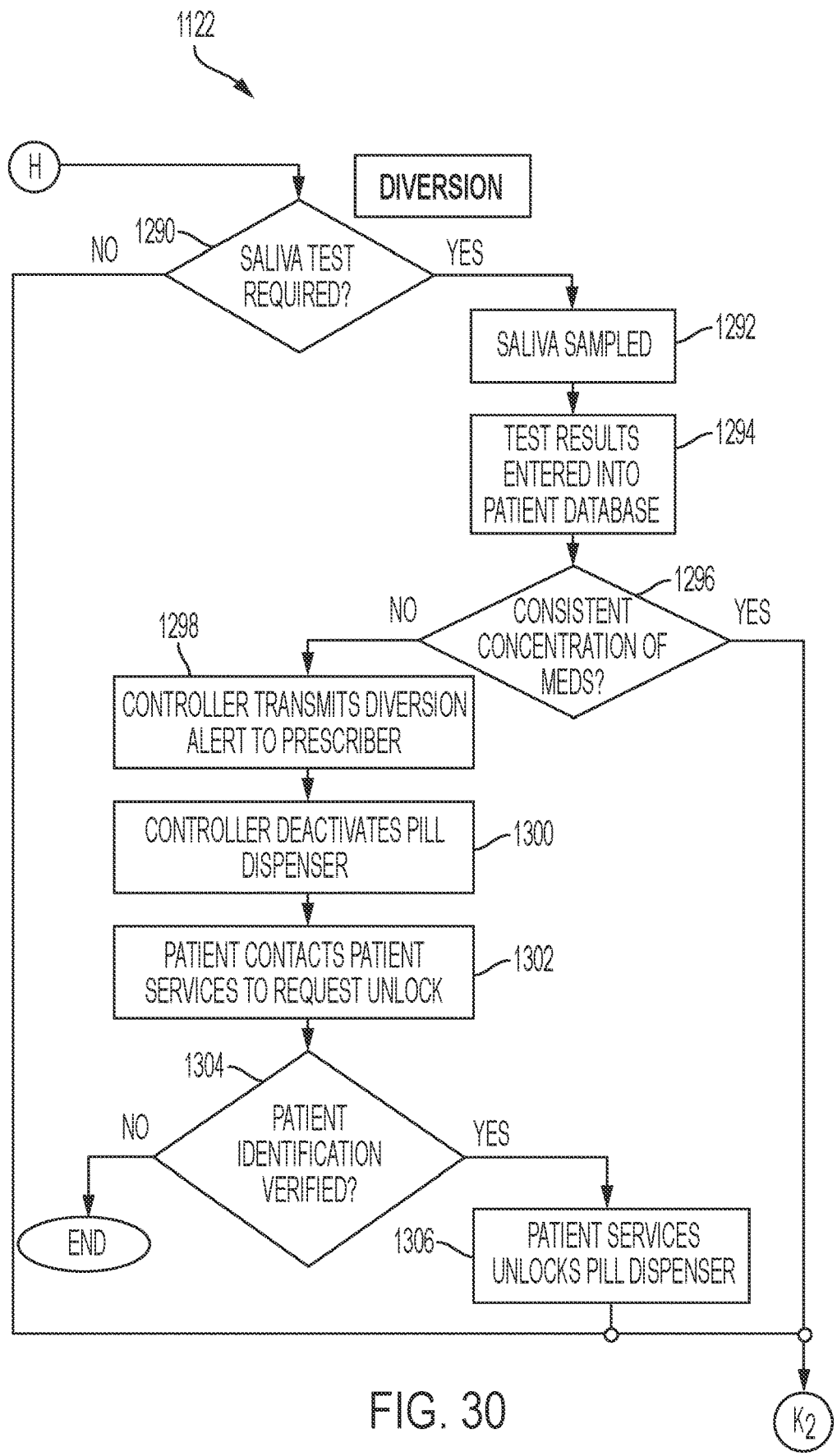
FIG. 30 is a flowchart illustrating step 1122 of FIG. 23 in greater detail.

FIG. 30 is a flowchart illustrating diversion step 1122 of FIG. 23 in greater detail. As noted above, the process proceeds to diversion step 1122 when the pill dispenser 152 determines the patient is authorized to access the scheduled dose of the prescribed medication contained within the pill dispenser 152 (step 1240 of FIG. 28).

During diversion step 1122, the system determines whether the patient is diverting the prescribed medication to an unauthorized user by analyzing a patient's saliva sample via a saliva sampling module. Generally, in the event a patient has been removing medication from the pill dispenser 152 according to the prescribed dosing schedule but the saliva sampling module determines that the level of the prescribed medication in the patient's bloodstream is inconsistent with the prescribed dosing schedule, the controller 304 will disable the dispensing gate 324 and transmit a diversion alert to the prescribing physician 130.

Beginning in step 1290, the pill dispenser 152 determines whether a saliva test is required. Specifically, at predetermined intervals selected by the prescribing physician 130 and programmed into the pill dispenser 152, the patient may be required to deposit a saliva sample onto the saliva sampling module. The process proceeds to dispensing step 1126 ("$K_2$" as shown in FIGS. 23 and 30) if the pill dispenser 152 determines the saliva test is not required. During dispensing step 1126, the pill dispenser 152 dispenses the patient's prescribed medication to the patient. Dispensing step 1126 will be discussed in further detail below.

Alternatively, in step 1292, the patient is prompted to provide a saliva sample and the patient's saliva is sampled if the pill dispenser 152 determines the saliva test is required. The level of the prescribed medication in the patient's bloodstream may be determined by the saliva sampling module's analysis of the saliva sample (e.g., NarcoCheck®) compared with a standardized control and is a reliable indicator of the patient's compliance with the prescribed dosing schedule. The saliva sampling module performs the analysis of the saliva sample according to an algorithm built into the controller 304 that accounts for physical characteristics of a patient including, but not limited to, age and gender. Then, in step 1294, the saliva sampling module result is entered into the patient database 134.

In step 1296, the system determines whether the saliva sampling module result is consistent with the patient's prescribed dosing schedule. The process proceeds to dispensing step 1126 ("$K_2$" as shown in FIGS. 23 and 30) if the saliva sampling module result is consistent with the patient's prescribed dosing schedule. Alternatively, the process proceeds to step 1298 if the saliva sampling module result is inconsistent with the patient's prescribed dosing schedule. In step 1298, the controller 304 transmits a diversion alert to the prescribing physician 130. Then, in step 1300, the controller 304 deactivates the pill dispenser 152 (e.g., by locking the dispensing gate 324 thereof). Next, in step 1302, the patient contacts patient services 122c and requests that the pill dispenser 152 be unlocked.

In step 1304, patient services 122c gathers patient identifying information to verify the identification of the patient. The process ends if patient services 122c cannot verify the identity of the patient. Alternatively, patient services 122c unlocks the pill dispenser 152 in step 1306 and enters the transaction into the patient database 134 if patient services 122c verifies the identity of the patient. Subsequently, the process proceeds to dispensing step 1126 ("K₂" as shown in FIGS. 23 and 30).

Figure 31:
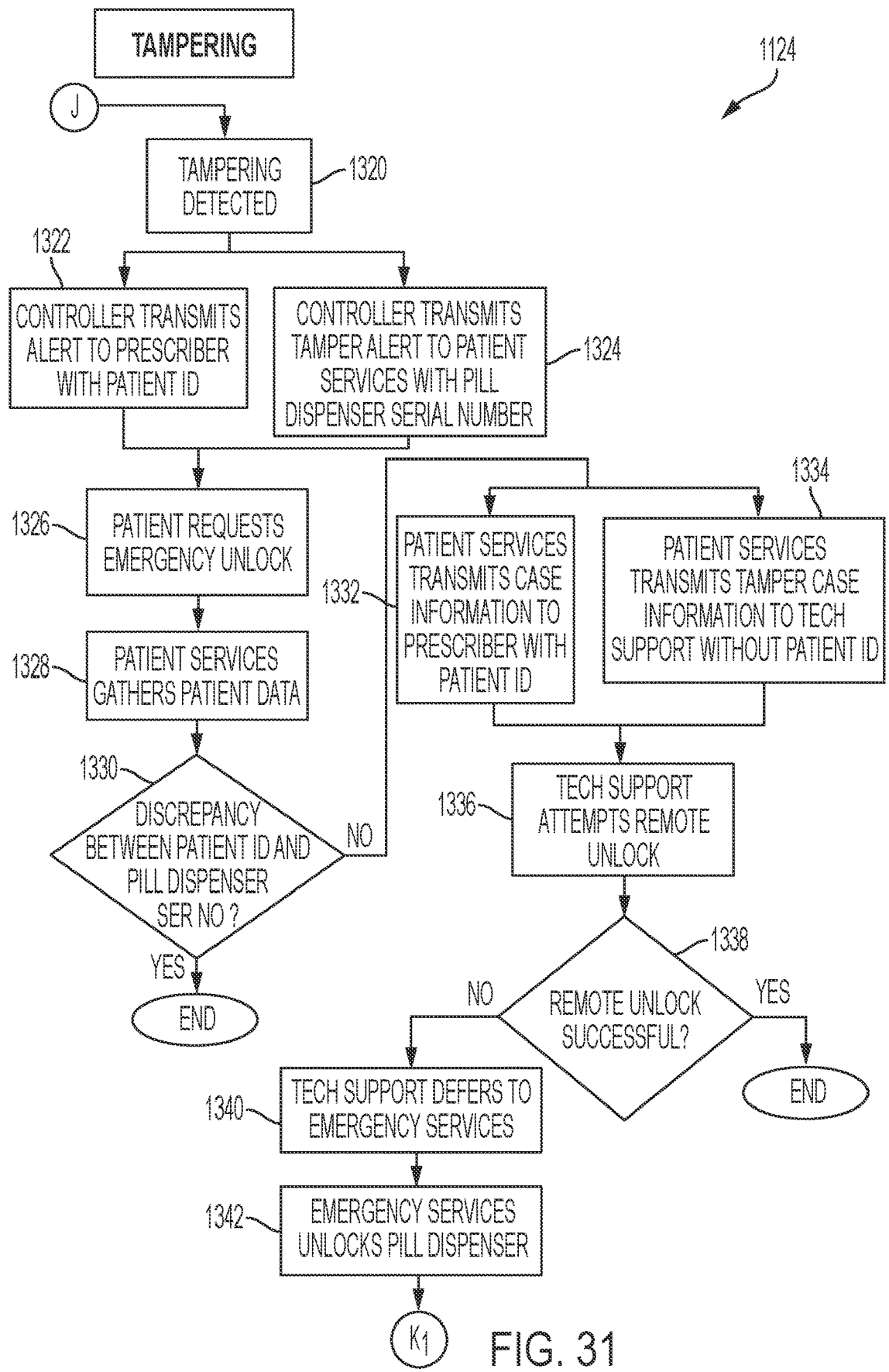
FIG. 31 is a flowchart illustrating step 1124 of FIG. 23 in greater detail.

FIG. 31 is a flowchart illustrating tampering step 1124 of FIG. 23 in greater detail. As noted above, the process proceeds to tampering step 1124 ("J" as shown in FIGS. 23, 28 and 31) when the controller 304 determines the conductive liner along the interior of the pill dispenser 152 is damaged (step 1236 of FIG. 28). During tampering step 1124, the system determines whether the patient has tampered with the pill dispenser 152 by improperly attempting to access the prescribed medication within the pill dispenser 152.

Generally, the pill dispenser 152 will enter a lockdown state when the pill dispenser 152 detects tampering. In the lockdown state, the pill dispenser 152 will transmit concurrent alerts to each of the prescribing physician 130 and patient services 122c. The alert transmitted to the prescribing physician 130 includes the patient identification information, the pill dispenser 152 serial number and the cause of the alert whereas the alert transmitted to patient services 122c may only include the pill dispenser 152 serial number. To unlock the pill dispenser 152, the patient is required to contact patient services 122c and a record of the interaction between the patient and patient services 122c is generated, recorded in the patient database 134 and forwarded to the prescribing physician 130.

Beginning in step 1320, the pill dispenser 152 detects tampering and enters a lockdown state. Subsequently, in step 1322, the pill dispenser 152 transmits an alert including patient identification information, the pill dispenser 152 serial number and the cause of the alert to the prescribing physician 152. Additionally, in step 1324, the pill dispenser 152 transmits an alert including the pill dispenser 152 serial number to patient services 122c. Then, in step 1326, the patient contacts patient services 122c and requests that the pill dispenser 152 be unlocked. In step 1328, patient services 122c requests and gathers identifying information from the patient to verify the patient's identity. For example, patient services 122c may request the patient's name and social security number and permission to match the same to the pill dispenser 152 serial number. A record of the interaction between the patient and patient services 122c is generated, recorded in the patient database 134 and forwarded to the prescribing physician 130.

In step 1330, patient services 122c determines whether a discrepancy exists between the identifying information provided by the patient and the pill dispenser 152 serial number. The process ends if patient services 122c determines a discrepancy exists. In the event a discrepancy exists, patient services may execute a series of steps to retrieve the pill dispenser 152. Alternatively, in step 1332, patient services 122c transmits the case information and patient identifying information to the prescribing physician 130 if patient services 122c determines a discrepancy does not exist between the identifying information provided by the patient and the pill dispenser 152 serial number. Additionally, in step 1334, patient services 122c transmits the case information without the patient identifying information to the technical support center 122a if patient services 122c determines a discrepancy does not exist between the identifying information provided by the patient and the pill dispenser 152 serial number. Subsequently, the technical support center 122a attempts to remotely unlock the pill dispenser 152 in step 1336.

In step 1338, it is determined whether the attempt to remotely unlock the pill dispenser 152 is successful. The process ends if the pill dispenser 152 is successfully unlocked. Alternatively, in step 1340, the technical support center 122a defers to the emergency field services offices 170 to unlock the pill dispenser 152 if the attempt to remotely unlock the pill dispenser 152 is unsuccessful. In step 1342, the emergency field services offices 170 unlocks the pill dispenser 152 and the process proceeds to dispensing step 1126 ("K₁" as shown in FIGS. 23 and 31). During dispensing step 1126, the pill dispenser 152 dispenses the patient's prescribed medication to the patient from the dispensing gate 324 of the pill dispenser 152. Dispensing step 1126 will be discussed in further detail below.

FIG. 32 is a flowchart illustrating dispensing step 1126 of FIG. 23 in greater detail. As noted above, the process proceeds to dispensing step 1126 ("K₁" as shown in FIGS. 23 and 31 and "K₂" as shown in FIGS. 23 and 30) if the pill dispenser 152 determines the saliva test is not required (step 1290 of FIG. 30), if the saliva sampling module result is consistent with the patient's prescribed dosing schedule (step 1296 of FIG. 30), after patient services 122c unlocks the pill dispenser 152 (step 1306 of FIG. 30), or after the emergency field services offices 170 unlocks the pill dispenser 152 (step 1342 of FIG. 31).

Beginning in step 1360, the controller 304 unlocks the dispensing gate 324. Next, in step 1362, the rotatable pill magazine 326 rotates one compartment width. The rotatable pill magazine 326 may have any configuration or shape so long as the size of the rotatable pill magazine 326 provides for the rotation of the rotatable pill magazine 326 about an axis within the housing of the pill dispenser 152. In step 1364, the dispensing gate 324 opens and in step 1366 the patient may remove the prescribed medication from the pill dispenser 152. Subsequently, in step 1368, the controller 304 locks the dispensing gate 324.

In step 1370, the controller 304 determines whether the prescription period is over (i.e., whether the rotatable pill magazine 326 of the pill dispenser 152 contains any more medication). The process returns to patient identification step 1118 ("M" as shown in FIGS. 23 and 32) if the controller 304 determines the prescription period is not over (i.e., the patient may receive another dose of medication according to the prescribed dosing schedule). Alternatively, the process proceeds to step 1372 if the controller 304 determines the prescription period is over. In step 1372, a patient may request a prescription renewal. The process returns to patient classification step 1110 ("L" as shown in FIGS. 23 and 32) if the patient requests a prescription renewal. The process proceeds to step 1374 if the patient does not request a prescription renewal.

In step 1374, the patient returns the pill dispenser 152 containing any remaining amount of prescribed medication to the pharmacy 140. Then, in step 1376 the pharmacy 140 verifies the projected amount of prescribed medication contained in the pill dispenser 152 based on the patient's prescribed dosing schedule stored in the patient database. In step 1378, the pharmacy 140 determines whether a discrepancy exists between the remaining amount of prescribed medication and the verified projected amount of prescribed medication. The process ends if a discrepancy does not exist between the remaining amount of prescribed medication and the verified projected amount of prescribed medication. If a discrepancy exists between the remaining amount of prescribed medication and the verified project amount of prescribed medication, then in step 1380 the pharmacy 140 reports the discrepancy to the prescribing physician 130. Subsequently, the process ends.

Having thus described the present disclosure in detail, it is to be understood that the foregoing description is not intended to limit the spirit or scope thereof. What is desired to be protected is set forth in the following claims.

What is claimed is:

1. A programmable medication dispenser, comprising:
a processor configured to receive a prescribed dosing schedule from a medical provider for dispensing medication from the programmable medication dispenser to a patient via a network-based control system;
a memory configured to store the prescribed dosing schedule;
a housing comprising plastic and having an underlying conductive foil inner lining;
a biometric verification module configured to verify an identity of the patient;
a saliva sampling module configured to verify a concentration of the medication in a bloodstream of the patient;
a receptacle having a plurality of compartments for storing the medication; and
a gate for dispensing the medication from one of the plurality of compartments, wherein
the processor
executes instructions to dispense the medication from the programmable medication dispenser to the patient according to the prescribed dosing schedule by controlling the biometric verification module, the saliva sampling module, the receptacle and the gate,
generates information based on at least one interaction between the programmable medication dispenser and the patient, and
transmits the information to at least one of a cloud-based database, a remote operations center, and the medical provider via the network-based control system, the database storing the information and being accessible to the medical provider.

2. The programmable medication dispenser of claim 1, wherein the processor
alerts the patient of an imminent dispensing event of the medication from one of the plurality of compartments according to the prescribed dosing schedule;
determines whether the conductive foil inner lining is damaged;
locks the programmable medication dispenser and detects the programmable medication dispenser has been tampered with when the conductive foil inner lining is damaged; and
transmits an alert indicating the programmable medication dispenser has been tampered with to the cloud-based database, the remote operations center and the medical provider via the network-based control system.

3. The programmable medication dispenser of claim 1, wherein the processor
alerts the patient of an imminent dispensing event of the medication from one of the plurality of compartments according to the prescribed dosing schedule;
determines whether the conductive foil inner lining is damaged;
prompts the patient to submit biometric data to the biometric verification module to verify the identity of the patient when the conductive foil inner lining is not damaged;
determines whether the patient is authorized to use the programmable medication dispenser based on a biometric verification module result;
determines whether a saliva sample of the patient is required when the biometric verification module result indicates the patient is authorized to use the programmable medication dispenser;
prompts the patient to submit a saliva sample to the saliva sampling module when the saliva sample of the patient is required;
determines whether the concentration of the medication in the bloodstream of the patient is consistent with the prescribed dosing schedule based on a saliva sampling module result; and
controls the gate for dispensing the medication from one of the plurality of compartments when the saliva sampling module result indicates the concentration of the medication in the bloodstream of the patient is consistent with the prescribed dosing.

4. The programmable medication dispenser of claim 1, wherein the processor
alerts the patient of an imminent dispensing event of the medication from one of the plurality of compartments according to the prescribed dosing schedule;
determines whether the conductive foil inner lining is damaged;
prompts the patient to submit biometric data to the biometric verification module to verify the identity of the patient when the conductive foil inner lining is not damaged;
determines whether the patient is authorized to use the programmable medication dispenser based on a biometric verification module result;
determines whether a saliva sample of the patient is required when the biometric verification module result indicates the patient is authorized to use the programmable medication dispenser;
prompts the patient to submit a saliva sample to the saliva sampling module when the saliva sample of the patient is required;
determines whether the concentration of the medication in the bloodstream of the patient is consistent with the prescribed dosing schedule based on a saliva sampling module result; and
transmits an alert indicating diversion of the medication to an unauthorized user to the cloud-based database and the medical provider via the network-based control system and locks the programmable medication dispenser when the saliva sampling module result indicates the concentration of the medication in the bloodstream of the patient is inconsistent with the prescribed dosing schedule.

5. The programmable medication dispenser of claim 1, wherein the processor
alerts the patient of an imminent dispensing event of the medication from one of the plurality of compartments according to the prescribed dosing schedule;
determines whether the conductive foil inner lining is damaged;
prompts the patient to submit biometric data to the biometric verification module to verify the identity of the patient when the conductive foil inner lining is not damaged;
determines whether the patient is authorized to use the programmable medication dispenser based on a biometric verification module result;
determines whether a saliva sample of the patient is required when the biometric verification module result indicates the patient is authorized to use the programmable medication dispenser; and
controls the gate for dispensing the medication from one of the plurality of compartments when the saliva sample of the patient is not required.

6. The programmable medication dispenser of claim 1, wherein the processor alerts the patient of an imminent dispensing event of the medication from one of the plurality of compartments according to the prescribed dosing schedule;

determines whether the conductive foil inner lining is damaged;

prompts the patient to submit biometric data to the biometric verification module to verify the identity of the patient when the conductive foil inner lining is not damaged;

determines whether the patient is authorized to use the programmable medication dispenser based on a biometric verification module result;

detects a theft of the programmable medication dispenser when the biometric verification module result indicates the patient is unauthorized to use the programmable medication dispenser; and locks the programmable medication dispenser and transmits an alert indicating the theft of the programmable medication dispenser to the cloud-based database and the remote operations center via the network-based control system based on the detection.

7. The programmable medication dispenser of claim 1, further comprising a global positioning system module, wherein the processor alerts the patient of an imminent dispensing event of the medication from one of the plurality of compartments according to the prescribed dosing schedule;

determines whether the conductive foil inner lining is damaged;

prompts the patient to submit biometric data to the biometric verification module to verify the identity of the patient when the conductive foil inner lining is not damaged;

determines whether the patient is authorized to use the programmable medication dispenser based on a biometric verification module result;

detects a theft of the programmable medication dispenser when the biometric verification module result indicates the patient is unauthorized to use the programmable medication dispenser;

locks the programmable medication dispenser and transmits an alert indicating the theft of the programmable medication dispenser to the cloud-based database and the remote operations center via the network-based control system based on the detection;

activates the global positioning system module to determine a location of the programmable medication dispenser; and transmits an alert indicating the location of the programmable medication dispenser to the cloud-based database and the remote operations center via the network-based control system when the location of the programmable medication dispenser is determined.

8. The programmable medication dispenser of claim 1, further comprising a global positioning system module, wherein the processor alerts the patient of an imminent dispensing event of the medication from one of the plurality of compartments according to the prescribed dosing schedule;

determines whether the conductive foil inner lining is damaged;

prompts the patient to submit biometric data to the biometric verification module to verify the identity of the patient when the conductive foil inner lining is not damaged;

determines whether the patient is authorized to use the programmable medication dispenser based on a biometric verification module result;

detects a theft of the programmable medication dispenser when the biometric verification module result indicates the patient is unauthorized to use the programmable medication dispenser;

locks the programmable medication dispenser and transmits an alert indicating the theft of the programmable medication dispenser to the cloud-based database and the remote operations center via the network-based control system based on the detection;

activates the global positioning system module to determine a location of the programmable medication dispenser; and transmits location attempt information to the cloud-based database via the network-based control system when the location of the programmable medication dispenser is not determined.

9. The programmable medication dispenser of claim 1, wherein the biometric verification module is one of a thumbprint recognition device, a blood analyzer and a retina scan.

10. A method for securely dispensing medication to a patient using a programmable medication dispenser and for mitigating a risk of diversion of the medication to an unauthorized user comprising the steps of:

receiving, by a processor of the programmable medication dispenser, a prescribed dosing schedule from a medical provider for dispensing medication from the programmable medication dispenser to a patient via a network-based control system;

storing the prescribed dosing schedule in a memory of the programmable medication dispenser;

executing instructions by the processor of the programmable medication dispenser to dispense the medication from the programmable medication dispenser to the patient according to the prescribed dosing schedule by controlling a biometric verification module of the programmable medication dispenser configured to verify an identity of the patient, a saliva sampling module of the programmable medication dispenser configured to verify a concentration of the medication in a bloodstream of the patient, a receptacle of the programmable medication dispenser having a plurality of compartments for storing the medication, and a gate of the programmable medication dispenser for dispensing the medication from one of the plurality of compartments;

generating information based on at least one interaction between the programmable medication dispenser and the patient; and transmitting the information to at least one of a cloud-based database, a remote operations center, and the medical provider via the network-based control system, the database storing the information and being accessible to the medical provider.

11. The method of claim 10, further comprising alerting, by the processor, the patient of an imminent dispensing event of the medication from one of the plurality of compartments according to the prescribed dosing schedule;

determining, by the processor, whether a conductive foil inner lining of a housing of the programmable medication dispenser is damaged;

locking, by the processor, the programmable medication dispenser and detecting, by the processor, the programmable medication dispenser has been tampered with when the conductive foil inner lining is damaged; and transmitting, by the processor, an alert indicating the programmable medication dispenser has been tampered with to the cloud-based database, the remote operations center and the medical provider via the network-based control system.

12. The method of claim 10, further comprising alerting, by the processor, the patient of an imminent dispensing event of the medication from one of the plurality of compartments according to the prescribed dosing schedule;

determining, by the processor, whether a conductive foil inner lining of a housing of the programmable medication dispenser is damaged;

prompting, by the processor, the patient to submit biometric data to the biometric verification module to verify the identity of the patient when the conductive foil inner lining is not damaged;

determining, by the processor, whether the patient is authorized to use the programmable medication dispenser based on a biometric verification module result;

determining, by the processor, whether a saliva sample of the patient is required when the biometric verification module result indicates the patient is authorized to use the programmable medication dispenser;

prompting, by the processor, the patient to submit a saliva sample to the saliva sampling module when the saliva sample of the patient is required;

determining, by the processor, whether the concentration of the medication in the bloodstream of the patient is consistent with the prescribed dosing schedule based on a saliva sampling module result; and controlling, by the processor, the gate for dispensing the medication from one of the plurality of compartments when the saliva sampling module result indicates the concentration of the medication in the bloodstream of the patient is consistent with the prescribed dosing.

13. The method of claim 10, further comprising alerting, by the processor, the patient of an imminent dispensing event of the medication from one of the plurality of compartments according to the prescribed dosing schedule;

determining, by the processor, whether a conductive foil inner lining of a housing of the programmable medication dispenser is damaged;

prompting, by the processor, the patient to submit biometric data to the biometric verification module to verify the identity of the patient when the conductive foil inner lining is not damaged;

determining, by the processor, whether the patient is authorized to use the programmable medication dispenser based on a biometric verification module result;

determining, by the processor, whether a saliva sample of the patient is required when the biometric verification module result indicates the patient is authorized to use the programmable medication dispenser;

prompting, by the processor, the patient to submit a saliva sample to the saliva sampling module when the saliva sample of the patient is required;

determining, by the processor, whether the concentration of the medication in the bloodstream of the patient is consistent with the prescribed dosing schedule based on a saliva sampling module result; and transmitting, by the processor, an alert indicating diversion of the medication to an unauthorized user to the cloud-based database and the medical provider via the network-based control system and locking, by the processor, the programmable medication dispenser when the saliva sampling module result indicates the concentration of the medication in the bloodstream of the patient is inconsistent with the prescribed dosing schedule.

14. The method of claim 10, further comprising alerting, by the processor, the patient of an imminent dispensing event of the medication from one of the plurality of compartments according to the prescribed dosing schedule;

determining, by the processor, whether a conductive foil inner lining of a housing of the programmable medication dispenser is damaged;

prompting, by the processor, the patient to submit biometric data to the biometric verification module to verify the identity of the patient when the conductive foil inner lining is not damaged;

determining, by the processor, whether the patient is authorized to use the programmable medication dispenser based on a biometric verification module result;

determining, by the processor, whether a saliva sample of the patient is required when the biometric verification module result indicates the patient is authorized to use the programmable medication dispenser; and controlling, by the processor, the gate for dispensing the medication from one of the plurality of compartments when the saliva sample of the patient is not required.

15. The method of claim 10, further comprising alerting, by the processor, the patient of an imminent dispensing event of the medication from one of the plurality of compartments according to the prescribed dosing schedule;

determining, by the processor, whether a conductive foil inner lining of a housing of the programmable medication dispenser is damaged;

prompting, by the processor, the patient to submit biometric data to the biometric verification module to verify the identity of the patient when the conductive foil inner lining is not damaged;

determining, by the processor, whether the patient is authorized to use the programmable medication dispenser based on a biometric verification module result;

detecting, by the processor, a theft of the programmable medication dispenser when the biometric verification module result indicates the patient is unauthorized to use the programmable medication dispenser; and locking, by the processor, the programmable medication dispenser and transmitting, by the processor, an alert indicating the theft of the programmable medication dispenser to the cloud-based database and the remote operations center via the network-based control system based on the detection.

16. The method of claim 10, further comprising alerting, by the processor, the patient of an imminent dispensing event of the medication from one of the plurality of compartments according to the prescribed dosing schedule;

determining, by the processor, whether a conductive foil inner lining of a housing of the programmable medication dispenser is damaged;

prompting, by the processor, the patient to submit biometric data to the biometric verification module to verify the identity of the patient when the conductive foil inner lining is not damaged;

determining, by the processor, whether the patient is authorized to use the programmable medication dispenser based on a biometric verification module result;

detecting, by the processor, a theft of the programmable medication dispenser when the biometric verification module result indicates the patient is unauthorized to use the programmable medication dispenser;

locking, by the processor, the programmable medication dispenser and transmitting, by the processor, an alert indicating the theft of the programmable medication dispenser to the cloud-based database and the remote operations center via the network-based control system based on the detection;

activating, by the processor, a global positioning system module of the programmable medication dispenser to determine a location of the programmable medication dispenser; and transmitting, by the processor, an alert indicating the location of the programmable medication dispenser to the cloud-based database and the remote operations center via the network-based control system when the location of the programmable medication dispenser is determined.

17. The method of claim 10, further comprising alerting, by the processor, the patient of an imminent dispensing event of the medication from one of the plurality of compartments according to the prescribed dosing schedule;

determining, by the processor, whether a conductive foil inner lining of a housing of the programmable medication dispenser is damaged;

prompting, by the processor, the patient to submit biometric data to the biometric verification module to verify the identity of the patient when the conductive foil inner lining is not damaged;

determining, by the processor, whether the patient is authorized to use the programmable medication dispenser based on a biometric verification module result;

detecting, by the processor, a theft of the programmable medication dispenser when the biometric verification module result indicates the patient is unauthorized to use the programmable medication dispenser;

locking, by the processor, the programmable medication dispenser and transmitting, by the processor, an alert indicating the theft of the programmable medication dispenser to the cloud-based database and the remote operations center via the network-based control system based on the detection;

activating, by the processor, a global positioning system module of the programmable medication dispenser to determine a location of the programmable medication dispenser; and transmitting, by the processor, location attempt information to the cloud-based database via the network-based control system when the location of the programmable medication dispenser is not determined.

18. A system for securely dispensing medication to a patient and for mitigating the risk of diversion of the medication to an unauthorized user, comprising a network-based control system; and a programmable medication dispenser in communication with the network-based control system, the programmable medication dispenser having a a processor configured to receive a prescribed dosing schedule from a medical provider for dispensing the medication from the programmable medication dispenser to a patient via the network-based control system, a memory configured to store the prescribed dosing schedule, a housing comprising plastic and having an underlying conductive foil inner lining;

a biometric verification module configured to verify an identity of the patient;

a saliva sampling module configured to verify a concentration of the medication in a bloodstream of the patient;

a receptacle having a plurality of compartments for storing the medication; and a gate for dispensing the medication from one of the plurality of compartments, wherein the processor executes instructions to dispense the medication from the programmable medication dispenser to the patient according to the prescribed dosing schedule by controlling the biometric verification module, the saliva sampling module, the receptacle and the gate, generates information based on at least one interaction between the programmable medication dispenser and the patient, and transmits the information to at least one of a cloud-based database, a remote operations center, and the medical provider via the network-based control system, the database storing the information and being accessible to the medical provider.

19. The system of claim 18, wherein the system is implemented in a cloud-based environment and provides centralized, cloud-based monitoring and control of a network of programmable medication dispensers.

20. The system of claim 18, wherein the processor alerts the patient of an imminent dispensing event of the medication from one of the plurality of compartments according to the prescribed dosing schedule;

determines whether the conductive foil inner lining is damaged;

locks the programmable medication dispenser and detects the programmable medication dispenser has been tampered with when the conductive foil inner lining is damaged; and transmits an alert indicating the programmable medication dispenser has been tampered with to the cloud-based database, the remote operations center and the medical provider via the network-based control system.

21. The system of claim 18, wherein the processor alerts the patient of an imminent dispensing event of the medication from one of the plurality of compartments according to the prescribed dosing schedule;

determines whether the conductive foil inner lining is damaged;

prompts the patient to submit biometric data to the biometric verification module to verify the identity of the patient when the conductive foil inner lining is not damaged;

determines whether the patient is authorized to use the programmable medication dispenser based on a biometric verification module result;

determines whether a saliva sample of the patient is required when the biometric verification module result indicates the patient is authorized to use the programmable medication dispenser;

prompts the patient to submit a saliva sample to the saliva sampling module when the saliva sample of the patient is required;

determines whether the concentration of the medication in the bloodstream of the patient is consistent with the prescribed dosing schedule based on a saliva sampling module result; and controls the gate for dispensing the medication from one of the plurality of compartments when the saliva sampling module result indicates the concentration of the medication in the bloodstream of the patient is consistent with the prescribed dosing.

22. The system of claim 18, wherein the processor alerts the patient of an imminent dispensing event of the medication from one of the plurality of compartments according to the prescribed dosing schedule;

determines whether the conductive foil inner lining is damaged;

prompts the patient to submit biometric data to the biometric verification module to verify the identity of the patient when the conductive foil inner lining is not damaged;
determines whether the patient is authorized to use the programmable medication dispenser based on a biometric verification module result;
determines whether a saliva sample of the patient is required when the biometric verification module result indicates the patient is authorized to use the programmable medication dispenser;
prompts the patient to submit a saliva sample to the saliva sampling module when the saliva sample of the patient is required;
determines whether the concentration of the medication in the bloodstream of the patient is consistent with the prescribed dosing schedule based on a saliva sampling module result; and
transmits an alert indicating diversion of the medication to an unauthorized user to the cloud-based database and the medical provider via the network-based control system and locks the programmable medication dispenser when the saliva sampling module result indicates the concentration of the medication in the bloodstream of the patient is inconsistent with the prescribed dosing schedule.

23. The system of claim 18, wherein the processor
alerts the patient of an imminent dispensing event of the medication from one of the plurality of compartments according to the prescribed dosing schedule;
determines whether the conductive foil inner lining is damaged;
prompts the patient to submit biometric data to the biometric verification module to verify the identity of the patient when the conductive foil inner lining is not damaged;
determines whether the patient is authorized to use the programmable medication dispenser based on a biometric verification module result;
determines whether a saliva sample of the patient is required when the biometric verification module result indicates the patient is authorized to use the programmable medication dispenser; and
controls the gate for dispensing the medication from one of the plurality of compartments when the saliva sample of the patient is not required.

24. The system of claim 18, wherein the processor
alerts the patient of an imminent dispensing event of the medication from one of the plurality of compartments according to the prescribed dosing schedule;
determines whether the conductive foil inner lining is damaged;
prompts the patient to submit biometric data to the biometric verification module to verify the identity of the patient when the conductive foil inner lining is not damaged;
determines whether the patient is authorized to use the programmable medication dispenser based on a biometric verification module result;
detects a theft of the programmable medication dispenser when the biometric verification module result indicates the patient is unauthorized to use the programmable medication dispenser; and
locks the programmable medication dispenser and transmits an alert indicating the theft of the programmable medication dispenser to the cloud-based database and the remote operations center via the network-based control system based on the detection.

25. The system of claim 18, wherein the programmable medication dispenser includes a global positioning system module, and
the processor
alerts the patient of an imminent dispensing event of the medication from one of the plurality of compartments according to the prescribed dosing schedule;
determines whether the conductive foil inner lining is damaged;
prompts the patient to submit biometric data to the biometric verification module to verify the identity of the patient when the conductive foil inner lining is not damaged;
determines whether the patient is authorized to use the programmable medication dispenser based on a biometric verification module result;
detects a theft of the programmable medication dispenser when the biometric verification module result indicates the patient is unauthorized to use the programmable medication dispenser;
locks the programmable medication dispenser and transmits an alert indicating the theft of the programmable medication dispenser to the cloud-based database and the remote operations center via the network-based control system based on the detection;
activates the global positioning system module to determine a location of the programmable medication dispenser; and
transmits an alert indicating the location of the programmable medication dispenser to the cloud-based database and the remote operations center via the network-based control system when the location of the programmable medication dispenser is determined.

26. The system of claim 18, wherein the programmable medication dispenser includes a global positioning system module, and
the processor
alerts the patient of an imminent dispensing event of the medication from one of the plurality of compartments according to the prescribed dosing schedule;
determines whether the conductive foil inner lining is damaged;
prompts the patient to submit biometric data to the biometric verification module to verify the identity of the patient when the conductive foil inner lining is not damaged;
determines whether the patient is authorized to use the programmable medication dispenser based on a biometric verification module result;
detects a theft of the programmable medication dispenser when the biometric verification module result indicates the patient is unauthorized to use the programmable medication dispenser;
locks the programmable medication dispenser and transmits an alert indicating the theft of the programmable medication dispenser to the cloud-based database and the remote operations center via the network-based control system based on the detection;
activates the global positioning system module to determine a location of the programmable medication dispenser; and
transmits location attempt information to the cloud-based database via the network-based control system when the location of the programmable medication dispenser is not determined.

* * * * *